US008912177B2

(12) United States Patent
Natoli et al.

(10) Patent No.: US 8,912,177 B2
(45) Date of Patent: Dec. 16, 2014

(54) METHOD OF TREATING POLYCYSTIC KIDNEY DISEASES WITH CERAMIDE DERIVATIVES

(75) Inventors: Thomas A. Natoli, Woburn, MA (US); Oxana Ibraghimov-Beskrovnaya, Southborough, MA (US); John P. Leonard, Manchester, NH (US); Nelson S. Yew, West Upton, MA (US); Seng H. Cheng, Natick, MA (US)

(73) Assignee: Genzyme Corporation, Cambridge, MA (US)

( * ) Notice: Subject to any disclaimer, the term of this patent is extended or adjusted under 35 U.S.C. 154(b) by 865 days.

(21) Appl. No.: 12/681,291

(22) PCT Filed: Oct. 3, 2008

(86) PCT No.: PCT/US2008/011450
§ 371 (c)(1),
(2), (4) Date: Jun. 18, 2010

(87) PCT Pub. No.: WO2009/045503
PCT Pub. Date: Apr. 9, 2009

(65) Prior Publication Data
US 2010/0298317 A1    Nov. 25, 2010

Related U.S. Application Data

(60) Provisional application No. 60/997,803, filed on Oct. 5, 2007.

(51) Int. Cl.
A61K 31/54   (2006.01)
A01N 43/36   (2006.01)
A61K 31/40   (2006.01)
A61K 31/4025 (2006.01)

(52) U.S. Cl.
CPC .................................. A61K 31/4025 (2013.01)
USPC ...................... 514/233.8; 514/237.8; 514/422

(58) Field of Classification Search
None
See application file for complete search history.

(56) References Cited

U.S. PATENT DOCUMENTS

| 4,065,562 | A | 12/1977 | Ohata et al. |
| 4,182,767 | A | 1/1980 | Murai et al. |
| 4,533,668 | A | 8/1985 | Matsumura et al. |
| 4,639,436 | A | 1/1987 | Junge et al. |
| 5,041,441 | A | 8/1991 | Radin et al. |
| 5,302,609 | A | 4/1994 | Shayman et al. |
| 5,472,969 | A | 12/1995 | Platt et al. |
| 5,525,616 | A | 6/1996 | Platt et al. |
| 5,631,394 | A | 5/1997 | Wei et al. |
| 5,707,649 | A | 1/1998 | Inokuchi et al. |
| 5,763,438 | A | 6/1998 | Inokuchi et al. |
| 5,849,326 | A | 12/1998 | Inokuchi et al. |
| 5,907,039 | A | 5/1999 | Jinbo et al. |
| 5,916,911 | A | 6/1999 | Shayman et al. |
| 5,945,442 | A | 8/1999 | Shayman et al. |
| 5,952,370 | A | 9/1999 | Shayman et al. |
| 5,972,928 | A | 10/1999 | Chatterjee |
| 6,030,995 | A | 2/2000 | Shayman et al. |
| 6,040,332 | A | 3/2000 | Shayman et al. |
| 6,051,598 | A | 4/2000 | Shayman et al. |
| 6,228,889 | B1 | 5/2001 | Chatterjee |
| 6,255,336 | B1 | 7/2001 | Shayman et al. |
| 6,335,444 | B1 | 1/2002 | Jimbo et al. |
| 6,407,064 | B2 | 6/2002 | Masuda et al. |
| 6,511,979 | B1 | 1/2003 | Chatterjee |
| 6,569,889 | B2 | 5/2003 | Shayman et al. |
| 6,610,703 | B1 | 8/2003 | Jacob et al. |
| 6,660,749 | B2 | 12/2003 | Butters et al. |
| 6,835,831 | B2 | 12/2004 | Hirth |
| 6,855,830 | B2 | 2/2005 | Hirth et al. |
| 6,890,949 | B1 | 5/2005 | Shayman et al. |
| 6,916,802 | B2 | 7/2005 | Shayman et al. |
| 7,148,251 | B2 | 12/2006 | Shayman |
| 7,196,205 | B2 | 3/2007 | Siegel et al. |
| 7,253,185 | B2 | 8/2007 | Shayman et al. |
| 7,265,228 | B2 | 9/2007 | Hirth et al. |

(Continued)

FOREIGN PATENT DOCUMENTS

EP    126974 A1    12/1984
EP    0 144 290 A    6/1985

(Continued)

OTHER PUBLICATIONS

Qi Qian et al. (Kidney International (2001) 59, 2005-2022; doi:10.1046/j.1523 1755.2001.00716).*

(Continued)

Primary Examiner — Jeffrey S. Lundgren
Assistant Examiner — William Lee
(74) Attorney, Agent, or Firm — Hamilton, Brook, Smith & Reynolds, P.C.

(57) ABSTRACT

A method of treating polycystic kidney disease in a subject comprises administering to the subject an effective amount of a compound represented by Structural Formula (1): or a pharmaceutically acceptable salt thereof.

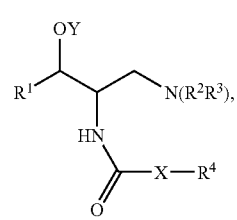

(1)

13 Claims, No Drawings

(56) References Cited

U.S. PATENT DOCUMENTS

| | | |
|---|---|---|
| 7,335,681 B2 | 2/2008 | Shayman et al. |
| 7,615,573 B2 | 11/2009 | Siegel et al. |
| 7,763,738 B2 | 7/2010 | Hirth et al. |
| 8,003,617 B2 | 8/2011 | Cheng et al. |
| 8,304,447 B2 | 11/2012 | Siegel et al. |
| 8,309,593 B2 | 11/2012 | Siegel et al. |
| 8,389,517 B2 | 3/2013 | Ibraghimov-Beskrovnaya et al. |
| 2001/0003741 A1 | 6/2001 | Masuda et al. |
| 2002/0156107 A1 | 10/2002 | Shayman et al. |
| 2002/0198240 A1 | 12/2002 | Shayman et al. |
| 2003/0050299 A1 | 3/2003 | Hirth et al. |
| 2003/0073680 A1 | 4/2003 | Shayman et al. |
| 2004/0260099 A1 | 12/2004 | Shayman |
| 2005/0009872 A1 | 1/2005 | Hirth et al. |
| 2005/0049235 A1 | 3/2005 | Shayman et al. |
| 2005/0222244 A1 | 10/2005 | Siegel et al. |
| 2005/0239862 A1 | 10/2005 | Shayman et al. |
| 2005/0267094 A1 | 12/2005 | Shayman et al. |
| 2006/0058349 A1 | 3/2006 | Ali et al. |
| 2006/0074107 A1 | 4/2006 | Butters et al. |
| 2006/0217560 A1 | 9/2006 | Shayman |
| 2007/0066581 A1 | 3/2007 | Aerts |
| 2007/0072916 A1 | 3/2007 | Shayman |
| 2007/0112028 A1 | 5/2007 | Orchard |
| 2007/0203223 A1 | 8/2007 | Siegel et al. |
| 2008/0146533 A1 | 6/2008 | Shayman et al. |
| 2009/0312392 A1 | 12/2009 | Shayman et al. |
| 2010/0256216 A1 | 10/2010 | Siegel et al. |
| 2011/0166134 A1 | 7/2011 | Ibraghimov-Beskrovnaya et al. |
| 2011/0184021 A1 | 7/2011 | Siegel et al. |
| 2012/0022126 A1 | 1/2012 | Cheng et al. |
| 2012/0322786 A1 | 12/2012 | Siegel et al. |
| 2012/0322787 A1 | 12/2012 | Siegel et al. |
| 2013/0225573 A1 | 8/2013 | Ibraghimov-Beskrovnaya et al. |

FOREIGN PATENT DOCUMENTS

| | | |
|---|---|---|
| EP | 0 765 865 A1 | 4/1997 |
| EP | 1 384 719 A1 | 1/2004 |
| EP | 1 528 056 A1 | 5/2005 |
| EP | 1 576 894 A1 | 9/2005 |
| GB | 2054371 | 2/1981 |
| JP | 35-5798 | 5/1960 |
| JP | 9-169664 | 6/1997 |
| JP | 9216856 A1 | 8/1997 |
| JP | 10-324671 | 12/1998 |
| JP | 10338636 A | 12/1998 |
| JP | 2003-238410 A | 8/2003 |
| WO | WO 97/10817 | 3/1997 |
| WO | WO 98/52553 | 11/1998 |
| WO | WO 01/04108 A1 | 1/2001 |
| WO | WO 01/54654 A2 | 8/2001 |
| WO | WO 01/80852 A1 | 11/2001 |
| WO | WO 02/50019 A2 | 6/2002 |
| WO | WO 02/055498 A1 | 7/2002 |
| WO | WO 03/008399 A1 | 1/2003 |
| WO | WO 03/057874 A1 | 7/2003 |
| WO | WO 03/068255 A1 | 8/2003 |
| WO | WO 2004/007453 A1 | 1/2004 |
| WO | WO 2004/056748 A1 | 7/2004 |
| WO | WO 2004/078193 A1 | 9/2004 |
| WO | WO 2005/040118 A1 | 5/2005 |
| WO | WO 2005/039578 A2 | 6/2005 |
| WO | WO 2005/063275 A1 | 7/2005 |
| WO | WO 2005/087023 A1 | 9/2005 |
| WO | WO 2005/108600 A1 | 11/2005 |
| WO | WO 2005/123055 A2 | 12/2005 |
| WO | WO 2006/023827 A2 | 3/2006 |
| WO | WO 2006/053043 A2 | 5/2006 |
| WO | WO 2006/053043 A3 | 5/2006 |
| WO | WO 2007/022518 A2 | 2/2007 |
| WO | WO 2007/134086 A2 | 11/2007 |
| WO | WO 2007/134086 A3 | 11/2007 |
| WO | WO 2008/011478 A2 | 1/2008 |
| WO | WO 2008/011487 A2 | 1/2008 |
| WO | WO 2008/012555 A2 | 1/2008 |
| WO | WO 2008/024337 A2 | 2/2008 |
| WO | WO 2008/150486 A2 | 12/2008 |
| WO | WO 2009/045503 A1 | 4/2009 |
| WO | WO 2009/117150 A2 | 9/2009 |

OTHER PUBLICATIONS

International Preliminary Report on Patentability for International Application No. PCT/US2009/051864 dated Feb. 1, 2011.
*Office Action for U.S. Appl. No. 12/227,076 dated Mar. 20, 2012.
Notification of Transmittal of the International Search Report and Written Opinion of the International Searching Authority from counterpart International Application No. PCT/US2008/006906, dated Apr. 12, 2008.
Jimbo, M., et al., "Development of a New Inhibitor of Glucosylceramide Synthase", *J. Biochem*, 127: 485-491 (2000).
Inokuchi, K., et al., "Aminoalcohol derivatives for treatment of abnormal proliferative diseases", *Chemical Abstracts Service*, XP002495476 retrieved from CAPLUS Database accession No. 1998:816280 (abstract).
Alberti, C., et al., "Chloramphenicol. XII and XIII. Chloramphenicol analogs. p-Nitrophenyldiaminopropanols", *Chemical Abstracts Service*, XP002495477 retrieved from CAPLUS Database accession No. 1957:17088 (abstract).
Comuzzie, A.G., et al., "The Baboon as a Nonhuman Primate Model for the Study of the Genetics of Obesity", *Obesity Research*, 11(1):75-80 (2003).
Inokuchi, J., el al., "Inhibition of Experimental Metastasis of Murine Lewis Lung Carcinoma by an Inhibitor of Glucosylceramide Synthase and Its Possible Mechanism of Action", *Cancer Research*, 50:6731-6737 (1990).
Nojiri, H., et al., "Ganglioside GM3: An acidic membrane component that increases during macrophage-like cell differentiation can induce monocytic differentiation of human myeloid and monoctyoid leukemic cell lines HL-60 and U937", *Proc. Natl. Acad. Sci.*, 83:782-786 (1986).
Rubino, MD., F., et al., "Letter to the Editor", *Annals of Surgery*, 240(2):389-390 (2004).
Svensson, M., et al., "Epithelial Glucosphingolipid Express as a Determinant of Bacterial Adherence and Cytokine Production", *Infection and Immunity*, 62:10 pp. 4404-4410 (1994).
Tagami, S., et al., "Ganglioside GM3 Participates in the Pathological Conditions of Insulin Resistance", *The Journal of Biological Chemistry*, 227(5):3085-3092 (2002).
Yamashita, T., et al., "Enhanced insulin sensitivity in mice lacking ganglioside GM3", *Proc. Natl. Acad. Scl.*, 100(6): 3445-3449 (2003).
Chatterjee, S., et al.,"Role of lactosylceramide and MAP kinase in the proliferation of proximal tubular cells in human polycystic kidney disease", *Journal of Lipid Research*, 37(6): 1334-1344 (1996).
Chatterjee, S., et al.,"Oxidized Low Density Lipoprotein Stimulates Aortic Smooth Muscle Cell Proliferation", *Glycobiology*, 6(3): 303-311 (1996).
Dickie, P., et al., "HIV-Associated Nephropathy in Transgenic Mice Expressing HIV-1 Genes," *Virology*, 185:109-119, 1991.
Folch, J., et al., "A Simple Method for the Isolation and Purification of Total Lipides from Animal Tissues", *J. Biol. Chem.*, 226:497-509, 1957.
Freireich, E., et al., "Quantitative Comparison of Toxicity of Anticancer Agents in Mouse, Rat, Hampster, Dog, Monkey, and Man", Cancer Chemother. Reports 50(4):219 (1996).
Gill-Randall, R.J., et al., "Is human Type 2 diabetes maternally inherited? Insights from an animal model", Diabet. Med. 21 (7):759 (2004).
Hakomori, S. "New Directions in Cancer Therapy Based on Aberrant Expression of Glycosphingolipids: Anti-adhesion and Ortho-Signaling Therapy," *Cancer Cells* 3:461-470 (1991).
Inokuchi, J. et al., "Antitumor Activity Via Inhibition of Glycosphingolipid Biosynthesis," *Cancer Lett.*, 38:23-30(1987).
Jankowski, K., "Microdetermination of phosphorus in organic materials from polymer industry by microwave-induced plasma atomic emission spectrometry after microwave digestion", *Microchem. J.*, 70:41-49, 2001.

(56) References Cited

OTHER PUBLICATIONS

Lee, L., et al. "Improved Inhibitors of Glucosylceramide Synthase", *J. of Bio Chem.*, 274(21): 14662-14669 (1999).
Zador, I., et al. "A Role for Glycosphingolipid Accumulation in the Renal Hypertrophy of Streptozotocin-induced Diabetes Mellitus", *J. Clin. Invest.*, 91: 797-803 (1993).
Zhao, H., et al., "Inhibiting glycosphingolipid systhesis improves glycemic control and insulin sensitivity in animal models of type 2 diabetes.", *Diabetes*, 56(5): 1210-1218 (2007).
Ziche, M. et al., "Angiogenesis Can Be Stimulated or Repressed In Vivo by a Change in GM3 :GD3 Ganglioside Ratio," *Lab. Invest.*, 67:711-715 (1992).
Notification Concerning Transmittal of International Preliminary Report on Patentability for International Application No. PCT/US2008/006906 Dated Dec. 10, 2009.
Notification of Transmittal of the International Search Report and Written Opinion of the International Searching Authority from counterpart International Application No. PCT/US2008/011450, dated Jan. 21, 2009.
Notification of Transmittal of the International Search Report and Written Opinion of the International Searching Authority from counterpart International Application No. PCT/US2009/001773, dated Nov. 11, 2009.
Notification of Transmittal of the International Search Report and Written Opinion of the International Searching Authority from counterpart International Application No. PCT/US2009/051864, dated Nov. 3, 2009.
Notification of Transmittal of the International Search Report and Written Opinion of the International Searching Authority from counterpart International Application No. PCT/US2009/005435, dated Feb. 12, 2010.
Notice of Allowance and Fee(s) Due for U.S. Appl. No. 11/667,224; Date Mailed: Apr. 22, 2011.
Abe, A., et al., "Use of Sulfobutyl Ether β-Cyclodextrin as a Vehicle for *d-threo*-1-Phenyl-2-decanoylamino-3-morpholinopropanol-Related Glucosylceramide Synthase Inhibitors", *Analytical Biochemistry*, vol. 287, pp. 344-347 (2000).
Levery, S.B., et al., "Disruption of the glucosylceramide biosynthetic pathway in *Aspergillus nidulans* and *Aspergillus fumigatus* by inhibitors of UDP-GLC: Ceramide glucosyltransferase strongly affects spore germination, cell cycle, and hyphal growth", *FEBS Letters*, vol. 525, pp. 59-64 (2002).
*Office Action dated Mar. 29, 2012 for U.S. Appl. No. 12/601,871, titled "2-Acylaminopropoanol-Type Glucosylceramide Synthase Inhibitors".
*Non-Final Office Action dated Apr. 27, 2012 for U.S. Appl. No. 13/122,135, titled "2-Acylaminopropoanol-Type Glucosylceramide Synthase Inhibitors".
Notification of Office Action for European Patent Office for EP Patent Application No. 05 826 118.1-1216 dated Nov. 13, 2007.
International Preliminary Report on Patentability issued in International Application PCT/US2005/040596 dated May 15, 2007.
*Notice of Allowance and Fee(s) Due for U.S. Appl. No. 12/601,871; "2-Acylaminopropoanol-Type Glucosylceramide Synthase Inhibitors" Date Mailed: Aug. 9, 2012.
*Notice of Allowance and Fee(s) Due for U.S. Appl. No. 13/122,135; "2-Acylaminopropoanol-Type Glucosylceramide Synthase Inhibitors" Date Mailed: Aug. 1, 2012.
Tay-Sachs, URL: http://www.ninds.nih.gov/disorders/taysachs/taysachs.htm. National Institute of Health of Neurological Disorders and Stroke. Accessed online Sep. 9, 2011.
*Office Action for U.S. Appl. No. 12/601,871 dated Sep. 21, 2011.
International Preliminary Report on Patentability for International Application No. PCT/US2008/011450 dated Apr. 7, 2010.
International Preliminary Report on Patentability for International Application No. PCT/US2009/001773 dated Sep. 21, 2010.
Abe, A., et al., "Reduction of Globotriasylceramide in Fabry Disease mice by substrate deprivation", *J. Clin Invest.* 105(11): 1563-1571, (2000).
*Non-Final Office Action for U.S. Appl. No. 12/227,076 mailed on Nov. 23, 2011.
Ong, et al., "Nonalcoholic Fatty Liver Disease and the epidemic of Obesity", *Cleveland Clinic Journal of Medicine*, 71(8): 657-664 (Aug. 2004).
Schwimmer, J.B., et al., "Obesity, Insulin Resistance, and and Other Clinicopathological Correlates of Pediatric Nonalcoholic Fatty Liver Disease", *Journal of Pediatrics*, 143(4): 500-505 (2003).
Nicolaus, B.J.R., "Symbiotic Approach to Drug Design", *Decision Making in Drug Research*, XP-001111439, p. 1-14 (1983).
Notification concerning Transmittal of International Preliminary Report on Patentability for International Application No. PCT/US2009/005435 dated Apr. 5, 2011.
Abe, A., et al., "Improved Inhibitors of Glucosylceramide Synthase," *J. Biochem.*,.111:191-196 (1992).
Abe, A., et al., "Induction of Glucosylceramide Synthase by Synthase Inhibitors and Ceramide," *Biochim. Biophys. Acta*, 1299: 333-341 (1996).
Abe, A., et al., "Metabolic Effects of Short-Chain Ceramide and Glucosylceramide on Sphingolipids and Protein Kinase C," *Eur. J. Biochem*, 210: 765-773 (1992).
Abe, A., et al., "Structural and stereochemical studies of potent inhibitors of glucosylceramide synthase and tumor cell growth," *J. of Lipid Research*, 36:611-621 (1995).
Abdel-Magid, A., et al., "Metal-Assisted Aldol Condensation of Chiral α-Halogenated Imide Enolates: A Stereocontrolled Chiral Epoxide Syntheses, "*J. Am. Chem Soc.*, 108: 4595-4602 (1986).
Alker, D., et al., "Application of Enantiopure Templated Azomethine Ylids to β-Hydroxy-α-amino Acid Syntheses," *Tetrahedron*: 54: 6089-6098 (1998).
Alon, R., et al., "Glycolipid Ligands for Selectins Support Leukocyte Tethering and Rolling Under Physiologic Flow Conditions," *J. Immunol.*, 154: 5356-5366 (1995).
Ames, Bruce N., "Assay of Inorganic Phosphate, Total Phosphate and Phosphatases," *Methods Enzymol.*, 8: 115-118 (1996).
Bielawska, A., et al., "Ceramide-Mediated Biology: Determination of Structural and Stereospecific Requirements Through the Use of *N*-Acyl-Phenylaminoalcohol Analogs," *J. Biol. Chem.*, 267: 18493-18497 (1992).
Bielawska, et al., "Modulation of Cell Growth and Differentiation by Ceramide," *FEBS Letters*, 307(2): 211-214 (1992).
Blobe, G.C., et al., "Regulation of Protein Kinase C and its Role in Cancer Biology," *Cancer Metastasis Rev.*, 13: 411-431 (1994).
Brenkert, A., et al., "Synthesis of Galactosyl Ceramide and Glucosyl Ceramide by Rat Brain: Assay Procedures and Changes with Age," *Brain Res.*, 36: 183-193 (1972).
CAPLUS Listing of Accession No. 1985:221199, Keith McCullagh, et al., "Carboxyalkyl peptide derivatives."
Carson, K.G., et al., "Studies on Morpholinosphingolipids: Potent Inhibitors of Glucosylceramide Synthase," *Tetrahedron Letters*, 35(17): 2659-2662 (1994).
Dellaria, Jr., J.F., et al., "Enantioselective Synthesis of α-Amino Acid Derivatives via the Stereoselective Alkylation of a Homochiral Glycine Enolate Synthon," *J Org. Chem.*, 54: 3916-3926 (1989).
Dittert, L.W., et al., "Acetaminophen Prodrugs I-Synthesis, Physicochemical Properties and Analgesic Activity", *J. Pharm. Sci.* 57(5), pp. 774-780 (1968).
Evans, D.A., et al., "Stereoselective Aldol Condensations Via Boron Enolates," *J. Am. Chem. Soc.*, 103: 3099-3111 (1981).
Felding-Habermann, B., et al., "A Ceramide Analog Inhibits T Cell Proliferative Response Through Inhibition of Glycosphingolipid Synthesis and Enhancement of *N,N*-Dimethylsphingosins Synthesis," *Biochemistry*, 29: 6314-6322 (1990).
Gatt, S., et al., "Assay of Enzymes of Lipid Metabolism with Colored and Fluorescent Derivatives of Natural Lipids," *Meth. Enzymol.*, 72: 351-375 (1981).
Hammett, L.P. *Physical Organic Chemistry*, (NY: McGraw), (1940).
Harwood, L.M., et al., "Double diastereocontrol in the synthesis of enantiomerically pure polyoxamic acid," *Chem. Commun.*, 2641-2642 (1998).

(56) References Cited

OTHER PUBLICATIONS

Harwood, L.M., et al., "Asymmetric Cycloadditions of Aldehydes to Stabilized Azomethine Ylids: Enantiocontrolled Construction of β-Hydroxy-α-amino acid Derivitives," *Tetrahedron: Asymmetry*, 3(9): 1127-1130 (1992).

International Search Report for PCT/US2000/018935 dated Nov. 28, 2000.

Hospattankar, A. V., et al., "Changes in Liver Lipids After Administration of 2-Decanoylamino-3-morpholinopropiophenone and Chlorpromazine," *Lipids*, 17(8): 538-543 (1982).

Inokuchi, et al., "Amino Alcohol Esters as Ceramide Analogs and Pharmaceuticals Containing Them for Treatment of Nerve Diseases," Abstract of CAPLUS Accession No. 1998: 786189, JP 10324671 (1998).

Inokuchi, J., et al., "Preparation of the Active Isomer of 1-phenyl-2-decanoylamino-3-morpholino-1-propanol, Inhibitor of Murine Clucocerebroside Synthetase," *Journal of Lipid Research*, 28:565-571 (1987).

Inokuchi, J., et al., "Inhibition of Experimental Metastasis of Murine Lewis Lung Carcinoma by an Inhibitor of Glucosylceramide Synthase and Its Possible Mechanism of Action," *Cancer Research*, 50:6731-6737 (1990).

Inokuchi, et al., (1996): SNT International HCAPLUS database, Columbus (OH), accession No. 1996: 214749.

Jaffrézou, Jr., et al., "Inhibition of Lysosomal Acid Sphingomyelinase by Agents which Reverse Multidrug Resistance," *Biochim. Biophys. Acta*, 1266: 1-8 (1995).

Kalén, A., et al., "Elevated Ceramide Levels in $GH_4C_1$ Cells Treated with Retinoic Acid," *Biochim. Biophys. Acta*, 1125: 90-96 (1992).

Kopaczyk, K., C., et al., "In Vivo Conversions of Cerebroside and Ceramide in Rat Brain," *J. Lipid Res.*, 6: 140-145 (1965).

Kurosawa, M., et al.,"$^{14}$C-Labeling of Novel Atypical β-Adrenoceptor Agonist, SM-11044," *Journal of Labelled Compounds and Radiopharmaceuticals*, 38(3): 285-297 (1996).

Högberg, T. and Ulf Norinder, "Theoretical and Experimental Methods in Drug Design Applied on Antipsychotic Dopamine Antagonists" Textbook of Drug Design and Development, Harwood Academic, pp. 55-91 (1991).

Mitchell, S., et al., "Glycosyltransferase Inhibitors: Synthesis of D-*threo*-PDMP, L-*threo*-PDMP, and Other Brain Glucosylceramide Synthase Inhibitors from D- or L-Serine," *J. Org. Chem.*, 63: 8837-8842 (1998).

Miura, T., et al., "Synthesis and Evaluation of Morpholino and Pyrrolidinosphingolipids as Inhibitors of Glucosylceramide Synthase," *Bioorganic and Medicinal Chemistry*, (6) 1481-1489 (1998).

Nakamura, K., et al., "Coomassie Brilliant Blue Staining of Lipids on Thin-Layer Plates," *Anal. Biochem.*, 142: 406-410 (1984).

Nicolaou, K., et al., "A Practical and Enantioselective Synthesis of Glycosphingolipids and Related Compounds. Total Synthesis of Globotriasylceramide (Gb3)," *J. Am. Chem., Soc.*, 110: 7910-7912 (1988).

Nishida, A., et al., "Practical Synthesis of *threo*-(1S, 2S)-1-Phenyl-2-palmitoylamino-3-morpholino-1-propanol (PPMP) from L-Serine, "*Synlett*, 389-390(1998).

Ogawa, S., et al., "Synthesis and Biological Evaluation of Four Stereoisomers of PDMP-Analogue, N-(2-Decylamino-3-Hydroxy-3-Phenylprop-1-YL)-β-Valienamine, and Related Compounds," *Bioorganic & Medicinal Chemistry Letters*, 7(14):1915-1920 (1997).

Overkleeft, H.S., et al., "Generation of Specific Deoxynojirimycin-type Inhibitors of the Non-lysosomal Glucosylceramidase," *The Journal of Biological Chemistry*, 273(41):26522-26527 (1998).

Preiss, J., et al., "Quantitative Measurement of *sn*-1,2-Diaclglycerols Present in Platelets, Hepatocytes, and *ras*-and *sis*-Transformed Normal Rat Kidney Cells," *J. Biol.Chem.*, 261(19): 8597-8600 (1986).

Radin, N.S., "Killing Cancer Cells by Poly-drug Elevation of Ceramide Levels, A Hypothesis Whose Time has Come:," *Eur. J. Biochem.* 268(2): 193-204 (2001).

Radin, N.S., et al., "Metabolic Effects of Inhibiting Glucosylceramide Synthesis with PDMP and Other Substances."*Advances in Lipid Research: Sphingolipids, Part B.*, R.M. Bell et al., Eds. (San Diego: Academic Press), 26: 183-213 (1993).

Radin, N.S., et al., "Ultrasonic Baths as Substitutes for Shaking Incubator Baths," *Enzyme*, 45: 867-70(1991).

Radin, N.S., et al., "Use of an Inhibitor of Glucosylceramide Synthesis, D-1-Phenyl-2-decanoylamino-3-morpholino-1-propanol," In *NeuroProtocols: A Companion to Methods in Neurosciences*, S.K. Fisher, et al., Eds., (San Diego: Academic Press) 3: 145-155 (1993).

Rosenweld, A.G., et al., "Effects of the Glucosphingolipid Synthesis Inhibitor, PDMP, on Lysosomes in Cultured Cells," *J. Lipid Res.*, 35: 1232-1240 (1994).

Rosenweld, A.G., et al., "Effects of a Sphingolipid Synthesis Inhibitor on Membrane Transport Through the Secretory Pathway," *Biochemistry*, 31: 3581-3590 (1992).

Shayman, J.A., et al., "Glucosphingolipid Dependence of Hormone-Stimulated Inositol Trisphophate Formation," *J. Biol. Chem.*, 265(21): 12135-12138 (1990).

Shayman, J.A., et al., "Modulation of Renal Epithelial Cell Growth by Glucosylceramide," *The Journal of Biological Chemistry*, 266(34):22968-22974 (1991).

Shukla, A., et al., "Metabolism of D-[$^3$H]*threo*-1-phenyl-2-decanoylamino-3-morpholino-1-propanol, an inhibitor of glucosylceramide synthesis and the synergistic action of an inhibitor of microsomal momooxygenase," *J. of Lipid Research*, 32: 713-722 (1991).

Shukla, G.S., et al., "Glucosylceramide Synthase of Mouse Kidney: Further Characterization with an Improved Assay Method," *Arch. Biochem. Biophys.*, 283(2): 372-378 (1990).

Shukla, G., et al., "Rapid Kidney Changes Resulting From Glycosphingolipid Depletion by Treatment with a Glucosyltransferase Inhibitor," *Biochim. Biophys. Acta*, 1083: 101-108 (1991).

Skehan, P., et al., "New Colorimetric Cytotoxicity Assay for Anti-cancer-Drug Screening," *N. Natl. Cancer Inst.*, 82(13): 1107-1112 (1990).

Strum, J.C., et al.,"1-β-D-Arabinofuranosylcytosine Stimulates Ceramide and Diglyceride Formation in HL-60- Cells," *J. Biol. Chem., 269(22)*: 15493-15497 (1994).

Tang, W., et al., "Phorbol Ester Inhibits 13-Cis-Retinoic Acid-Induced Hydrolysis of Phosphatidylinositol 4,5-Biophosphate in cultured Murine Keratinocytes: A Possible Negative Feedback Via Protein Kinase C-Activation," *Cell Bioch. Funct.*, 9: 183-191 (1991).

Uemura, K., et al., "Effect of an Inhibitor of Glucosylceramide Synthesis on Cultured Rabbit Skin Fibroblasts," *J. Biochem.*, (Tokyo) 108(4): 525-530 (1990).

Vunnum, R.,R., et al.., "Analogs of Ceramide That Inhibit Glucocerebroside Synthetase in Mouse Brain," *Chemistry and Physics of Lipids*, LD. Bergelson, et al., eds. (Elsevier/North-Holland Scientific Publishers Ltd.), 26: 265-278 (1980).

Wermuth, C.G., et al.., "Designing Prodrug and Bioprecursors I: Carrier Prodrug", *The Practice of Medicinal Chemistry*, C.G., Wermuth, ed.(CA: Academic Press Limited), pp. 671-696 (1996).

Wong, C-H., et al.., "Synthesis and Evaluation of Homoazasugars as Glycosidase Inhibitors," *J. Org. Chem.*, 60: 1492-1501, (1995).

International Search Report for PCT/US2002/00808 dated Oct. 1, 2002.

International Preliminary Report on Patentability, issued in International Application PCT/US2002/00808, dated Jan. 10, 2003.

International Preliminary Examination Report on Patentability, issued in International Application PCT/US2000/18935 (WO 01/04108) dated Jul. 20, 2001.

European Search Report, European Application No. 09003291.3 dated Apr. 29, 2009.

International Preliminary Report on Patentability for International Application No. PCT/US2002/022659 dated Jul. 24, 2003.

International Search Report for PCT/US2002/022659 dated Nov. 5, 2002.

Adams, L.A., et al., "Nonalcoholic Fatty Liver Disease," *JAMC*, 172(7):899-905 (2005).

Asano, N., "Glycosidase Inhibitors: Update and Perspectives on Practical Use," *Glycobiology*, 13(10):93R-104R (2003).

(56) References Cited

OTHER PUBLICATIONS

Clark, J.M., et al., "Nonalcoholic Fatty Liver Disease, An Under-recognized Caulse of Cryptogenic Cirrhosis," *JAMA*, 289(22):3000-3004 (2003).
Communication from European Patent Office for EP Patent Application No. 05 826 118.1-1216, dated Aug. 13, 2007.
Elbein, A.D., "Glycosidase Inhibitors: Inhibitors of N-linked Oligosaccharide Processing," *The FASEB Journal*, 5:3055-3063 (1991).
Fan, J-G., et al., "Preventie Effects of Metformin on Rats with Non-alcoholic Steatohepatitis," *Hepatology*, 34(4)(1), p. 501A (2003).
Kabayama, K., et al., "TNFα-induced Insulin Resistance in Adipocytes as a Membrane Microdomain Disorder: Involvement of Ganglioside GM3," *Glycobiology*, 15(1):29-29 (2005).
Masson, E., et al., "a-Series Gangliosides Mediate the Effects of Advanced Glycation End Products on Pericyte and Mesangial Cell Proliferation—A Common Mediator for Retinal and Renal Microangiopathy?," *Diabetes*, 54:220-227 (2005).
Sandhoff, K., et al., "Biosynthesis and Degradation of Mammalian Glycosphingolipids," *Phil. Trans. R. Soc. Lond*, B 358:847-861 (2003).
Sasaki, A., et al., "Overexpression of Plasma Membrane-Associated Sialidase Attenuates Insulin Signaling in Transgenic Mice," *The Journal of Biological Chemistry*, 278(30):27896-27902 (2003).
Notification of Transmittal of the International Search Report and Written Opinion of the International Searching Authority from counterpart International Application No. PCT/US2007/068521 dated Nov. 21, 2007.
International Preliminary Report on Patentability issued in International Application PCT/US2007/068521 dated Nov. 11, 2008.
*Notice of Allowance and Fee(s) Due for U.S. Appl. No. 12/227,076; titled: "Methods of Treating Fatty Liver Disease" Date Mailed: Oct. 9, 2012.
*Notice of Allowance and Fee(s) Due for U.S. Appl. No. 13/055,036; titled: "Glucosylceramide Synthase Inhibition for the Treatment of Collapsing Glomerulopathy and Other Glomerular Disease" Date Mailed: Oct. 31, 2012.
Belikov., V.G., "Pharmaceutical Chemistry, Moscow", *Vysshaya Shkola Publishers*, pp. 43-47 (1993).
Natoli, T.A., et al., "Inhibition of glucosylceramide accumulation results in effective blockade of polycystic kidney disease in mouse models" and supplemental information, *Nature Medicine*, 16(7): 788-792 (Jul. 2010).
*Office Action dated May 28, 2013 for U.S. Appl. No. 13/762,102; titled: "Glucosylceramide Synthase Inhibition for the Treatment of Collapsing Glomerulopathy and Other Glomerular Disease".

*Non-Final Office for U.S. Appl. No. 13/193,990, titled "Method of Treating Diabetes Mellitus", dated: Feb. 20, 2014.
*Non-Final Office for U.S. Appl. No. 13/595,349, titled "2-Acylaminopropoanol-Type Glucosylceramide Synthase Inhibitors", dated: Dec. 19, 2013.
*Notice of Allowance and Fee(s) Due for U.S. Appl. No. 12/227,076; titled: "Methods of Treating Fatty Liver Disease" Date Mailed: Jun. 4, 2013.
*Notice of Allowance and Fee(s) Due for U.S. Appl. No. 12/227,076; titled:."Methods of Treating Fatty Liver Disease" Date Mailed: Dec. 23, 2013.
*Notice of Allowance and Fee(s) Due for U.S. Appl. No. 13/762,102; titled: "Glucosylceramide Synthase Inhibition for the Treatment of Collapsing Glomerulopathy and Other Glomerular Disease" Date Mailed: Jan. 9, 2014.
European Search Report for EP Patent Application No. 12007327.5, "Method of Treating Polycystic Kidney Diseases With Ceramide Derivatives" dated Apr. 11, 2013.
European Search Report, European Application No. 13154949.5, "2-Acylaminopropoanol-Type Glucosylceramide Synthase Inhibitors" dated Jul. 12, 2013.
European Search Report, European Application No. 13154955.2, "2-Acylaminopropoanol-Type Glucosylceramide Synthase Inhibitors" dated Jul. 10, 2013.
European Search Report, European Application No. 13154967.7, "2-Acylaminopropoanol-Type Glucosylceramide Synthase Inhibitors" dated Jul. 18, 2013.
European Search Report, European Application No. 13154970.1, "2-Acylaminopropoanol-Type Glucosylceramide Synthesis Inhibitors" dated Jul. 10, 2013.
Husain, A., and Ganem, B., "*syn*-Selective additions to Garner aldehyde: synthesis of a potent glucosylceramide synthase inhibitor", Tetrahedron Letters, 43: 8621-8623 (2002).
Kharkevich, D.A., "Pharmacology", M., Medicament, 47-48 (1987).
Koga, K., and Yamada, S., "Stereochemical Studies. X. Effects of Neighboring Functional Groups on 1,2-Asymmetric Induction in the Reduction of Propiophenone Derivatives with Sodium Borohydride", *Chemical and Pharmaceutical Bulletin*, 20(3): 526-538 (1972).
Yew, N.S., et al., "Increased Hepatic Insulin Action in Diet-Induced Obese Mice Following Inhibition of Glucosylceramide Synthase" PLoS one, 5(6): 1-9 (Jun. 2010).
Zhao, H., et al., "Inhibiting Glycosphingolipid Synthesis Ameliorates Hepatic Steatosis in Obese Mice" Hepatology, pp. 85-93 (Jul. 2009)).

* cited by examiner

METHOD OF TREATING POLYCYSTIC KIDNEY DISEASES WITH CERAMIDE DERIVATIVES

RELATED APPLICATION

This application is the U.S. National Stage of International Application No. PCT/US2008/011450, filed Oct. 3, 2009, which designates the U.S., published in English, and claims the benefit of U.S. Provisional Application No. 60/997,803, filed Oct. 5, 2007. The entire teachings of the above applications are incorporated herein by reference.

BACKGROUND OF THE INVENTION

A cyst is an abnormal fluid-filled sac that can form in many parts of the body, such as the kidney, liver, pancreas, spleen and heart. Polycystic disease is a disease that occurs when a large number of cysts cause damage to these organs. For example, polycystic kidney disease (PKD) is a disease characterized by the growth of numerous cysts throughout the kidneys. The PKD cysts can slowly replace much of the mass of the kidneys, reducing kidney function and leading to kidney failure. About half the people with the most common form of PKD progress to kidney failure and require dialysis or kidney transplantation. PKD can also cause cysts in other organs, most commonly the liver, but also the spleen, pancreas, heart and blood vessels in the brain. About 500,000 people have PKD in this country, and PKD is the fourth leading cause of kidney failure. Autosomal dominant PKD (ADPKD) accounts for about 90% of all PKD cases and about 8-10% of all cases of end stage renal disease. Currently, there is no approved treatment or cure for PKD. Present medical and surgical procedures only reduce the pain resulting from expansion of renal cysts or resolve other symptoms associated with PKD such as infections or high blood pressure. None of these procedures, aside from kidney transplantation, appreciably slows the progression of the disease.

Thus, there is a need for agents and methods for preventing the onset of, or slowing the progression of PKD.

SUMMARY OF THE INVENTION

Applicants have now discovered that certain ceramide derivatives can reduce cystic growth in an animal model for polycystic kidney disease, as measured by kidney/body weight ratio and cyst volume. Based upon this discovery, a method of treating polycystic kidney disease with the ceramide derivatives is disclosed herein.

In one embodiment, the invention is directed to a method of treating polycystic kidney disease in a subject, comprising administering to the subject an effective amount of a compound represented by Structural Formula (1):

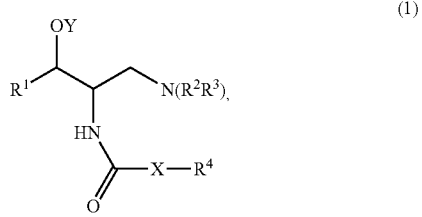

(1)

or a pharmaceutically acceptable salt thereof.

$R^1$ is a substituted or unsubstituted aryl group or a substituted or unsubstituted heteroaryl group.

Y is —H, a hydrolyzable group, or a substituted or unsubstituted alkyl group.

$R^2$ and $R^3$ are each independently —H, a substituted or unsubstituted aliphatic group, a substituted or unsubstituted aryl group, or a substituted or unsubstituted heteroaryl group, or $R^2$ and $R^3$ taken together with the nitrogen atom of $N(R^2R^3)$ form a substituted or unsubstituted non-aromatic heterocyclic ring.

X is a covalent bond; —$(CR^5R^6)_m$—; —$(CR^5R^6)_n$-Q-; —O—; —S—; or —$NR^7$—;

Q is —O—, —S—, —C(O)—, —C(S)—, —C(O)O—, —C(S)O—, —C(S)S—, —C(O)$NR^8$—, —$NR^8$—, —$NR^8$C(O)—, —$NR^8$C(O)$NR^8$—, —OC(O)—, —$SO_3$—, —SO—, —$S(O)_2$—, —$SO_2NR^8$—, or —$NR^8SO_2$—.

When X is —$(CR^5R^6)_m$, $R^4$ is a substituted or unsubstituted aliphatic group, or substituted or unsubstituted aryl group, substituted or unsubstituted heteroaryl group, —CN, —NCS, —$NO_2$ or a halogen.

When X is other than —$(CR^5R^6)_m$, $R^4$ is a substituted or unsubstituted aliphatic group, or substituted or unsubstituted aryl group, or substituted or unsubstituted heteroaryl group.

$R^5$ and $R^6$ are each independently —H, —OH, —SH, a halogen, a substituted or unsubstituted lower alkoxy group, a substituted or unsubstituted lower alkylthio group, or a substituted or unsubstituted lower aliphatic group.

Each $R^7$ is independently —H, a substituted or unsubstituted aliphatic group, a substituted or unsubstituted aryl group, or a substituted or unsubstituted heteroaryl group, or $R^7$ and $R^4$ taken together with the nitrogen atom of $NR^7R^4$ form a substituted or unsubstituted non-aromatic heterocyclic group.

Each $R^8$ is independently —H, a substituted or unsubstituted aliphatic group, a substituted or unsubstituted aryl group, or a substituted or unsubstituted heteroaryl group.

n is 1, 2, 3, 4 or 5, 6, 7, 8, 9, 10, 11, 12, 13, 14 or 15.

m is 1, 2, 3, 4 or 5.

Also, included in the present invention is the use of ceramide derivatives disclosed herein for treating polycystic kidney disease in a subject.

The present invention also includes the use of ceramide derivatives disclosed herein for the manufacture of a medicament for treating a subject having polycystic kidney disease.

The present invention has many advantages. In particular, the present invention provides a treatment for PKD that addresses the underlying disease state, rather than simply ameliorating symptoms that are associated with PKD. Such compounds may reduce the need for kidney dialysis or transplant in patients suffering from PKD.

DETAILED DESCRIPTION OF THE INVENTION

The present invention is directed to a method of treating polycystic kidney disease (PKD) that comprises administering an effective amount of a ceramide derivative disclosed herein to a subject. As shown in Example 4, Applicants have discovered that a certain ceramide derivative can reduce the growth of cyst formation and/or growth in an animal modeled PKD.

In one embodiment, the ceramide derivative is represented by Structural Formula (I), or a pharmaceutically acceptable salt thereof. A first set of values and preferred values for the variables in Structural Formula (I) is provided in the following paragraphs:

Y is —H, a hydrolyzable group, or a substituted or unsubstituted alkyl group. Examples of hydrolyzable groups include —C(O)R, —C(O)OR, —C(O)NRR', C(S)R, —C(S)OR, —C(O)SR or —C(S)NRR'. Specific examples of hydrolyzable groups include an acetyl, —C(=O)(CH$_2$)CH$_3$ and —C(=O)-(1-lower alkyl-1,4-dihydropyridin-4-yl). In a specific embodiment, Y is —H, a hydrolyzable group, or an alkyl group. In another specific embodiment, Y is —H, —C(O)R, —C(O)OR or —C(O)NRR'. In yet another specific embodiment, Y is —H.

X is a covalent bond; —(CR$^5$R$^6$)$_n$-Q-; —O—; —S—; or —NR$^7$—.

Q is —O—, —S—, —C(O)—, —C(S)—, —C(O)O—, —C(S)O—, —C(S)S—, —C(O)NR$^8$—, —NR$^8$—, —NR$^8$C(O)—, —NR$^8$C(O)NR$^8$—, —OC(O)—, —SO$_3$—, —SO—, —S(O)$_2$—, —SO$_2$NR$^8$—, or —NR$^8$SO$_2$—. In a specific embodiment, Q is —O—, —S—, —C(O)—, —C(S)—, —C(O)O—, —C(S)O—, —C(S)S—, —C(O)NR$^8$—, —NR$^8$C(O)NR$^8$—, or —OC(O)—. In yet another specific embodiment, Q is —O—, —S—, —C(O)—, —C(S)—, —NR$^8$(CO)— or —C(O)NR$^8$—. In yet another specific embodiment, Q is —O—, —S—, —C(O)— or —C(S)—. In yet another specific embodiment, Q is —O— or —C(O)—.

R$^1$ is a substituted or unsubstituted aryl group, or a substituted or unsubstituted heteroaryl group. In a specific embodiment, R$^1$ is a substituted or unsubstituted aryl group, such as a substituted or unsubstituted phenyl group. In another specific embodiment, R$^1$ is

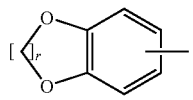

where r is 1, 2, 3 or 4, preferably 1 or 2.

Suitable substituents for each of the aryl and heteroary groups represented by R$^1$ include halogen, alkyl, haloalkyl, Ar$^1$, —OR$^{30}$, —O(haloalkyl), —SR$^{30}$, —NO$_2$, —CN, —NCS, —N(R$^{31}$)$_2$, —NR$^{31}$C(O)R$^{30}$, —NR$^{31}$C(O)OR$^{32}$, —N(R$^{31}$)C(O)N(R$^{31}$)$_2$, —C(O)R$^{30}$, —C(S)R$^{30}$, —C(O)OR$^{30}$, —OC(O)R$^{30}$, —C(O)N(R$^{31}$)$_2$, —S(O)$_2$R$^{30}$, —SO$_2$N(R$^{31}$)$_2$, —S(O)R$^{32}$, —SO$_3$R$^{32}$, —NR$^{31}$SO$_2$N(R$^{31}$)$_2$, —NR$^{31}$SO$_2$R$^{32}$, —V$_o$—Ar$^1$, —V$_o$—OR$^{30}$, —V$_o$—O(haloalkyl), —V$_o$—SR$^{30}$, —V$_o$—NO$_2$, —V$_o$—CN, —V$_o$—N(R$^{31}$)$_2$, —V$_o$—NR$^{31}$C(O)R$^{30}$, —V$_o$—NR$^{31}$CO$_2$R$^{32}$, —V$_o$—N(R$^{31}$)C(O)N(R$^{31}$)$_2$, —V$_o$—C(O)R$^{30}$, —V$_o$—C(S)R$^{30}$, —V$_o$—CO$_2$R$^{30}$, —V$_o$—OC(O)R$^{30}$, —V$_o$—C(O)N(R$^{31}$)$_2$—, —V$_o$—S(O)$_2$R$^{32}$, —V$_o$—SO$_2$N(R$^{31}$)$_2$, —V$_o$—S(O)R$^{32}$, —V$_o$—SO$_3$R$^{32}$, —V$_o$—NR$^{31}$SO$_2$N(R$^{31}$)$_2$, —V$_o$—NR$^{31}$SO$_2$R$^{32}$, —O—V$_o$—Ar$^1$, —O—V$_1$—N(R$^{31}$)$_2$, —S—V$_o$—Ar$^1$, —S—V$_1$—N(R$^{31}$)$_2$, —N(R$^{31}$)—V$_o$—Ar$^1$, —N(R$^{31}$)—V$_1$—N(R$^{31}$)$_2$, —NR$^{31}$C(O)—V$_o$—N(R$^{31}$)$_2$, —NR$^{31}$C(O)—V$_o$—Ar$^1$, —C(O)—V$_o$—N(R$^{31}$)$_2$, —C(O)—V$_o$—Ar$^1$, —C(S)—V$_o$—N(R$^{31}$)$_2$, —C(S)—V$_o$—Ar$^1$, —C(O)O—V$_1$—N(R$^{31}$)$_2$, —C(O)O—V$_o$—Ar$^1$, —O—C(O)—V$_1$—NR$^{31}$)$_2$, —O—C(O)—V$_o$—Ar$^1$, —C(O)N(R$^{31}$)—V$_1$—N(R$^{31}$)$_2$, —C(O)N(R$^{31}$)—V$_o$—Ar$^1$, —S(O)$_2$—V$_o$—N(R$^{31}$)$_2$, —S(O)$_2$—V$_o$—Ar$^1$, —SO$_2$N(R$^{31}$)—V$_1$—N(R$^{31}$)$_2$, —SO$_2$N(R$^{31}$)—V$_o$—Ar$^1$, —S(O)—V$_o$—N(R$^{31}$)$_2$, —S(O)—V$_o$—Ar$^1$, —S(O)$_2$—O—V$_1$—N(R$^{31}$)$_2$, —S(O)$_2$—O—V$_o$—Ar$^1$, —NR$^{31}$SO$_2$—V$_o$—N(R$^{31}$)$_2$, —NR$^{31}$SO$_2$—V$_o$—Ar$^1$, —O—[CH$_2$]$_p$—O—, —S—[CH$_2$]$_p$—S—, or —[CH$_2$]$_q$—. Certain specific substituents for each of the aryl and heteroary groups represented by R$^1$ include halogen, cyano, nitro, alkyl, haloalkyl, —OR$^{30}$, —SR$^{30}$, —N(R$^{31}$)$_2$, Ar$^1$, —V$_o$—OR$^{30}$, —V$_o$—N(R$^{31}$)$_2$, —V$_o$—Ar$^1$, —O—V$_o$—Ar$^1$, —O—V$_1$—N(R$^{31}$)$_2$, —S—V$_o$—Ar$^1$, —S—V$_1$—N(R$^{31}$)$_2$, —N(R$^{31}$)—V$_o$—Ar$^1$, —N(R$^{31}$)—V$_1$—N(R$^{31}$)$_2$, —O—[CH$_2$]$_p$—O—, —S—[CH$_2$]$_p$—S—, or —[CH$_2$]$_q$—. Alternatively, certain specific substituents for each of the aryl and heteroary groups represented by R$^1$ include halogen, cyano, nitro, alkyl, haloalkyl, alkylamino, dialkylamino, aryl, aryloxy, —OH, alkoxy, —O—[CH$_2$]$_p$—O—, and —[CH$_2$]$_q$—. Alternatively, certain specific substituents for each of the aryl and heteroary groups represented by R$^1$ include —OR$^{30}$ (e.g., —OH, —OCH$_3$, —OC$_2$H$_5$), alkyl, (e.g., C1-C6 alkyl), or —O—[CH$_2$]$_p$—O—.

R$^2$ and R$^3$ are each independently —H, a substituted or unsubstituted aliphatic group, a substituted or unsubstituted aryl group or a substituted or unsubstituted heteroaryl group, or R$^2$ and R$^3$ taken together with the nitrogen atom of N(R$^2$R$^3$) form a substituted or unsubstituted non-aromatic heterocyclic ring. In a specific embodiment, R$^2$ and R$^3$ taken together with the nitrogen atom of N(R$^2$R$^3$) form a 5- or 6-membered, optionally-substituted non-aromatic heterocyclic ring. In another specific embodiment, —N(R$^2$R$^3$) is an optionally substituted pyrrolidinyl, azetidinyl, piperidinyl, piperazinyl or morpholinyl group. In another specific embodiment, —N(R$^2$R$^3$) is an unsubstituted pyrrolidinyl, azetidinyl, piperidinyl, piperazinyl or morpholinyl group, preferably an unsubstituted pyrrolidinyl group.

Suitable substituents for the aliphatic, aryl and heteroaryl groups represented by R$^2$ and R$^3$, and suitable substituents for the non-aromatic heterocyclic ring represented by N(R$^2$R$^3$) each independently include halogen, alkyl, haloalkyl, —OR$^{40}$, —O(haloalkyl), —SR$^{40}$, —NO$_2$, —CN, —N(R$^{41}$)$_2$, —NR$^{41}$C(O)R$^{40}$, —NR$^{41}$C(O)OR$^{42}$, —N(R$^{41}$)C(O)N(R$^{41}$)$_2$, —C(O)R$^{40}$, —C(S)R$^{40}$, —C(O)OR$^{40}$, —OC(O)R$^{40}$, —C(O)N(R$^{41}$)$_2$, —S(O)$_2$R$^{42}$, —SO$_2$N(R$^{41}$)$_2$, —S(O)R$^{42}$, —SO$_3$R$^{42}$, Ar$^2$, V$_2$—Ar$^2$, —V$_2$—OR$^{40}$, —V$_2$—O(haloalkyl), —V$_2$—SR$^{40}$, —V$_2$—NO$_2$, —V$_2$—CN, —V$_2$—N(R$^{41}$)$_2$, —V$_2$—NR$^{41}$C(O)R$^{40}$, —V$_2$—NR$^{41}$CO$_2$R$^{42}$, —V$_2$—N(R$^{41}$)C(O)N(R$^{41}$)$_2$, —V$_2$—C(O)R$^{40}$, —V$_2$—C(S)R$^{40}$, —V$_2$—CO$_2$R$^{40}$, —V$_2$—OC(O)R$^{40}$, —V$_2$—C(O)N(R$^{41}$)$_2$—, —V$_2$—S(O)$_2$R$^{42}$, —V$_2$—SO$_2$N(R$^{41}$)$_2$, —V$_2$—S(O)R$^{42}$, —V$_2$—SO$_3$R$^{42}$, —O—V$_2$—Ar$^2$ and —S—V$_2$—Ar$^2$.

Certain specific substituents for the aliphatic, aryl and heteroaryl groups represented by R$^2$ and R$^3$, and for the non-aromatic heterocyclic ring represented by N(R$^2$R$^3$) each independently include halogen, alkyl, haloalkyl, —OR$^{40}$, —O(haloalkyl), —SR$^{40}$, —NO$_2$, —CN, —N(R$^{41}$)$_2$, —C(O)R$^{40}$, —C(S)R$^{40}$, —C(O)OR$^{40}$, —OC(O)R$^{40}$, —C(O)N(R$^{41}$)$_2$, Ar$^2$, V$_2$—Ar$^2$, —V$_2$—OR$^{40}$, —V$_2$—O(haloalkyl), —V$_2$—SR$^{40}$, —V$_2$—NO$_2$, —V$_2$—CN, —V$_2$—N(R$^{41}$)$_2$, —V$_2$—C(O)R$^{40}$, —V$_2$—C(S)R$^{40}$, —V$_2$—CO$_2$R$^{40}$, —V$_2$—OC(O)R$^{40}$, —O—V$_2$—Ar$^2$ and —S—V$_2$—Ar$^2$. Alternatively, certain specific substituents for the aliphatic, aryl and heteroaryl groups represented by R$^2$ and R$^3$, and for the non-aromatic heterocyclic ring represented by N(R$^2$R$^3$) each independently include halogen, C1-C10 alkyl, C1-C10 haloalkyl, —O(C1-C10 alkyl), —O(phenyl), —O(C1-C10 haloalkyl), —S(C1-C10 alkyl), —S(phenyl), —S(C1-C10 haloalkyl), —NO$_2$, —CN, —NH(C1-C10 alkyl), —N(C1-C10 alkyl)$_2$, —NH(C1-C10 haloalkyl), —N(C1-C10 haloalkyl)$_2$, —NH(phenyl), —N(phenyl)$_2$, —C(O)(C1-C10 alkyl), —C(O)(C1-C10 haloalkyl), —C(O)(phenyl), —C(S)(C1-C10 alkyl), —C(S)(C1-C10 haloalkyl), —C(S)(phenyl), —C(O)O(C1-C10 alkyl), —C(O)O(C1-C10 haloalkyl), —C(O)O(phenyl), phenyl, —V$_2$-phenyl, —V$_2$—O-phenyl, —V$_2$—O(C1-C10 alkyl), —V$_2$—O(C1-C10 haloalkyl), —V$_2$—S-phenyl, —V$_2$—S(C1-C10 alkyl), —V$_2$—S(C1-C10 haloalkyl), —V$_2$—NO$_2$, —V$_2$—CN, —V$_2$—NH(C1-C10 alkyl), —V$_2$—N(C1-C10 alkyl)$_2$, —V$_2$—NH(C1-C10 haloalkyl), —$V_2$—N(C1-C10 haloalkyl)$_2$, —$V_2$—NH(phenyl), —$V_2$—N(phenyl)$_2$, —$V_2$—C(O)(C1-C10 alkyl), —$V_2$—C(O)(C1-C10 haloalkyl), —$V_2$—C(O)(phenyl), —$V_2$—C(S)(C1-C10 alkyl), —$V_2$—C(S)(C1-C10 haloalkyl), —$V_2$—C(S)(phenyl), —$V_2$—C(O)O(C1-C10 alkyl), —$V_2$—C(O)O(C1-C10 haloalkyl), —$V_2$—C(O)O(phenyl), —$V_2$—OC(O)(C1-C10 alkyl), —$V_2$—OC(O)(C1-C10 haloalkyl), —$V_2$—OC(O)(phenyl), —O—$V_2$-phenyl and —S—$V_2$-phenyl. Alternatively, certain specific substituents for the aliphatic, aryl and heteroaryl groups represented by $R^2$ and $R^3$, and for the non-aromatic heterocyclic ring represented by $N(R^2R^3)$ each independently include halogen, C1-C5 alkyl, C1-C5 haloalkyl, hydroxy, C1-C5 alkoxy, nitro, cyano, C1-C5 alkoxycarbonyl, C1-C5 alkylcarbonyl, C1-C5 haloalkoxy, amino, C1-C5 alkylamino and C1-C5 dialkylamino.

When X is —$(CR^5R^6)_m$, $R^4$ is a substituted or unsubstituted aliphatic group, or substituted or unsubstituted aryl group, substituted or unsubstituted heteroaryl group, —CN, —NCS, —$NO_2$ or a halogen, or alternatively when X is other than —$(CR^5R^6)_m$, $R^4$ is a substituted or unsubstituted aliphatic group, or substituted or unsubstituted aryl group, or substituted or unsubstituted heteroaryl group. Specifically, $R^4$ is a substituted or unsubstituted aliphatic group, substituted or unsubstituted aryl group, or substituted or unsubstituted heteroaryl group.

In a specific embodiment, $R^4$ is an optionally substituted aliphatic group, such as an optionally substituted alkyl group. In one aspect of this specific embodiment, the optionally substituted aliphatic group, including the optionally substituted alkyl group, is acyclic. In a more specific embodiment, $R^4$ is an alkyl group. In another more specific embodiment, $R^4$ is a C6-C18 alkyl group, such as a C6, C7, C8, C9 or C10 alkyl group. In one aspect of these more specific embodiment, the alkyl group, including the C6, C7, C8, C9 or C10 alkyl group, is acyclic.

In another specific embodiment, $R^4$ is an optionally substituted aryl, an optionally substituted heteroaryl group, or an optionally substituted alkyl group.

In yet another specific embodiment, $R^4$ is an optionally substituted phenyl group or an optionally substituted alkyl group, such as C1-C10 alkyl group, or C6-C8 alkyl group.

In yet another specific embodiment, $R^4$ is an aryl group, a heteroaryl group, a lower arylalkyl group or a lower heteroarylalkyl group, or alternatively, $R^4$ is an optionally substituted aryl or an optionally substituted heteroaryl group. In a more specific embodiment, the aryl, the heteroaryl, the lower arylalkyl and the lower heteroaryl groups represented by $R^4$ are selected from the group consisting of:

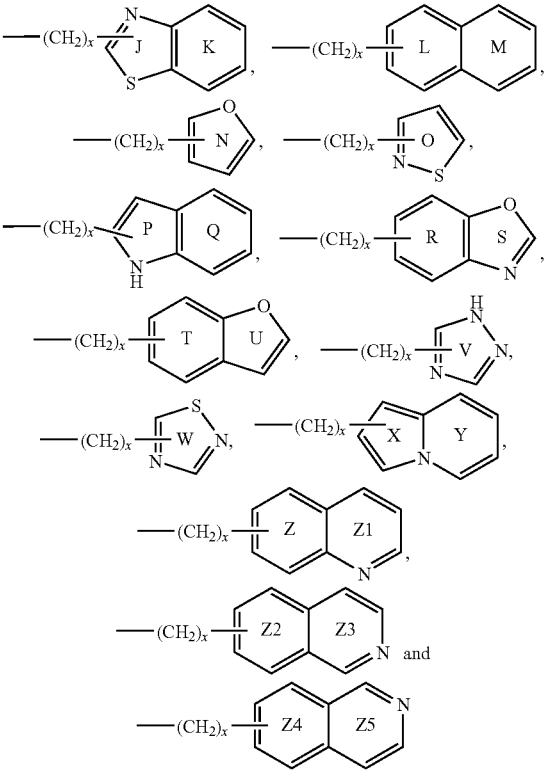

wherein each of rings A-Z5 is optionally and independently substituted; and each x is independently 0 or 1, specifically x is 0. Even more preferably, $R^4$ is an optionally substituted

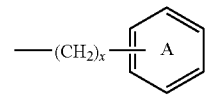

group. Alternatively, $R^4$ is an optionally substituted phenyl group. Alternatively, $R^4$ is an aryl group or a heteroaryl group, each independently optionally substituted with $Ar^3$, such as a phenyl group optionally substituted with $Ar^3$. It is noted that, as shown above, rings A-Z5 can be attached to variable "X" of Structural Formula (I) through —$(CH_2)_x$— at any ring carbon of rings A-Z5 which is not at a position bridging two aryl groups. For example, $R^4$ represented by

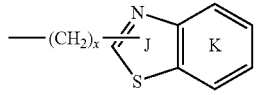

means that $R^4$ is attached to variable "X" through either ring J or ring K.

Suitable substituents for each of the aliphatic, the aryl and the heteroaryl groups represented by $R^4$, including the alkyl group, the arylalkyl, the heteroarylalkyl group and rings A-Z5, include halogen, alkyl, haloalkyl, $Ar^3$, $Ar^3$—$Ar^3$, —$OR^{50}$, —O(haloalkyl), —$SR^{50}$, —$NO_2$, —CN, —NCS, —$N(R^{51})_2$, —$NR^{51}C(O)R^{50}$, —$NR^{51}C(O)OR^{52}$, —$N(R^{51})C(O)N(R^{51})_2$, —$C(O)R^{50}$, —$C(S)R^{50}$, —$C(O)OR^{50}$, —$OC(O)R^{50}$, —$C(O)N(R^{51})_2$, —$S(O)_2R^{52}$, —$SO_2N(R^{51})_2$, —S(O)R$^{52}$, —SO$_3$R$^{52}$, —NR$^{51}$SO$_2$N(R$^{51}$)$_2$, —NR$^{51}$SO$_2$R$^{52}$, —V$_4$—Ar$^3$, —V—OR$^{50}$, —V$_4$—O(haloalkyl), —V$_4$—SR$^{50}$, —V$_4$—NO$_2$, —V$_4$—CN, —V$_4$—N(R$^{51}$)$_2$, —V$_4$—NR$^{51}$C(O)R$^{50}$, —V$_4$—NR$^{51}$CO$_2$R$^{52}$, —V$_4$—N(R$^{51}$)C(O)N(R$^{51}$)$_2$, —V$_4$—C(O)R$^{50}$, —V$_4$—C(S)R$^{50}$, —V$_4$—CO$_2$R$^{50}$, —V$_4$—OC(O)R$^{50}$, —V$_4$—C(O)N(R$^{51}$)$_2$—, —V$_4$—S(O)$_2$R$^{52}$, —V$_4$—SO$_2$N(R$^{51}$)$_2$, —V$_4$—S(O)R$^{52}$, —V$_4$—SO$_3$R$^{52}$, —V$_4$—NR$^{51}$SO$_2$N(R$^{51}$)$_2$, —V$_4$—NR$^{51}$SO$_2$R$^{52}$, —O—V$_4$—Ar$^3$, —O—V$_5$—N(R$^{51}$)$_2$, —S—V$_4$—Ar$^3$, —S—V$_5$—N(R$^{51}$)$_2$, —N(R$^{51}$)—V$_4$—Ar$^3$, —N(R$^{51}$)—V$_5$—N(R$^{51}$)$_2$, —NR$^{51}$C(O)—V$_4$—N(R$^{51}$)$_2$, —NR$^{51}$C(O)—V$_4$—Ar$^3$, —C(O)—V$_4$—N(R$^{51}$)$_2$, —C(O)—V$_4$—Ar$^3$, —C(S)—V$_4$—N(R$^{51}$)$_2$, —C(S)—V$_4$—Ar$^3$, —C(O)O—V$_5$—N(R$^{51}$)$_2$, —C(O)O—V$_4$—Ar$^3$, —O—C(O)—V$_5$—N(R$^{51}$)$_2$, —O—C(O)—V$_4$—Ar$^3$, —C(O)N(R$^{51}$)—V$_5$—N(R$^{51}$)$_2$, —C(O)N(R$^{51}$)—V$_4$—Ar$^3$, —S(O)$_2$—V$_4$—N(R$^{51}$)$_2$, —S(O)$_2$—V$_4$—Ar$^3$, —SO$_2$N(R$^{51}$)—V$_5$—N(R$^{51}$)$_2$, —SO$_2$N(R$^{51}$)—V$_4$—Ar$^3$, —S(O)—V$_4$—N(R$^{51}$)$_2$, —S(O)—V$_4$—Ar$^3$, —S(O)$_2$—O—V$_5$—N(R$^{51}$)$_2$, —S(O)$_2$—O—V$_4$—Ar$^3$, —NR$^{51}$SO$_2$—V$_4$—N(R$^{51}$)$_2$, —NR$^{51}$SO$_2$—V$_4$—Ar$^3$, —O—[CH$_2$]$_{p'}$—O—, —S—[CH$_2$]$_{p'}$—S—, and —[CH$_2$]$_{q'}$—. Certain specific substituents for each of the aliphatic group, the aryl and the heteroaryl groups represented by R$^4$, including the alkyl group, the arylalkyl group, the heteroarylalkyl group and rings A-Z5, include halogen, C1-C10 alkyl, C1-C10 haloalkyl, Ar$^3$, Ar$^3$—Ar$^3$, —OR$^{50}$, —O(haloalkyl), —SR$^{50}$, —NO$_2$, —CN, —N(R$^{51}$)$_2$, —NR$^{51}$C(O)R$^{50}$, —C(O)R$^{50}$, —C(O)OR$^{50}$, —OC(O)R$^{50}$, —C(O)N(R$^{51}$)$_2$, —V$_4$—Ar$^3$, —V—OR$^{50}$, —V$_4$—O(haloalkyl), —V$_4$—SR$^{50}$, —V$_4$—NO$_2$, —V$_4$—CN, —V$_4$—N(R$^{51}$)$_2$, —V$_4$—NR$^{51}$C(O)R$^{50}$, —V$_4$—CO$_2$R$^{50}$, —V$_4$—OC(O)R$^{50}$, —V$_4$—C(O)N(R$^{51}$)$_2$—, —O—V$_4$—Ar$^3$, —O—V$_5$—N(R$^{51}$)$_2$, —S—V$_4$—Ar$^3$, —S—V$_5$—N(R$^{51}$)$_2$, —N(R$^{51}$)—V$_4$—Ar$^3$, —N(R$^{51}$)—V$_5$—N(R$^{51}$)$_2$, —NR$^{51}$C(O)—V$_4$—N(R$^{51}$)$_2$, —NR$^{51}$C(O)—V$_4$—Ar$^3$, —C(O)—V$_4$—N(R$^{51}$)$_2$, —C(O)—V$_4$—Ar$^3$, —C(O)O—V$_5$—N(R$^{51}$)$_2$, —C(O)O—V$_4$—Ar$^3$, —O—C(O)—V$_5$—N(R$^{51}$)$_2$, —O—C(O)—V$_4$—Ar$^3$, —C(O)N(R$^{51}$)—V$_5$—N(R$^{51}$)$_2$, —C(O)N(R$^{51}$)—V$_4$—Ar$^3$, —O—[CH$_2$]$_{p'}$—O— and —[CH$_2$]$_{q'}$—. Alternatively certain specific substituents for each of the aliphatic group, the aryl and the heteroaryl groups represented by R$^4$, including the alkyl group, the arylalkyl group, the heteroarylalkyl group and rings A-Z5, include halogen, cyano, nitro, C1-C10 alkyl, C1-C10 haloalkyl, amino, C1-C10 alkylamino, C1-C10 dialkylamino, —OR$^{50}$, —Ar$^3$, —V$_4$—Ar$^3$, —V—OR$^{50}$, —O(C1-C10 haloalkyl), —V$_4$—O(C1-C10 haloalkyl), —O—V$_4$—Ar$^3$, —O—[CH$_2$]$_p$—O— and —[CH$_2$]$_q$—. Alternatively certain specific substituents for each of the aliphatic group, the aryl and the heteroaryl groups represented by R$^4$, including the alkyl group, the arylalkyl group, the heteroarylalkyl group and rings A-Z5, include halogen, cyano, nitro, C1-C10 alkyl, C1-C10 haloalkyl, amino, C1-C10 alkylamino, C1-C10 dialkylamino, aryl, heteroaryl, aryloxy, heteroaryloxy, hydroxy, C1-10 alkoxy, —O—[CH$_2$]$_p$—O— or —[CH$_2$]$_q$—. Alternatively certain specific substituents for each of the aliphatic group, the aryl and the heteroaryl groups represented by R$^4$, including the alkyl group, the arylalkyl group, the heteroarylalkyl group and rings A-Z5, include halogen, cyano, amino, nitro, Ar$^3$, C1-C6 alkyl, C1-C6 haloalkyl, C1-C6 alkoxy, hydroxy and C1-C6 haloalkoxy. Alternatively certain specific substituents each of the aliphatic group, the aryl and the heteroaryl groups represented by R$^4$, including the alkyl group, the arylalkyl group, the heteroarylalkyl group and rings A-Z5, include —OH, —OCH$_3$, —OC$_2$H$_5$ and —O—[CH$_2$]$_{p'}$—O—. Specifically, when R$^4$ is an optionally substituted phenyl ring A, at least one of the optional substituents of ring A is at the para position.

R$^5$ and R$^6$ are each independently —H, —OH, —SH, a halogen, a substituted or unsubstituted lower alkoxy group, a substituted or unsubstituted lower alkylthio group, or a substituted or unsubstituted lower aliphatic group. Specifically, R$^5$ and R$^6$ are each independently —H; —OH; a halogen; or a lower alkoxy or lower alkyl group. More specifically, R$^5$ and R$^6$ are each independently —H, —OH or a halogen. Even more specifically, R$^5$ and R$^6$ are each independently —H.

Each of R$^7$ and R$^8$ independently is —H, a substituted or unsubstituted aliphatic group, a substituted or unsubstituted aryl group or a substituted or unsubstituted heteroaryl group. Alternatively, R$^7$ and R$^4$ taken together with the nitrogen atom of —NR$^7$R$^4$ form a substituted or unsubstituted non-aromatic heterocyclic group. In some specific embodiments, each of R$^7$ and R$^8$ independently is —H, an optionally substituted aliphatic group or an optionally substituted phenyl group. In some specific embodiments, each of R$^7$ and R$^8$ independently is —H, an optionally substituted alkyl group or an optionally substituted phenyl group. In other specific embodiments, each of R$^7$ and R$^8$ independently is —H or a C1-C6 alkyl group, phenyl or benzyl. Examples of suitable substituents, including specific examples, for the aliphatic, the aryl and the heteroaryl groups represented by each of R$^7$ and R$^8$ independently are as described above for variable R$^4$. Examples of suitable substituents for the non-aromatic heterocyclic group represented by —NR$^7$R$^4$ include halogen, =O, =S, =N(C1-C6 alkyl), C1-C6 alkyl, C1-C6 haloalkyl, hydroxy, C1-C6 alkoxy, nitro, cyano, (C1-C6 alkoxy)carbonyl, (C1-C6 alkyl)carbonyl, C1-C6 haloalkoxy, amino, (C1-C6 alkyl)amino and (C1-C6 dialkyl)amino. Certain specific substituents for the non-aromatic heterocyclic group represented by —NR$^7$R$^4$ include halogen, C1-C6 alkyl, C1-C6 haloalkyl, hydroxy, C1-C6 alkoxy, nitro, cyano, (C1-C6 alkoxy)carbonyl, (C1-C6 alkyl)carbonyl, C1-C6 haloalkoxy, amino, (C1-C6 alkyl)amino and (C1-C6 dialkyl)amino.

n is 1, 2, 3, 4, 5, 6, 7, 8, 9, 10, 11, 12, 13, 14 or 15. Specifically, n is 1, 2, 3, 4, 5, 6, 7, 8, 9 or 10. Alternatively, n is 1, 2, 3, 4, 5 or 6. Alternatively, n is 5, 6, 7, 8, 9 or 10. Alternatively, n is 1, 2, 3 or 4. Alternatively, n is 2, 3, 4 or 5.

m is 1, 2, 3, 4, or 5, specifically 1, 2, 3 or 4.

Each p is independently 1, 2, 3 or 4, specifically 1 or 2.

Each q is independently 3, 4, 5 or 6, specifically 3 or 4.

Each p' is independently 1, 2, 3 or 4, specifically 1 or 2.

Each q' is independently 3, 4, 5 or 6, specifically 3 or 4.

Each V$_o$ is independently a C1-C10 alkylene group, specifically C1-C4 alkylene group.

Each V$_1$ is independently a C2-C10 alkylene group, specifically C2-C4 alkylene group.

Each V$_2$ is independently a C1-C4 alkylene group.

Each V$_4$ is independently a C1-C10 alkylene group, specifically a C1-C4 alkylene group.

Each V$_5$ is independently a C2-C10 alkylene group, specifically a C2-C4 alkylene group.

Each Ar$^1$ is an aryl group or a heteroaryl group, each of which independently is optionally substituted with one or more substituents selected from the group consisting of halogen, alkyl, amino, alkylamino, dialkylamino, alkoxy, nitro, cyano, hydroxy, haloalkoxy and haloalkyl. Specifically, Ar$^1$ is an aryl group or a heteroaryl group, each of which independently is optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl.

More specifically, $Ar^1$ is a phenyl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl.

Each $Ar^2$ is an aryl group or a heteroaryl group, such as a phenyl group, each of which independently is optionally substituted with one or more substituents selected from the group consisting of halogen, C1-C6 alkyl, C1-C6 haloalkyl, hydroxy, C1-C6 alkoxy, nitro, cyano, C1-C6 alkoxycarbonyl, C1-C6 alkylcarbonyl, C1-C6 haloalkoxy, amino, C1-C6 alkylamino and C1-C6 dialkylamino.

Each $Ar^3$ is independently an aryl group or a heteroaryl group, each of which independently is optionally substituted with one or more substituents selected from the group consisting of halogen, alkyl, amino, alkylamino, dialkylamino, alkoxy, nitro, cyano, hydroxy, haloalkoxy and haloalkyl. Specifically, each $Ar^3$ is independently an aryl group or a heteroaryl group, each of which independently is optionally substituted with one or more substituents selected from the group consisting of halogen, C1-C10 alkyl, C1-C10 haloalkyl, hydroxy, C1-C10 alkoxy, nitro, cyano, C1-C10 alkoxycarbonyl, C1-C10 alkylcarbonyl, C1-C10 haloalkoxy, amino, C1-C10 alkylamino and C1-C10 dialkylamino. Even more specifically, each $Ar^3$ is independently an aryl group or a heteroaryl group, each of which independently is optionally substituted with one or more substituents selected from the group consisting of halogen, C1-C4 alkyl, C1-C4 haloalkyl, hydroxy, C1-C4 alkoxy, nitro, cyano, C1-C4 alkoxycarbonyl, C1-C4 alkylcarbonyl, C1-C4 haloalkoxy, amino, C1-C4 alkylamino and C1-C4 dialkylamino.

Each $R^{30}$ is independently i) hydrogen; ii) an aryl group or a heteroaryl group, each of which independently is optionally substituted with one or more substituents selected from the group consisting of halogen, alkyl, amino, alkylamino, dialkylamino, alkoxy, nitro, cyano, hydroxy, haloalkoxy, alkoxycarbonyl, alkylcarbonyl and haloalkyl; or iii) an alkyl group optionally substituted with one or more substituents selected from the group consisting of halogen, amino, alkylamino, dialkylamino, alkoxy, nitro, cyano, hydroxy, haloalkoxy, alkoxycarbonyl and alkylcarbonyl. Specifically, each $R^{30}$ is independently i) hydrogen; ii) an aryl group or a heteroaryl group, each of which independently is optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or iii) a C1-C10 alkyl group optionally substituted with one or more substituents selected from the group consisting of halogen, amino, C1-C6 alkylamino, C1-C1 dialkylamino, C1-C6 alkoxy, nitro, cyano, hydroxy, C1-C6 haloalkoxy, C1-C6 alkoxycarbonyl and C1-C6 alkylcarbonyl. More specifically, each $R^{30}$ is independently i) hydrogen; ii) a phenyl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or iii) a C1-C10 alkyl group optionally substituted with one or more substituents selected from the group consisting of halogen, amino, C1-C6 alkylamino, C1-C1 dialkylamino, C1-C6 alkoxy, nitro, cyano, hydroxy, C1-C6 haloalkoxy, C1-C6 alkoxycarbonyl and C1-C6 alkylcarbonyl.

Each $R^{31}$ is independently $R^{30}$, $—CO_2R^{30}$, $—SO_2R^{30}$ or $—C(O)R^{30}$; or $—N(R^{31})_2$ taken together is an optionally substituted non-aromatic heterocyclic group. In a specific embodiment, each $R^{31}$ is independently $R^{30}$, or $—N(R^{31})_2$ is an optionally substituted non-aromatic heterocyclic group. Suitable substituents for the non-aromatic heterocyclic group represented by $—N(R^{31})_2$ include halogen, $=O$, $=S$, $=N(C1-C6$ alkyl$)$, C1-C6 alkyl, C1-C6 haloalkyl, hydroxy, C1-C6 alkoxy, nitro, cyano, (C1-C6 alkoxy)carbonyl, (C1-C6 alkyl)carbonyl, C1-C6 haloalkoxy, amino, (C1-C6 alkyl)amino and (C1-C6 dialkyl)amino. Certain specific substituents for the non-aromatic heterocyclic group represented by $—N(R^{31})_2$ include halogen, C1-C6 alkyl, C1-C6 haloalkyl, hydroxy, C1-C6 alkoxy, nitro, cyano, (C1-C6 alkoxy)carbonyl, (C1-C6 alkyl)carbonyl, C1-C6 haloalkoxy, amino, (C1-C6 alkyl)amino and (C1-C6 dialkyl)amino.

Each $R^{32}$ is independently i) an aryl group or a heteroaryl group, each of which independently is optionally substituted optionally substituted with one or more substituents selected from the group consisting of halogen, alkyl, amino, alkylamino, dialkylamino, alkoxy, nitro, cyano, hydroxy, haloalkoxy, alkoxycarbonyl, alkylcarbonyl and haloalkyl; or ii) an alkyl group optionally substituted with one or more substituents selected from the group consisting of halogen, amino, alkylamino, dialkylamino, alkoxy, nitro, cyano, hydroxy, haloalkoxy, alkoxycarbonyl and alkylcarbonyl. Specifically, each $R^{32}$ is independently i) an aryl group or a heteroaryl group, each of which independently is optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or ii) a C1-C10 alkyl group optionally substituted with one or more substituents selected from the group consisting of halogen, amino, C1-C6 alkylamino, C1-C1 dialkylamino, C1-C6 alkoxy, nitro, cyano, hydroxy, C1-C6 haloalkoxy, C1-C6 alkoxycarbonyl and C1-C6 alkylcarbonyl. More specifically, each $R^{32}$ is independently i) a phenyl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy and C1-C6 haloalkyl; or ii) a C1-C10 alkyl group optionally substituted with one or more substituents selected from the group consisting of halogen, amino, C1-C6 alkylamino, C1-C1 dialkylamino, C1-C6 alkoxy, nitro, cyano, hydroxy, C1-C6 haloalkoxy, C1-C6 alkoxycarbonyl and C1-C6 alkylcarbonyl.

Each $R^{40}$ is independently i) hydrogen; ii) an aryl group or a heteroaryl group, such as a phenyl group, each of which independently is optionally substituted with one or more substituents selected from the group consisting of halogen, C1-C6 alkyl, C1-C6 haloalkyl, hydroxy, C1-C6 alkoxy, nitro, cyano, C1-C6 alkoxycarbonyl, C1-C6 alkylcarbonyl, C1-C6 haloalkoxy, amino, C1-C6 alkylamino and C1-C6 dialkylamino; or iii) a C1-C10 alkyl group optionally substituted with one or more substituents selected from the group consisting of halogen, C1-C6 haloalkyl, hydroxy, C1-C6 alkoxy, nitro, cyano, C1-C6 alkoxycarbonyl, C1-C6 alkylcarbonyl, C1-C6 haloalkoxy, amino, C1-C6 alkylamino and C1-C6 dialkylamino.

Each $R^{41}$ independently is $R^{40}$, $—CO_2R^{40}$, $—SO_2R^{40}$ or $—C(O)R^{40}$; or $—N(R^{41})_2$ taken together is an optionally substituted non-aromatic heterocyclic group. In a specific embodiment, each $R^{41}$ independently is $R^{40}$, or $—N(R^{41})_2$ is an optionally substituted non-aromatic heterocyclic group. Suitable exemplary substituents, including specific exemplary substituents, for the non-aromatic heterocyclic group represented by —N(R$^{41}$)$_2$ are as described above for the non-aromatic heterocyclic group represented by —N(R$^{31}$)$_2$.

Each R$^{42}$ independently is i) an aryl group or a heteroaryl group, such as a phenyl group, each of which independently is optionally substituted with one or more substituents selected from the group consisting of halogen, C1-C6 alkyl, C1-C6 haloalkyl, hydroxy, C1-C6 alkoxy, nitro, cyano, C1-C6 alkoxycarbonyl, C1-C6 alkylcarbonyl, C1-C6 haloalkoxy, amino, C1-C6 alkylamino and C1-C6 dialkylamino; or ii) a C1-C10 alkyl group optionally substituted with one or more substituents selected from the group consisting of halogen, C1-C6 haloalkyl, hydroxy, C1-C6 alkoxy, nitro, cyano, C1-C6 alkoxycarbonyl, C1-C6 alkylcarbonyl, C1-C6 haloalkoxy, amino, C1-C6 alkylamino and C1-C6 dialkylamino.

Each R$^{50}$ independently is i) hydrogen; ii) an aryl group or a heteroaryl group, such as a phenyl group, each of which independently is optionally substituted with one or more substituents selected from the group consisting of halogen, alkyl, amino, alkylamino, dialkylamino, alkoxy, nitro, cyano, hydroxy, haloalkoxy, alkoxycarbonyl, alkylcarbonyl and haloalkyl; or iii) an alkyl group optionally substituted with one or more substituents selected from the group consisting of halogen, amino, alkylamino, dialkylamino, alkoxy, nitro, cyano, hydroxy, haloalkoxy, alkoxycarbonyl, alkylcarbonyl and haloalkyl. Specifically, each R$^{50}$ is independently i) hydrogen; ii) an aryl group or a heteroaryl group, such as a phenyl group, each of which independently is optionally substituted with one or more substituents selected from the group consisting of halogen, C1-C6 alkyl, C1-C6 haloalkyl, hydroxy, C1-C6 alkoxy, nitro, cyano, C1-C6 alkoxycarbonyl, C1-C6 alkylcarbonyl, C1-C6 haloalkoxy, amino, C1-C6 alkylamino and C1-C6 dialkylamino; or iii) a C1-C10 alkyl group optionally substituted with one or more substituents selected from the group consisting of halogen, C1-C6 haloalkyl, hydroxy, C1-C6 alkoxy, nitro, cyano, C1-C6 alkoxycarbonyl, C1-C6 alkylcarbonyl, C1-C6 haloalkoxy, amino, C1-C6 alkylamino and C1-C6 dialkylamino.

Each R$^{51}$ independently is R$^{50}$, —CO$_2$R$^{50}$, —SO$_2$R$^{50}$ or —C(O)R$^{50}$, or —N(R$^{51}$)$_2$ taken together is an optionally substituted non-aromatic heterocyclic group. In a specific embodiment, each R$^{51}$ independently is R5$^0$, or —N(R$^{51}$)$_2$ is an optionally substituted non-aromatic heterocyclic group. Suitable exemplary substituents, including specific exemplary substituents, for the non-aromatic heterocyclic group represented by —N(R$^{51}$)$_2$ are as described above for the non-aromatic heterocyclic group represented by —N(R$^{31}$)$_2$.

Each R$^{52}$ independently is i) an aryl group or a heteroaryl group, such as a phenyl group, each of which independently is optionally substituted with one or two substituents selected from the group consisting of halogen, alkyl, amino, alkylamino, dialkylamino, alkoxy, nitro, cyano, hydroxy, haloalkoxy, alkoxycarbonyl, alkylcarbonyl and haloalkyl; or ii) an alkyl group optionally substituted with one or more substituents selected from the group consisting of halogen, amino, alkylamino, dialkylamino, alkoxy, nitro, cyano, hydroxy, haloalkoxy, alkoxycarbonyl, alkylcarbonyl and haloalkyl. Specifically, each R$^{52}$ independently is i) an aryl group or a heteroaryl group, such as a phenyl group, each of which independently is optionally substituted with one or more substituents selected from the group consisting of halogen, C1-C6 alkyl, C1-C6 haloalkyl, hydroxy, C1-C6 alkoxy, nitro, cyano, C1-C6 alkoxycarbonyl, C1-C6 alkylcarbonyl, C1-C6 haloalkoxy, amino, C1-C6 alkylamino and C1-C6 dialkylamino; or ii) a C1-C10 alkyl group optionally substituted with one or more substituents selected from the group consisting of halogen, C1-C6 haloalkyl, hydroxy, C1-C6 alkoxy, nitro, cyano, C1-C6 alkoxycarbonyl, C1-C6 alkylcarbonyl, C1-C6 haloalkoxy, amino, C1-C6 alkylamino and C1-C6 dialkylamino.

R and R' are each independently i) —H; ii) a C1-C6 aliphatic group optionally substituted with one or more substituents selected from the group consisting of halogen, —OH, —CN, —NCS, —NO$_2$, —NH$_2$, C1-C6 alkoxy, C1-C6 haloalkoxy, aryl and heteroaryl; or iii) an aryl or a heteroaryl group, each independently and optionally substituted with one or more substituents selected from the group consisting of halogen, —OH, —CN, —NCS, —NO$_2$, —NH$_2$, C1-C6 alkoxy, C1-C6 haloalkoxy, C1-C6 aliphatic group and C1-C6 haloaliphatic group. Alternatively, R and R' taken together with the nitrogen atom of NRR' form a non-aromatic heterocyclic ring optionally substituted with one or more substituents selected from the group consisting of: halogen; —OH; —CN; —NCS; —NO$_2$; —NH$_2$; C1-C6 alkoxy; C1-C6 haloalkoxy; C1-C6 aliphatic group optionally substituted with one or more substituents selected from the group consisting of halogen, —OH, —CN, —NCS, —NO$_2$, —NH$_2$, C1-C6 alkoxy, C1-C6 haloalkoxy, aryl and heteroaryl; and an aryl or a heteroaryl group, each independently and optionally substituted with one or more substituents selected from the group consisting of halogen, —OH, —CN, —NCS, —NO$_2$, —NH$_2$, C1-C6 alkoxy, C1-C6 haloalkoxy, C1-C6 aliphatic group and C1-C6 haloaliphatic group. In a specific embodiment, R and R' are each independently i) —H; ii) a C1-C6 aliphatic group optionally substituted with one or more substituents selected from the group consisting of halogen, —OH, —CN, —NCS, —NO$_2$, —NH$_2$, C1-C6 alkoxy, C1-C6 haloalkoxy, aryl and heteroaryl; or iii) a phenyl group optionally substituted with one or more substituents selected from the group consisting of halogen, —OH, —CN, —NCS, —NO$_2$, —NH$_2$, C1-C6 alkoxy, C1-C6 haloalkoxy, C1-C6 aliphatic group and C1-C6 haloaliphatic group. Alternatively, R and R' taken together with the nitrogen atom of NRR' form a non-aromatic heterocyclic ring optionally substituted with one or more substituents selected from the group consisting of: halogen; —OH; —CN; —NCS; —NO$_2$; —NH$_2$; C1-C6 alkoxy; C1-C6 haloalkoxy; C1-C6 aliphatic group optionally substituted with one or more substituents selected from the group consisting of halogen, —OH, —CN, —NCS, —NO$_2$, —NH$_2$, C1-C6 alkoxy, C1-C6 haloalkoxy, aryl and heteroaryl; and a phenyl group optionally substituted with one or more substituents selected from the group consisting of halogen, —OH, —CN, —NCS, —NO$_2$, —NH$_2$, C1-C6 alkoxy, C1-C6 haloalkoxy, C1-C6 aliphatic group and C1-C6 haloaliphatic group. In another specific embodiment, R and R' are each independently —H; a C1-C6 aliphatic group optionally substituted with one or more substituents selected from the group consisting of halogen, phenyl, hydroxy, C1-C4 alkoxy, C1-C4 haloalkoxy and benzyl; phenyl; or benzyl. Specific examples of each R and R' include —H, C1-C4 alkyl, phenyl and benzyl.

A second set of values for the variables in Structural Formula (I) is provided in the following paragraphs:

Y is —H, —C(O)R, —C(O)OR or —C(O)NRR', preferably —H.

R$^1$ is an optionally substituted aryl group or an optionally substituted heteroaryl group. Examples of suitable substituents, including specific substituents, for the aryl and the heteroaryl groups represented by R$^1$ are as described in the first set of values for the variables of Structural Formula (I).

R$^2$ and R$^3$ taken together with the nitrogen atom of N(R$^2$R$^3$) form a 5- or 6-membered, optionally-substituted non-aromatic heterocyclic ring. Examples of suitable substituents, including specific substituents, for the non-aromatic heterocyclic ring represented by —NR²R³ are as described in the first set of values for the variables of Structural Formula (I).

Values and preferred values for the remainder of the variables of Structural Formula (I) are each independently as described above for the first set of values.

A third set of values for the variables in Structural Formula (I) is provided in the following paragraphs:

Y is —H, —C(O)R, —C(O)OR or —C(O)NRR', preferably —H.

R¹ is an optionally substituted aryl group or an optionally substituted heteroaryl group. Examples of suitable substituents, including specific substituents, for the aryl and the heteroaryl groups represented by R¹ are as described in the first set of values for the variables of Structural Formula (I).

R² and R³ taken together with the nitrogen atom of N(R²R³) form a 5- or 6-membered, optionally-substituted non-aromatic heterocyclic ring. Examples of suitable substituents, including specific substituents, for the non-aromatic heterocyclic ring represented by —NR²R³ are as described in the first set of values for the variables of Structural Formula (I).

R⁵ and R⁶ are each independently —H, —OH, a halogen, a lower alkoxy group or a lower alkyl group.

Values and preferred values of the remainder of the variables of Structural Formula (I) are each independently as described above for the first set of values.

A fourth set of values for the variables in Structural Formula (I) is provided in the following paragraphs:

Each of Y, R¹, R², R³, R⁵ and R⁶ independently is as described above for the third set of values.

X is —(CR⁵R⁶)ₙ-Q-; Q is —O—, —S—, —C(O)—, —C(S)—, —C(O)O—, —C(S)O—, —C(S)S—, —C(O)NR⁸—, —NR⁸—, —NR⁸C(O)—, —NR⁸C(O)NR⁸—, —OC(O)—, —SO₃—, —SO—, —S(O)₂—, —SO₂NR⁸—, or —NR⁸SO₂—; and R⁴ is —H, a substituted or unsubstituted aliphatic group, a substituted or unsubstituted aryl group, or a substituted or unsubstituted heteroaryl group. Alternatively, X is —O—, —S— or —NR⁷—; and R⁴ is a substituted or unsubstituted aliphatic group, a substituted or unsubstituted aryl group, or a substituted or unsubstituted heteroaryl group. Alternatively, X is —(CR⁵R⁶)ₘ—; and R⁴ is a substituted or unsubstituted cyclic alkyl group, or a substituted or unsubstituted cyclic alkenyl group, a substituted or unsubstituted aryl group, or a substituted or unsubstituted heteroaryl group, —CN, —NCS, —NO₂ or a halogen. Alternatively, X is a covalent bond; and R⁴ is a substituted or unsubstituted aryl group or a substituted or unsubstituted heteroaryl group.

n is 1, 2, 3, 4, 5 or 6.

Values and preferred values of the remainder of the variables of Structural Formula (I) are each independently as described above for the first set of values.

In a second embodiment, the ceramide derivative is represented by Structural Formula (II), (III), (IV), (V), (VI), (VII), (VIII), (IX), (X), (XI), (XII), (XIII) or (XIV):

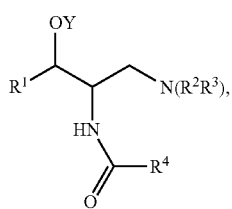

(II)

-continued

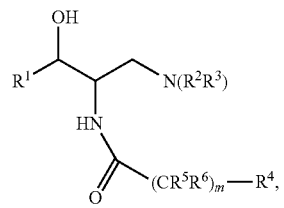

(III)

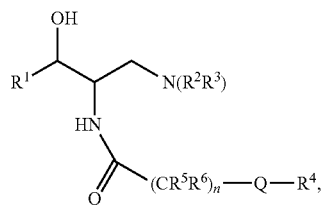

(IV)

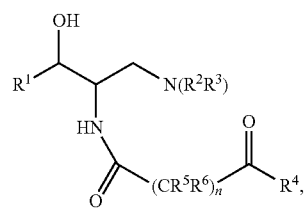

(V)

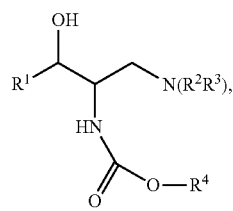

(VI)

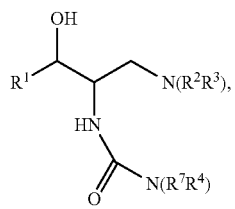

(VII)

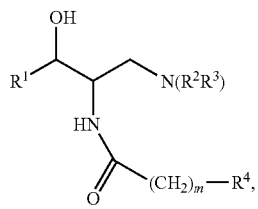

(VIII)

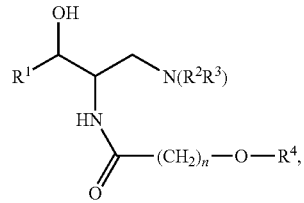

(IX)

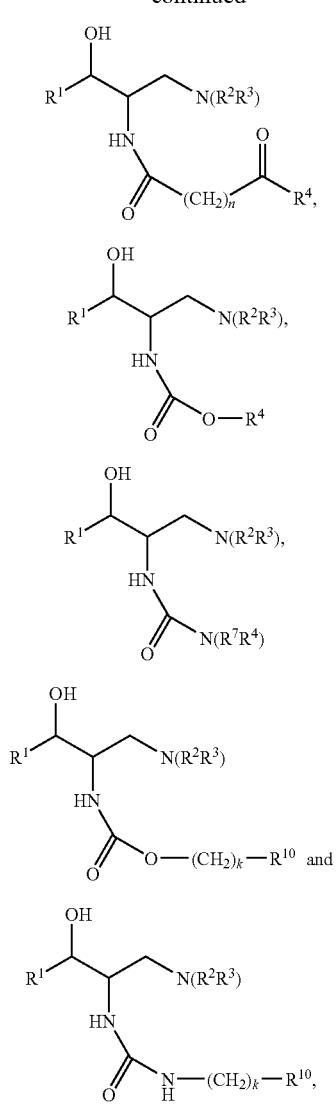

or a pharmaceutically acceptable salt thereof. A first set of values for the variables of Structural Formulas (II)-(XIV) is provided in the following paragraphs:

Y in Structural Formula (II) is —H, —C(O)R, —C(O)OR or —C(O)NRR', preferably —H.

$R^1$ is an optionally substituted aryl group or an optionally substituted heteroaryl group. Examples of suitable substituents, including specific substituents, for the aryl and the heteroaryl groups represented by $R^1$ are as described in the first set of values for the variables of Structural Formula (I).

$R^2$ and $R^3$ taken together with the nitrogen atom of $N(R^2R^3)$ form a 5- or 6-membered, optionally-substituted non-aromatic heterocyclic ring. Examples of suitable substituents, including specific substituents, for the non-aromatic heterocyclic ring represented by —$NR^2R^3$ are as described in the first set of values for the variables of Structural Formula (I).

For Structural Formula (II), in one specific embodiment, $R^4$ is an optionally substituted aliphatic group. In another specific embodiment, $R^4$ is an optionally substituted aliphatic group, an optionally substituted aryl group, an optionally substituted heteroaryl group, —CN, —NCS, —$NO_2$ or a halogen. In one further aspect of this another specific embodiment, $R^4$ is an optionally substituted aryl group or an optionally substituted heteroaryl group. Examples of suitable substituents, including specific substituents, for the aliphatic, the aryl and the heteroaryl groups represented by $R^4$ are as described in the first set of values for the variables of Structural Formula (I).

Each $R^4$ in Structural Formulas (IV), (V), (VI), (VII), (X), (XI) and (XII) is independently an optionally substituted aliphatic group, an optionally substituted aryl group or an optionally substituted heteroaryl group. Specifically, for Structural Formulas (VI) and (VII), each $R^4$ independently is an optionally substituted aryl group, an optionally substituted heteroaryl group, an optionally substituted lower arylalkyl group or an optionally substituted heteroarylalkyl group. Examples of suitable substituents, including specific substituents, for the aliphatic, the aryl and the heteroaryl groups represented by $R^4$ are as described in the first set of values for the variables of Structural Formula (I).

Each of $R^5$ and $R^6$ in Structural Formulas (III), (IV) and (V) are each independently —H, —OH, a halogen, a C1-C6 alkoxy group or a C1-C6 alkyl group.

Each $R^4$ in Structural Formulas (III) and (VIII) independently is an optionally substituted cyclic alkyl (e.g., C3-C8) group, an optionally substituted cyclic alkenyl (e.g., C3-C8) group, an optionally substituted aryl group, or an optionally substituted heteroaryl group, —CN, —NCS, —$NO_2$ or a halogen. Specifically, $R^4$ is an optionally substituted aryl group or an optionally substituted heteroaryl group. Examples of suitable substituents, including specific substituents, for the alkyl, the alkenyl, the aryl and the heteroaryl groups represented by $R^4$ are as described in the first set of values for the variables of Structural Formula (I).

Each $R^7$ in Structural Formulas (VII) and (XII) is independently —H or C1-C6 alkyl.

For Structural Formula (IV), values and preferred values of each of Q and $R^8$ independently are as described above in the first set of values for Structural Formula (I). In a specific embodiment of Structural Formula (IV), Q is —O—, —S—, —C(O)—, —C(S)—, —C(O)O—, —C(S)O—, —C(S)S—, —$NR^8$(CO)—, —C(O)$NR^8$— or —OC(O)—; and $R^8$ is optionally —H, an optionally substituted aliphatic group, an optionally substituted aryl group or an optionally substituted heteroaryl group. In another specific embodiment of Structural Formula (IV), Q is —O—, —S—, —C(O)—, —C(S)—, —C(O)O—, —C(S)O—, —C(S)S—, —$NR^8$(CO)—, —C(O)$NR^8$— or —OC(O)—; and $R^8$ is optionally —H, an optionally substituted aliphatic group or an optionally substituted phenyl group. In yet another specific embodiment of Structural Formula (IV), Q is —O—, —S—, —C(O)—, —C(S)—, —$NR^8$(CO)— or —C(O)$NR^8$—; and $R^8$ is optionally —H, an optionally substituted aliphatic group, an optionally substituted aryl group or an optionally substituted heteroaryl group. In yet another specific embodiment of Structural Formula (IV), Q is —O—, —S—, —C(O)—, —C(S)—, —$NR^8$(CO)— or —C(O)$NR^8$—; and $R^8$ is optionally —H, an optionally substituted aliphatic group or an optionally substituted phenyl group. In yet another specific embodiment of Structural Formula (IV), Q is —O—, —S—, —C(O)—, —C(S)—, —$NR^8$(CO)— or —C(O)$NR^8$—; and $R^8$ is optionally —H, an optionally substituted aliphatic group or an optionally substituted phenyl group; and $R^8$ is —H or a C1-C6 alkyl group, phenyl or benzyl. Examples of suitable substituents, including specific substituents, for the alkyl, the alkenyl, the aryl and the heteroaryl groups represented by $R^8$ are as described in the first set of values for the variables of Structural Formula (I).

Each $R^{10}$ in Structural Formulas (XIII) and (XIV) independently is i) —H; ii) an aryl group or a heteroaryl group, each independently optionally substituted with one or more substituents selected from the group consisting of halogen, alkyl, amino, alkylamino, dialkylamino, alkoxy, nitro, cyano, hydroxy, haloalkoxy, and haloalkyl; or iii) a C1-C6 alkyl group each optionally and independently substituted with one or more substituents selected from the group consisting of with one or more substituents selected from the group consisting of halogen, cyano, nitro, C1-C10 alkyl, C1-C10 haloalkyl, amino, C1-C10 alkylamino, C1-C10 dialkylamino, aryl, heteroaryl, aryloxy, heteroaryloxy, hydroxy, C1-10 alkoxy, —O—[CH$_2$]$_p$—O— or —[CH$_2$]$_q$—.

Each k in Structural Formulas (XIII) and (XIV) independently is 1, 2, 3, 4, 5 or 6.

Each n in Structural Formulas (IV) and (V) independently is 1, 2, 3, 4, 5 or 6.

Values and preferred values of the remainder of the variables of Structural Formulas (II)-(XIV) are each independently as described above in the first set of values for Structural Formula (I).

A second set of values for the variables of Structural Formulas (II)-(XIV) is provided in the following paragraphs:

Each of Y, Q, $R^2$, $R^3$, $R^4$, $R^5$, $R^6$, $R^7$, $R^8$ and $R^{10}$ independently is as described above for the first set of values for the variables of Structural Formulas (II)-(XIV).

$R^1$ is a phenyl group optionally substituted with one or more substituents selected from the group consisting of halogen, cyano, nitro, alkyl, haloalkyl, —OR$^{30}$, —SR$^{30}$, —N(R$^{31}$)$_2$, Ar$^1$, —V$_o$—OR$^{30}$, —V$_o$—N(R$^{31}$)$_2$, —V$_o$—Ar$^1$, —O—V$_o$—Ar$^1$, —O—V$_1$—N(R$^{31}$)$_2$, —S—V$_o$—Ar$^1$, —S—V$_1$—N(R$^{31}$)$_2$, —N(R$^{31}$)—V$_o$—Ar$^1$, —N(R$^{31}$)—V$_1$—N(R$^{31}$)$_2$, —O—[CH$_2$]$_p$—O—, —S—[CH$_2$]$_p$—S—, or —[CH$_2$]$_q$—. Specifically, $R^1$ is a phenyl group optionally substituted with one or more substituents selected from the group consisting of halogen, cyano, nitro, alkyl, haloalkyl, alkylamino, dialkylamino, aryl, aryloxy, —OH, alkoxy, —O—[CH$_2$]$_p$—O— and —[CH$_2$]$_q$—. Specifically, the "alkyl" referred to in the alkyl, alkoxy, haloalkyl, alkylamino and dialkylamino groups of the exemplary substituents independently is C1-C6 alkyl.

Ar$^1$ is a phenyl group each optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl. Preferably, Ar$^1$ is a phenyl group each optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl.

Each $R^{30}$ is independently i) hydrogen; ii) a phenyl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or iii) a C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl and C1-C6 haloalkyl.

Each $R^{31}$ is independently $R^{30}$, or —N(R$^{31}$)$_2$ is an optionally substituted non-aromatic heterocyclic group. Examples of suitable substituents, including specific substituents, for the non-aromatic heterocyclic ring represented by —NR$^2$R$^3$ are as described in the first set of values for the variables of Structural Formula (I).

Values and preferred values of the remainder of the variables of Structural Formulas (II)-(XIV) are each independently as described above in the first set of values for Structural Formula (I).

A third set of values for the variables in Structural Formulas (II)-(XIV) is provided in the following paragraphs:

Each of Y, Q, $R^1$, $R^4$, $R^5$, $R^6$, $R^7$, $R^8$, $R^{10}$, $R^{30}$, $R^{31}$ and Ar$^1$ independently is as described above for the second set of values for the variables of Structural Formulas (II)-(XIV).

Each —N(R$^2$R$^3$) is a pyrrolidinyl, azetidinyl, piperidinyl, piperazinyl or morpholinyl group optionally substituted with one or more substituents selected from the group consisting of halogen, C1-C5 alkyl, C1-C5 haloalkyl, hydroxyl, C1-C5 alkoxy, nitro, cyano, C1-C5 alkoxycarbonyl, C1-C5 alkylcarbonyl or C1-C5 haloalkoxy, amino, C1-C5 alkylamino and C1-C5 dialkylamino.

Values and preferred values of the remainder of the variables of Structural Formulas (II)-(XIV) are each independently as described above in the first set of values for Structural Formula (I).

A fourth set of values for the variables in Structural Formulas (II)-(XIV) is provided in the following paragraphs:

Each of Y, Q, $R^1$, $R^4$, $R^5$, $R^6$, $R^7$, $R^8$, $R^{10}$, $R^{30}$, $R^{31}$ and Ar$^1$ independently is as described above for the third set of values for values for the variables of Structural Formulas (II)-(XIV).

Each —N(R$^2$R$^3$) is an unsubstituted pyrrolidinyl, azetidinyl, piperidinyl, piperazinyl or morpholinyl group.

Values and preferred values of the remainder of the variables of Structural Formulas (II)-(XIV) are each independently as described above in the first set of values for Structural Formula (I).

A fifth set of values for the variables in Structural Formulas (II)-(XIII) is provided in the following paragraphs:

Each of Y, Q, $R^2$, $R^3$, $R^4$, $R^5$, $R^6$, $R^7$, $R^8$, $R^{10}$, $R^{30}$, $R^{31}$ and Ar$^1$ independently is as described above for the fourth set of values for the variables of Structural Formulas (II)-(XIV).

$R^1$ is a phenyl group optionally substituted with one or more substituents selected from the group consisting of —OR$^{30}$ (e.g., —OH, —OCH$_3$, —OC$_2$H$_5$), alkyl (e.g., C1-C10 alkyl) and —O—[CH$_2$]$_p$—O—. Specifically, $R^1$ is 4-hydroxyphenyl or 3,4-ethylenedioxy-1-phenyl.

Values and preferred values of the remainder of the variables of Structural Formulas (II)-(XIV) are each independently as described above in the first set of values for Structural Formula (I).

A sixth set of values for the variables in Structural Formulas (II)-(XIV) is provided in the following paragraphs:

Each of Y, Q, $R^1$, $R^2$, $R^3$, $R^5$, $R^6$, $R^7$, $R^8$, $R^{10}$, $R^{30}$, $R^{31}$ and Ar$^1$ independently is as described above for the fifth set of values for the variables of Structural Formulas (II)-(XIV).

Each $R^4$ for Structural Formulas (II), (IV)-(VII), (IX) and (X) is independently i) an aryl group or a heteroaryl group, each of which independently is optionally substituted with one or more substituents selected from the group consisting of halogen, cyano, nitro, alkyl, haloalkyl, amino, alkylamino, dialkylamino, —OR$^{50}$, —Ar$^3$, —V$_4$—Ar$^3$, —V—OR$^{50}$, —O(haloalkyl), —V$_4$—O(haloalkyl), —O—V$_4$—Ar$^3$, —O—[CH$_2$]$_{p'}$—O— and —[CH$_2$]$_{q'}$—; or ii) an aliphatic group optionally substituted with one or more substituents selected from the group consisting of halogen, cyano, nitro, haloalkyl, amino, alkylamino, dialkylamino, —OR$^{50}$, —Ar$^3$, —V$_4$—Ar$^3$, —V—OR$^{50}$, —O(haloalkyl), —V$_4$—O(haloalkyl), —O—V$_4$—Ar$^3$, —O—[CH$_2$]$_{p'}$—O— and —[CH$_2$]$_{q'}$—.

Each $R^4$ for Structural Formulas (XI) and (XII) is independently an aryl group, a heteroaryl group, a lower arylalkyl group or a lower heteroaryl group, each of which independently is optionally substituted with one or more substituents selected from the group consisting of halogen, alkyl, haloalkyl, $Ar^3$, —$OR^{50}$, —O(haloalkyl), —$SR^{50}$, —$NO_2$, —CN, —$N(R^{51})_2$, —$NR^{51}C(O)R^{50}$, —$C(O)R^{50}$, —$C(O)OR^{50}$, —$OC(O)R^{50}$, —$C(O)N(R^{51})_2$, —$V_4$—$Ar^3$, —V—$OR^{50}$, —$V_4$—O(haloalkyl), —$V_4$—$SR^{50}$, —$V_4$—$NO_2$, —$V_4$—CN, —$V_4$—$N(R^{51})_2$, —$V_4$—$NR^{51}C(O)R^{50}$, —$V_4$—$C(O)R^{50}$, —$V_4$—$CO_2R^{50}$, —$V_4$—$OC(O)R^{50}$, —$V_4$—$C(O)N(R^{51})_2$—, —O—$V_4$—$Ar^3$, —O—$V_5$—$N(R^{51})_2$, —S—$V_4$—$Ar^3$, —S—$V_5$—$N(R^{51})_2$, —$N(R^{51})$—$V_4$—$Ar^3$, —$N(R^{51})$—$V_5$—$N(R^{51})_2$, —$NR^{51}C(O)$—$V_4$—$N(R^{51})_2$, —$NR^{51}C(O)$—$V_4$—$Ar^3$, —$C(O)$—$V_4$—$N(R^{51})_2$, —$C(O)$—$V_4$—$Ar^3$, —$C(O)O$—$V_5$—$N(R^{51})_2$, —$C(O)O$—$V_4$—$Ar^3$, —O—$C(O)$—$V_5$—$N(R^{51})_2$, —O—$C(O)$—$V_4$—$Ar^3$, —$C(O)N(R^{51})$—$V_5$—$N(R^{51})_2$, —$C(O)N(R^{51})$—$V_4$—$Ar^3$, —O—$[CH_2]_{p'}$—O— and —$[CH_2]_{q'}$—. Specifically, $R^4$ is an optionally substituted aryl or an optionally substituted heteroaryl group, each optionally substituted with one or more substituents selected from the group consisting of halogen, cyano, nitro, alkyl, haloalkyl, amino, alkylamino, dialkylamino, —$OR^{50}$, —$Ar^3$, —$V_4$—$Ar^3$, —V—$OR^{50}$, —O(haloalkyl), —$V_4$—O(haloalkyl), —O—$V_4$—$Ar^3$, —O—$[CH_2]_{p'}$—O— and —$[CH_2]_{q'}$—.

Each $R^4$ for Structural Formulas (III) and (VIII) independently is an aryl group or a heteroaryl group, each of which independently is optionally substituted with one or more substituents selected from the group consisting of halogen, cyano, nitro, alkyl, haloalkyl, amino, alkylamino, dialkylamino, —$OR^{50}$, —$Ar^3$, —$V_4$—$Ar^3$, —V—$OR^{50}$, —O(haloalkyl), —$V_4$—O(haloalkyl), —O—$V_4$—$Ar^3$, —O—$[CH_2]_{p'}$—O— and —$[CH_2]_{q'}$—.

Values and preferred values of the remainder of the variables of Structural Formulas (II)-(XIV) are each independently as described above in the first set of values for Structural Formula (I).

A seventh set of values for the variables in Structural Formulas (II)-(XIV) is provided in the following paragraphs:

Each of Y, Q, $R^1$, $R^2$, $R^3$, $R^4$, $R^5$, $R^6$, $R^7$, $R^8$, $R^{10}$, $R^{30}$, $R^{31}$ and $Ar^1$ independently is as described above for the sixth set of values for the variables of Structural Formulas (II)-(XIV).

Each $Ar^3$ is independently a phenyl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl.

Each $R^{50}$ is independently i) hydrogen; ii) a phenyl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or iii) an C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl.

Values and preferred values of the remainder of the variables of Structural Formulas (II)-(XIV) are each independently as described above in the first set of values for Structural Formula (I).

An eighth set of values for the variables in Structural Formulas (II)-(XIV) is provided in the following paragraphs:

Each of Y, Q, $R^1$, $R^2$, $R^3$, $R^5$, $R^6$, $R^7$, $R^8$, $R^{10}$, $R^{30}$, $R^{31}$, $R^{50}$, $Ar^1$ and $Ar^3$ independently is as described above for the seventh set of values for the variables of Structural Formulas (II)-(XIV).

Each —$N(R^2R^3)$ is independently N-pyrrolidinyl or N-morpholinyl.

$R^4$ for Structural Formula (II) is an aliphatic group. Specifically, $R^4$ is a C6-C18 alkyl group or a C6-C8 alkyl group (e.g., C6, C7, C8, C9 or C10 alkyl group).

Each $R^4$ for Structural Formulas (IX) and (X) is independently an alkyl group, or an optionally substituted phenyl group. Specifically, each $R^4$ is an unsubstituted alkyl group (e.g., C1-C10 alkyl), or a phenyl group optionally substituted with one or more substituents selected from the group consisting of —OH, —$OCH_3$ and —$OC_2H_5$.

Each $R^4$ for Structural Formulas (XI) and (XII) is an optionally substituted aryl or an optionally substituted heteroaryl group, each optionally substituted with one or more substituents selected from the group consisting of halogen, cyano, nitro, alkyl, haloalkyl, amino, alkylamino, dialkylamino, —$OR^{50}$, —$Ar^3$, —$V_4$—$Ar^3$, —V—$OR^{50}$, —O(haloalkyl), —$V_4$—O(haloalkyl), —O—$V_4$—$Ar^3$, —O—$[CH_2]_{p'}$—O— and —$[CH_2]_{q'}$—. Specifically, the "alkyl" referred to in the alkyl, alkoxy, haloalkyl, alkylamino and dialkylamino groups of the exemplary substituents independently is C1-C10 alkyl, or, alternatively, C1-C6 alkyl.

$R^4$ for Structural Formula (III) or (VIII) is a biaryl group optionally substituted with one or more substituents selected from the group consisting of halogen, cyano, amino, nitro, $Ar^3$, alkyl, haloalkyl, alkoxy, hydroxy and haloalkoxy. Specifically, the optionally substituted biaryl group is an optionally substituted biphenyl group. Alternatively, —$(CH_2)_n$—$R^8$ is

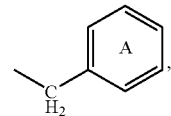

wherein phenyl ring A is optionally substituted with one or more substituents selected from the group consisting of halogen, cyano, amino, nitro, $Ar^3$, alkyl, haloalkyl, alkoxy, hydroxy and haloalkoxy.

Each $R^{10}$ for Structural Formulas (XIII) and (XIV) is independently a C1-C6 alkyl group; an optionally substituted phenyl group; or an optionally substituted, monocyclic or bicyclic heteroaryl group. Suitable substituents, including specific substituents, for each of the alkyl, phenyl and the heteroaryl groups are as described in the first set of values for $R^4$ of Structural Formula (I). Specifically, exemplary substituents for each of the alkyl, phenyl and the heteroaryl groups are as described above in the seventh set of values for $R^8$ for Structural Formulas (XIII) and (XIV).

For Structural Formulas (III) and (VIII), m is 1, 2 or 3.

For Structural Formulas (IX) and (X), each n is independently 1, 2, 3, 4 or 5. Specifically, for Structural Formula (IX), n is 1, 2, 3 or 4. Specifically, for Structural Formula (X), n is 3, 4 or 5.

Values and preferred values of the remainder of the variables of Structural Formulas (II)-(XIV) are each independently as described above in the first set of values for Structural Formula (I).

In a ninth set, values and preferred values of each of Y, Q, $R^1$, $R^2$, $R^3$, $R^4$, $R^5$, $R^6$, $R^7$, $R^8$, $R^{30}$, $R^{31}$, $R^{32}$, $R^{40}$, $R^{41}$, $R^{42}$, $R^{50}$, $R^{51}$, $R^{52}$, $Ar^1$, $Ar^2$, and $Ar^3$ of Structural Formulas (II)-

(XIV) independently are as described above for the first set, second set, third set or fourth set of values for the variables of Structural Formula (I). Values and preferred values of the remaining variables of Structural Formulas (II)-(XIV) each independently are as described above for the first set, second set, third set, fourth set, fifth set, six set, seventh set or an eighth set of values for the variables of Structural Formulas (II)-(XIV).

Certain specific examples of ceramide derivatives that can be employed in the invention are as follows:

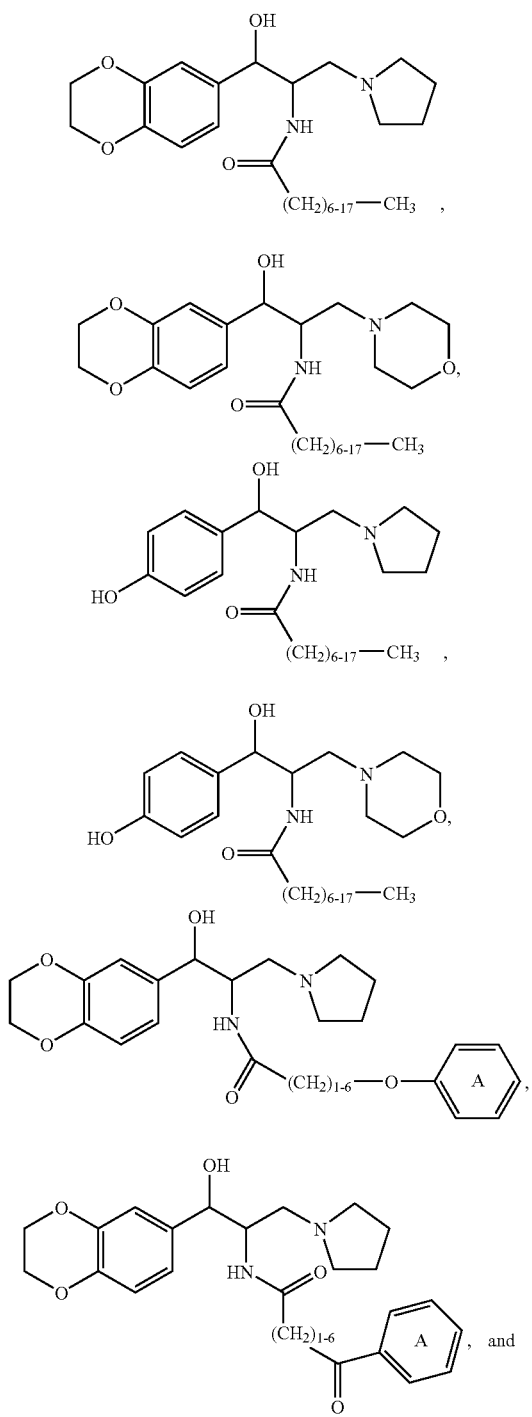

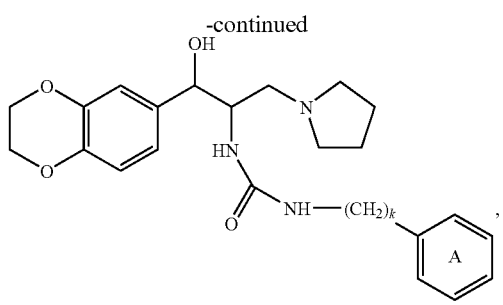

and pharmaceutically acceptable salts thereof, wherein each ring A is optionally substituted with one or more substituents selected from the group consisting of halogen, alkyl and alkoxy.

It is to be understood that when any compound is referred to herein by name or structure, solvates, hydrates and polymorphs thereof are included.

The ceramide derivatives disclosed herein may contain one or more chiral center and/or double bond and, therefore, exist as stereoisomers, such as double-bond isomers (i.e., geometric isomers), enantiomers, or diastereomers. When the ceramide derivatives are depicted or named herein without indicating the stereochemistry, it is to be understood that stereomerically pure forms (e.g., geometrically pure, enantiomerically pure, or diastereomerically pure) and stereoisomeric mixtures are encompassed. For example, the compound represented by Structural Formula (I) below has chiral centers 1 and 2. Accordingly, the ceramide derivatives depicted by Structural Formula (I) include the (1R,2R), (1R,2S), (1S,2R) or (1S,2S) stereoisomer and mixtures thereof.

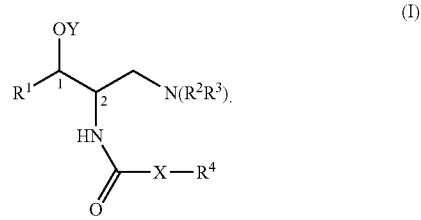

In some specific embodiments, the ceramide derivatives represented by Structural Formula (I) are (1R,2R) stereoisomers.

As used herein, a racemic mixture means about 50% of one enantiomer and about 50% of its corresponding enantiomer relative to all chiral centers in the molecule.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

When the stereochemistry of the disclosed compounds is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% optically pure. Percent optical purity by weight is the ratio of the weight of the enatiomer over the weight of the enantiomer plus the weight of its optical isomer.

Pharmaceutically acceptable salts of the ceramide derivatives can be used in the methods disclosed herein. The ceramide derivatives that include one or more basic amine groups can form pharmaceutically acceptable salts with pharmaceutically acceptable acid(s). Suitable pharmaceutically acceptable acid addition salts include salts of inorganic acids (such as hydrochloric acid, hydrobromic, phosphoric, metaphosphoric, nitric, and sulfuric acids) and of organic acids (such as, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, and tartaric acids). The ceramide derivatives that include one or more acidic groups, such as carboxylic acids, can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

The term "halo" as used herein means halogen and includes chloro, fluoro, bromo and iodo.

An "aliphatic group" is non-aromatic, consists solely of carbon and hydrogen and may optionally contain one or more units of unsaturation, e.g., double and/or triple bonds. An aliphatic group may be straight chained, branched or cyclic. When straight chained or branched, an aliphatic group typically contains between 1 and 20 carbon atoms, typically between 1 and 10 carbon atoms, more typically between 1 and 6 atoms. When cyclic, an aliphatic group typically contains between 3 and 10 carbon atoms, more typically between about 3 and 7 carbon atoms. A "substituted aliphatic group" is substituted at any one or more "substitutable carbon atom". A "substitutable carbon atom" in an aliphatic group is a carbon in an aliphatic group that is bonded to one or more hydrogen atoms. One or more hydrogen atoms can be optionally replaced with a suitable substituent group. A "haloaliphatic group" is an aliphatic group, as defined above, substituted with one or more halogen atoms. Suitable substituents on a substitutable carbon atom of an aliphatic group are the same as those for an alkyl group.

The term "alkyl" used alone or as part of a larger moiety, such as "alkoxy", "haloalkyl", "arylalkyl", "alkylamine", "cycloalkyl", "dialkyamine", "alkylamino", "dialkyamino" "alkylcarbonyl", "alkoxycarbonyl" and the like, as used herein means saturated straight-chain, cyclic or branched aliphatic group. As used herein, a C1-C6 alkyl group is referred to "lower alkyl." Similarly, the terms "lower alkoxy", "lower haloalkyl", "lower arylalkyl", "lower alkylamine", "lower cycloalkylalkyl", "lower dialkyamine", "lower alkylamino", "lower dialkyamino" "lower alkylcarbonyl", "lower alkoxycarbonyl" include straight and branched saturated chains containing one to six carbon atoms. In some specific embodiments, the "alkyl" used alone or as part of a larger moiety, such as "alkoxy", "haloalkyl", "arylalkyl", "alkylamine", "cycloalkyl", "dialkyamine", "alkylamino", "dialkyamino" "alkylcarbonyl", "alkoxycarbonyl" and the like, independently is C1-C10 alkyl, or, alternatively, C1-C6 alkyl.

The term "alkoxy" means —O-alkyl; "hydroxyalkyl" means alkyl substituted with hydroxy; "aralkyl" means alkyl substituted with an aryl group; "alkoxyalkyl" mean alkyl substituted with an alkoxy group; "alkylamine" means amine substituted with an alkyl group; "cycloalkylalkyl" means alkyl substituted with cycloalkyl; "dialkyamine" means amine substituted with two alkyl groups; "alkylcarbonyl" means —C(O)—R*, wherein R* is alkyl; "alkoxycarbonyl" means —C(O)—OR*, wherein R* is alkyl; and where alkyl is as defined above.

The terms "haloalkyl" and "haloalkoxy" mean alkyl or alkoxy, as the case may be, substituted with one or more halogen atoms. The term "halogen" means F, Cl, Br or I. Preferably the halogen in a haloalkyl or haloalkoxy is F.

The term "acyl group" means —C(O)R*, wherein R* is an optionally substituted alkyl group or aryl group (e.g., optionally substituted phenyl). R is preferably an unsubstituted alkyl group or phenyl.

An "alkylene group" is represented by —[CH$_2$]$_z$—, wherein z is a positive integer, preferably from one to eight, more preferably from one to four.

An "alkenylene group" is an alkylene in which at least a pair of adjacent methylenes are replaced with —CH═CH—.

An "alkynylene group" is an alkylene in which at least a pair of adjacent methylenes are replaced with —C≡C—.

The term "aryl group" used alone or as part of a larger moiety as in "arylalkyl", "arylalkoxy", or "aryloxyalkyl", means carbocyclic aromatic rings. The term "carbocyclic aromatic group" may be used interchangeably with the terms "aryl", "aryl ring" "carbocyclic aromatic ring", "aryl group" and "carbocyclic aromatic group". An aryl group typically has 6-14 ring atoms. A "substituted aryl group" is substituted at any one or more substitutable ring atom. The term "C$_{6-14}$ aryl" as used herein means a monocyclic, bicyclic or tricyclic carbocyclic ring system containing from 6 to 14 carbon atoms and includes phenyl, naphthyl, anthracenyl, 1,2-dihydronaphthyl, 1,2,3,4-tetrahydronaphthyl, fluorenyl, indanyl, indenyl and the like.

The term "heteroaryl", "heteroaromatic", "heteroaryl ring", "heteroaryl group" and "heteroaromatic group", used alone or as part of a larger moiety as in "heteroarylalkyl" or "heteroarylalkoxy", refers to aromatic ring groups having five to fourteen ring atoms selected from carbon and at least one (typically 1-4, more typically 1 or 2) heteroatoms (e.g., oxygen, nitrogen or sulfur). They include monocyclic rings and polycyclic rings in which a monocyclic heteroaromatic ring is fused to one or more other carbocyclic aromatic or heteroaromatic rings. The term "5-14 membered heteroaryl" as used herein means a monocyclic, bicyclic or tricyclic ring system containing one or two aromatic rings and from 5 to 14 atoms of which, unless otherwise specified, one, two, three, four or five are heteroatoms independently selected from N, NH, N(C$_{1-6}$alkyl), O and S.

Examples of monocyclic heteroaryl groups, for example, for the heteroaryl groups represented by each of R$^1$, R$^2$, R$^3$, R$^4$, R$^7$, R$^{10}$, R$^{21}$, R$^{22}$, R$^{30}$, R$^{32}$, R$^{40}$, R$^{42}$, R$^{50}$, R$^{52}$, Ar$^1$, Ar$^2$ and Ar$^3$, include furanyl (e.g., 2-furanyl, 3-furanyl), imidazolyl (e.g., N-imidazolyl, 2-imidazolyl, 4-imidazolyl, 5-imidazolyl), isoxazolyl(e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), triazolyl (e.g., 2-triazolyl, 5-triazolyl), tetrazolyl (e.g., tetrazolyl) and thienyl (e.g., 2-thienyl, 3-thienyl. Examples of monocyclic six-membered nitrogen-containing heterayl groups, for example, for the heteroaryl groups represented by each of R$^1$, R$^2$, R$^3$, R$^4$, R$^7$, R$^{10}$, R$^{21}$, R$^{22}$, R$^{30}$, R$^{32}$, R$^{40}$, R$^{42}$, R$^{50}$, R$^{52}$, Ar$^1$, Ar$^2$ and Ar$^3$, include pyrimidinyl, pyridinyl and pyridazinyl. Examples of polycyclic aromatic heteroaryl groups, for example, for the heteroaryl groups represented by each of R$^1$, $R^2$, $R^3$, $R^4$, $R^7$, $R^{10}$, $R^{21}$, $R^{22}$, $R^{30}$, $R^{32}$, $R^{40}$, $R^{42}$, $R^{50}$, $R^{52}$, $Ar^1$, $Ar^2$ and $Ar^3$, include carbazolyl, benzimidazolyl, benzothienyl, benzofuranyl, indolyl, quinolinyl, benzotriazolyl, benzothiazolyl, benzoxazolyl, benzimidazolyl, isoquinolinyl, indolyl, isoindolyl, acridinyl, or benzisoxazolyl.

Typically, the aryl and heteroaryl groups represented by each of R, R', $R^1$, $R^2$, $R^3$, $R^4$, $R^7$, $R^{10}$, $R^{21}$, $R^{22}$, $R^{30}$, $R^{32}$, $R^{40}$, $R^{42}$, $R^{50}$, $R^{52}$, $Ar^1$, $Ar^2$ and $Ar^3$ are C6-C14 aryl and 5-14 membered heteroaryl groups, respectively. Specific examples of the aryl and heteroaryl groups, including those represented by each of R, R', $R^1$, $R^2$, $R^3$, $R^4$, $R^7$, $R^{10}$, $R^{21}$, $R^{22}$, $R^{30}$, $R^{32}$, $R^{40}$, $R^{42}$, $R^{50}$, $R^{52}$, $Ar^1$, $Ar^2$ and $Ar^3$ each independently include:

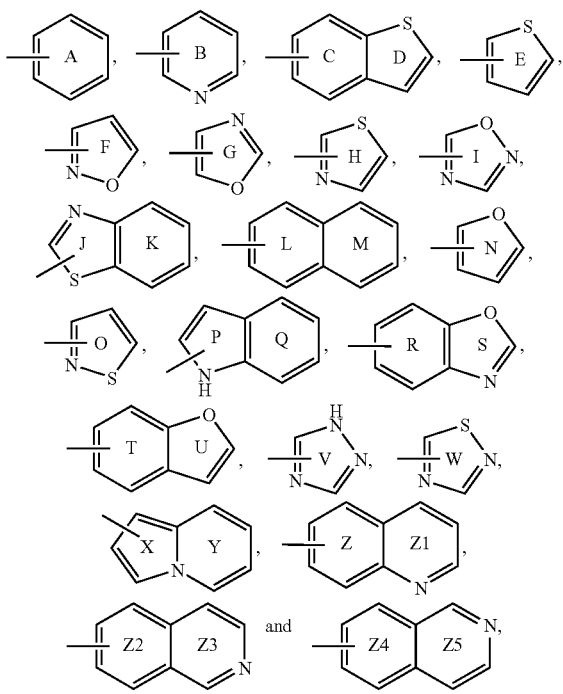

wherein each of rings A-Z5 is optionally and independently substituted. Suitable substituents for rings A-Z5 are as described above. In a specific embodiment, the aryl and heteroaryl groups, including those represented by each of R, R', $R^1$, $R^2$, $R^3$, $R^4$, $R^7$, $R^{10}$, $R^{21}$, $R^{22}$, $R^{30}$, $R^{32}$, $R^{40}$, $R^{42}$, $R^{50}$, $R^{52}$, $Ar^1$, $Ar^2$ and $Ar^3$, include monocyclic rings A, B, E, F, G, H, I, N, O, V, and W, wherein each ring is optionally and independently substituted.

The aryl and heteroaryl groups, including those represented by each of R, R', $R^1$, $R^2$, $R^3$, $R^4$, $R^7$, $R^{10}$, $R^{21}$, $R^{22}$, $R^{30}$, $R^{32}$, $R^{40}$, $R^{42}$, $R^{50}$, $R^{52}$, $Ar^1$, $Ar^2$ and $Ar^3$, can be optionally substituted. In certain embodiments, the aryl and heteroaryl groups are each independently optionally substituted with one or more substituents selected from the group consisting of halogen, nitro, cyano, hydroxy, $C_{1-20}$ alkyl, $C_{2-20}$ alkenyl, $C_{2-20}$ alkynyl, amino, $C_{1-20}$ alkylamino, $C_{1-20}$ dialkylamino, $C_{1-20}$ alkoxy, ($C_{1-10}$ alkoxy)$C_{1-20}$ alkyl, $C_{1-20}$ haloalkoxy, ($C_{1-10}$ haloalkoxy)$C_{1-20}$ alkyl and $C_{1-20}$ haloalkyl. More specific substituents for the aryl and heteroaryl groups, including those represented by each of R, R', $R^1$, $R^2$, $R^3$, $R^4$, $R^7$, $R^{10}$, $R^{21}$, $R^{22}$, $R^{30}$, $R^{32}$, $R^{40}$, $R^{42}$, $R^{50}$, $R^{52}$, $Ar^1$, $Ar^2$ and $Ar^3$, include halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, ($C_{1-6}$alkoxy)$C_{1-10}$ alkyl, $C_{1-10}$ haloalkoxy, ($C_{1-6}$haloalkoxy)$C_{1-10}$alkyl and $C_{1-10}$ haloalkyl. More specific substituents include $C_{1-10}$alkyl, —OH, $C_{1-10}$alkoxy, $C_{1-10}$ haloalkyl, halogen, $C_{1-10}$haloalkoxy, amino, nitro and cyano.

The term "non-aromatic heterocyclic group", used alone or as part of a larger moiety as in "non-aromatic heterocyclylalkyl group", refers to non-aromatic ring systems typically having five to twelve members, preferably five to seven, in which one or more ring carbons, preferably one or two, are each replaced by a heteroatom such as N, O, or S. A non-aromatic heterocyclic group can be monocyclic or fused bicyclic. A "nitrogen-containing non-aromatic heterocyclic group" is a non-aromatic heterocyclic group with at least one nitrogen ring atom.

Examples of non-aromatic heterocyclic groups include (tetrahydrofuranyl (e.g., 2-tetrahydropyranyl, 3-tetrahydropyranyl, 4-tetrahydropyranyl), [1,3]-dioxalanyl, [1,3]-dithiolanyl, [1,3]-dioxanyl, tetrahydrothienyl (e.g., 2-tetrahydrothienyl, 3-tetrahydrothieneyl), azetidinyl (e.g., N-azetidinyl, 1-azetidinyl, 2-azetidinyl), oxazolidinyl (e.g., N-oxazolidinyl, 2-oxazolidinyl, 4-oxazolidinyl, 5-oxazolidinyl), morpholinyl (e.g., N-morpholinyl, 2-morpholinyl, 3-morpholinyl), thiomorpholinyl (e.g., N-thiomorpholinyl, 2-thiomorpholinyl, 3-thiomorpholinyl), pyrrolidinyl (e.g., N-pyrrolidinyl, 2-pyrrolidinyl, 3-pyrrolidinyl) piperazinyl (e.g., N-piperazinyl, 2-piperazinyl), piperidinyl (e.g., N-piperidinyl), 2-piperidinyl, 3-piperidinyl, 4-piperidinyl), thiazolidinyl (e.g., 4-thiazolidinyl), diazolonyl and N-substituted diazolonyl. The designation "N" on N-morpholinyl, N-thiomorpholinyl, N-pyrrolidinyl, N-piperazinyl, N-piperidinyl and the like indicates that the non-aromatic heterocyclic group is attached to the remainder of the molecule at the ring nitrogen atom.

The ceramide derivatives disclosed herein can be prepared by processes analogous to those established in the art, for example, in U.S. Pat. No. 5,849,326; U.S. Pat. No. 5,916,911; U.S. Pat. No. 6,255,336; U.S. Pat. No. 7,148,251; U.S. Pat. No. 6,855,830; U.S. Pat. No. 6,835,831; and U.S. Provisional Application No. 60/932,370, filed May 31, 2007, the entire teachings of which are incorporated herein by reference. It is noted that the definitions of terms provided herein prevail over those of the references incorporated herein by reference.

The ceramide derivatives disclosed herein or salts thereof can be administered by an appropriate route. Suitable routes of administration include, but are not limited to, orally, intraperitoneally, subcutaneously, intramuscularly, intradermally, transdermally, rectally, sublingually, intravenously, buccally or via inhalation. Typically, the compounds are administered orally or intravenously.

As used herein a "subject" is a mammal, preferably a human, but can also be an animal in need of veterinary treatment, such as a companion animal (e.g., dogs, cats, and the like), a farm animal (e.g., cows, sheep, pigs, horses, and the like) or a laboratory animal (e.g., rats, mice, guinea pigs, and the like). Subject and patient are used interchangeably.

"Treatment" or "treating" refers to both therapeutic and prophylactic treatment.

An effective amount of a disclosed ceramide derivative depends, in each case, upon several factors, e.g., the health, age, gender, size and condition of the subject to be treated, the intended mode of administration, and the capacity of the subject to incorporate the intended dosage form, among others. An effective amount of an active agent is an amount sufficient to have the desired effect for the condition being treated, which can either be treatment of an active disease state or prophylactically inhibiting the active disease state from appearing or progressing. For example, an effective amount of a compound for treating a polycystic kidney disease is the quantity of compound that results in a slowing in the progression of the polycystic kidney disease, a reversal of the polycystic kidney disease state, the inhibition of new cyst formation (partial or complete inhibition of cystogenesis), a reduction in cyst mass, a reduction in the size and number of cysts, and/or a reduction in the severity of the symptoms associated with the polycystic kidney disease.

Typically, the ceramide derivatives disclosed herein are administered for a sufficient period of time to achieve the desired therapeutic effect. Effective amounts of the disclosed ceramide derivatives typically range between 0.001 mg/kg per day and 500 mg/kg per day, such as between 0.1 and 500 mg/kg body weight per day, between 0.1 and 100 mg/kg body weight per day or between 0.01 mg/kg per day and 50 mg/kg per day. The disclosed ceramide derivatives may be administered continuously or at specific timed intervals. For example, the ceramide derivatives may be administered 1, 2, 3, or 4 times per day, such as, e.g., a daily or twice-daily dosage regimen. Commercially available assays may be employed to determine optimal dose ranges and/or schedules for administration. For example, assays for measuring blood glucose levels are commercially available (e.g., OneTouch®Ultra®, Lifescan, Inc. Milpitas, Calif.). Kits to measure human insulin levels are also commercially available (Linco Research, Inc. St. Charles, Mo.). Additionally, effective doses may be extrapolated from dose-response curves obtained from animal models (see, e.g., Comuzzie et al., Obes. Res. 11 (1):75 (2003); Rubino et al., Ann. Surg. 240(2):389 (2004); Gill-Randall et al., Diabet. Med. 21 (7):759 (2004), the entire teachings of which are incorporated herein by reference). Therapeutically effective dosages achieved in one animal model can be converted for use in another animal, including humans, using conversion factors known in the art (see, e.g., Freireich et al., Cancer Chemother. Reports 50(4):219 (1996), the entire teachings of which are incorporated herein by reference) and Table A below for equivalent surface area dosage factors.

| From: | Mouse (20 g) | Rat (150 g) | Monkey (3.5 kg) | Dog (8 kg) | Human (60 kg) |
|---|---|---|---|---|---|
| To: Mouse | 1 | ½ | ¼ | ⅙ | 1/12 |
| To: Rat | 2 | 1 | ½ | ¼ | 1/7 |
| To: Monkey | 4 | 2 | 1 | ⅗ | ⅓ |
| To: Dog | 6 | 4 | ⅗ | 1 | ½ |
| To: Human | 12 | 7 | 3 | 2 | 1 |

Typically, the pharmaceutical compositions of the ceramide derivatives disclosed herein can be administered before or after a meal, or with a meal. As used herein, "before" or "after" a meal is typically within two hours, preferably within one hour, more preferably within thirty minutes, most preferably within ten minutes of commencing or finishing a meal, respectively.

In one embodiment, the method of the present invention is a mono-therapy where the disclosed ceramide derivatives are administered alone. Accordingly, in this embodiment, the ceramide derivative is the only pharmaceutically active ingredient being administered for the treatment PKD.

In another embodiment, the method of the invention is a co-therapy with other therapeutically active drug(s). The disclosed ceramide derivatives are co-administered either simultaneously as a single dosage form or consecutively as separate dosage forms with other agents that ease the symptoms and/or complications associated with PKD. The associated symptoms with PKD include pain, headaches, urinary tract infections and high blood pressure. Examples of the agents that can be co-administered with the compounds of the invention include, but are not limited to, over-the counter pain medications, antibiotics, antimicrobials, thiazide diuretics, angiotensin-converting enzyme inhibitors, angiotensin II antagonists such as losartan, and calcium channel blockers such as diltiazem. Examples of pain medications include acetaminophen, aspirin, naproxen, ibuprofen and COX-2 selective inhibitors such as rofecoxib, celecoxib and valdecoxib. Examples of antibiotics and antimicrobials include cephalosporins, penicilin derivatives, aminoglycosidesm ciprofloxacin, erythromycin, chloramphemicol, tetracycline, ampicillin, gentamicin, sulfamethoxazole, trimethoprim and ciprofloxacin, streptomycin, rifamycin, amphotericin B, griseofulvin, cephalothin, cefazolin, fluconazole, clindamycin, erythromycin, bacitracin, vancomycin and fusidic acid Examples of thiazide diuretics include bendroflumethiazide, chlorothiazide, chlorthalidone, hydrochlorothiazide, hydroflumethiazide, methyclothiazide, metolazone, polythiazide, quinethazone and trichlormethiazide. Examples of angiotensin-converting enzyme inhibitors include benazepril, captopril, cilazapril, enalapril, enalaprilat, fosinopril, lisinopril, moexipril, perindopril, quinapril, ramipril and trandolapril.

Pharmaceutical compositions of the disclosed ceramide derivatives optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5$^{th}$ Ed., Pharmaceutical Press (2005)).

The carriers, diluents and/or excipients are "acceptable" in the sense of being compatible with the other ingredients of the pharmaceutical composition and not deleterious to the recipient thereof. The pharmaceutical compositions can conveniently be presented in unit dosage form and can be prepared by any suitable method known to the skilled artisan. In general, the pharmaceutical compositions are prepared by uniformly and intimately bringing into association the compounds disclosed herein with the carriers, diluents and/or excipients and then, if necessary, dividing the product into unit dosages thereof.

The pharmaceutical compositions of the disclosed ceramide derivatives can be formulated as a tablet, sachet, slurry, food formulation, troche, capsule, elixir, suspension, syrup, wafer, chewing gum or lozenge. A syrup formulation will generally consist of a suspension or solution of the compounds of the invention described herein or salt in a liquid carrier, for example, ethanol, glycerine or water, with a flavoring or coloring agent. Where the composition is in the form of a tablet, one or more pharmaceutical carriers routinely used for preparing solid formulations can be employed. Examples of such carriers include magnesium stearate, starch, lactose and sucrose. Where the composition is in the form of a capsule, the use of routine encapsulation is generally suitable, for example, using the aforementioned carriers in a hard gelatin capsule shell. Where the composition is in the form of a soft gelatin shell capsule, pharmaceutical carriers routinely used for preparing dispersions or suspensions can be considered, for example, aqueous gums, celluloses, silicates or oils, and are incorporated in a soft gelatin capsule shell.

Though the above description is directed toward routes of oral administration of pharmaceutical compositions consistent with embodiments of the invention, it is understood by those skilled in the art that other modes of administration using vehicles or carriers conventionally employed and which are inert with respect to the compounds of the invention may be utilized for preparing and administering the pharmaceutical compositions. For example, the pharmaceutical compositions of the invention may also be formulated for rectal administration as a suppository or retention enema, e.g., containing conventional suppository bases such as cocoa butter or other glycerides. Also, the pharmaceutical compositions of the invention can be formulated for injection, or for transdermal or transmucosal administration. Illustrative of various modes of administration methods, vehicles and carriers are those described, for example, in Remington's Pharmaceutical Sciences, 18$^{th}$ ed. (1990), the disclosure of which is incorporated herein by reference.

The invention is illustrated by the following examples which are not intended to be limiting in any way.

EXEMPLIFICATION

Example 1

Synthesis of Ceramide Derivatives: General Methods for the Preparation of Amide Analogs Example 1A Synthetic Route 1

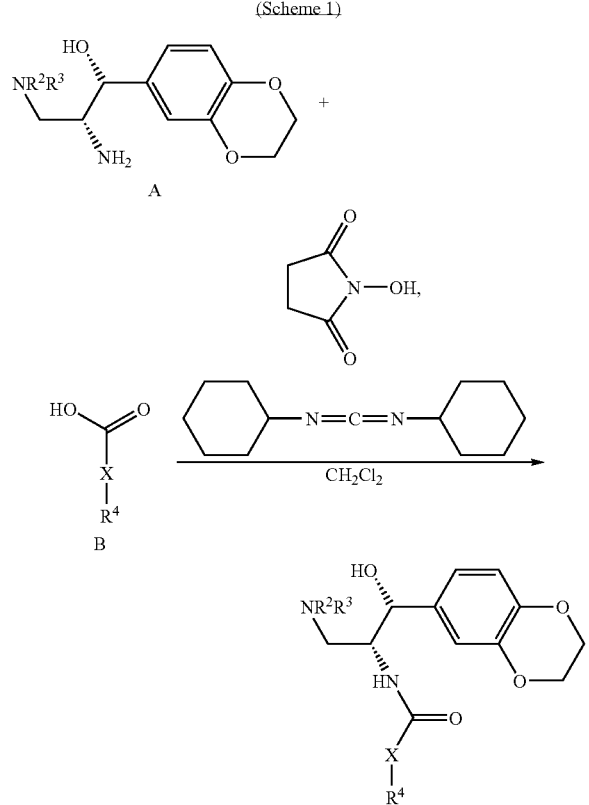

Method 1

A mixture of Compound A (1 mmol), such as (1R,2R)-2-amino-1-(2,3-dihydrobenzo[β][1,4]dioxin-6-yl)-3-(pyrrolidin-1-yl)propan-1-ol, an acid (Compound B, 1.2 mmol), DCC (dicyclohexylcarbodiimide, 1.2 mmol) and HOBT (1-hydroxy benzotriazole, 1.2 mmol) was dissolved in $CH_2Cl_2$ (5 ml). The mixture was stirred at room temperature and monitored by TLC (thin liquid chromatography) for completion. After completion the mixture was filtered and purified by column chromatography using, for example, a mixture of ($CH_2Cl_2$/MeOH/$NR_4OH$).

Method 2

A mixture of Compound A (1 mmol), such as (1R,2R)-2-amino-1-(2,3-dihydrobenzo[β][1,4]dioxin-6-yl)-3-(pyrrolidin-1-yl)propan-1-ol, an acid (Compound B, 1.2 mmol) and DCC (dicyclohexylcarbodiimide, 1.2 mmol) was dissolved in $CHCl_3$ (5 ml). The mixture was placed in the microwave reactor (T=120° C., time=1 min) and it was then filtered and purified by column chromatography using, for example, a mixture of ($CH_2Cl_2$/MeOH/$NH_4OH$).

Method 3

A mixture of Compound A (1 mmol), such as (1R,2R)-2-amino-1-(2,3-dihydrobenzo[β][1,4]dioxin-6-yl)-3-(pyrrolidin-1-yl)propan-1-ol, an acid chloride of Compound B, 1.2 mmol) and $K_2CO_3$ (2 mmol) was suspended in THF (5 ml). The mixture was stirred at room temperature and monitored by TLC for completion. After completion, the mixture was filtered and purified by column chromatography using, for example, a mixture of ($CH_2Cl_2$/MeOH/$NH_4OH$).

Example 1B

Synthetic Route 2

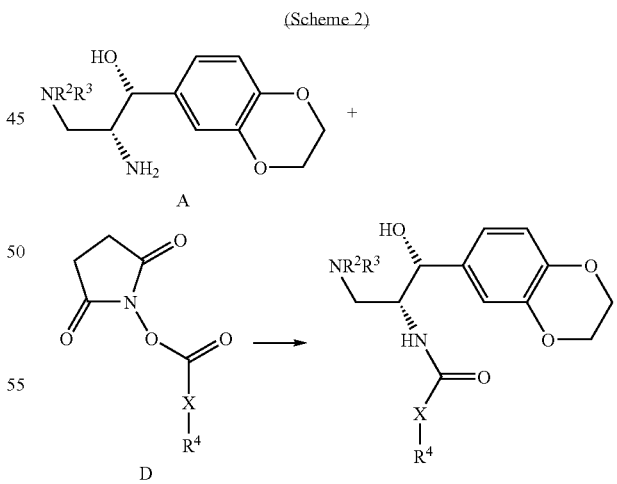

Compound A, such as (1R,2R)-2-amino-1-(2,3-dihydrobenzo[1,4]dioxin-6-yl)-3-pyrrolidin-1-yl-propan-1-ol, was coupled with a variety of N-hydroxysuccinamide esters (Compound D prepared according to the method below) in methylene chloride under an atmosphere of nitrogen, for example, for 18 to 24 hours depending on the ester used.

Preparation of N-Hydroxysuccinamide Esters (Scheme 3)

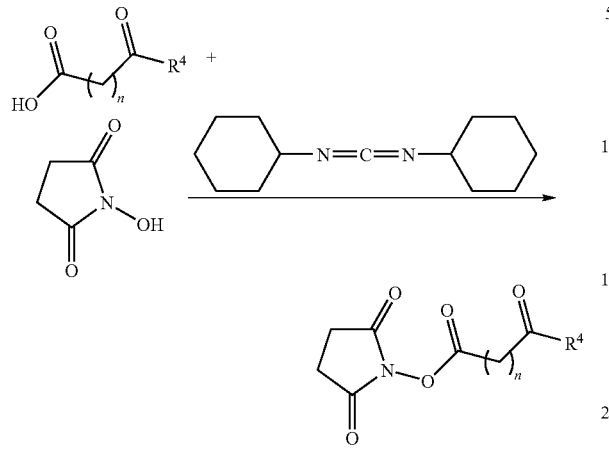

Various mono- and di-keto acids were coupled with N-hydroxysuccinamide in the presence of N,N[1]-dicyclohexylcarbodiimide in ethyl acetate under an atmosphere of nitrogen for 18 hours. The products were filtered to remove the dicyclohexylurea. The identity of these esters was confirmed by $^1$H NMR and the crude material was then used in the preparation of amide analogs without further purification.

Example 1C

Preparation of Compound A of Schemes 1 and 2

(1R,2R)-2-amino-1-(2,3-dihydro-benzo[1,4]dioxin-6-yl)-3-pyrrolidin-1-yl-propan-1-ol was prepared by according to the preparation of intermediate 4 of U.S. Pat. No. 5,855,830, the entire teachings of which are incorporated herein by reference. A general synthetic route for preparing Compound A with various —NR$^2$R$^3$ is depicted in Scheme 4 below.

(Scheme 4)

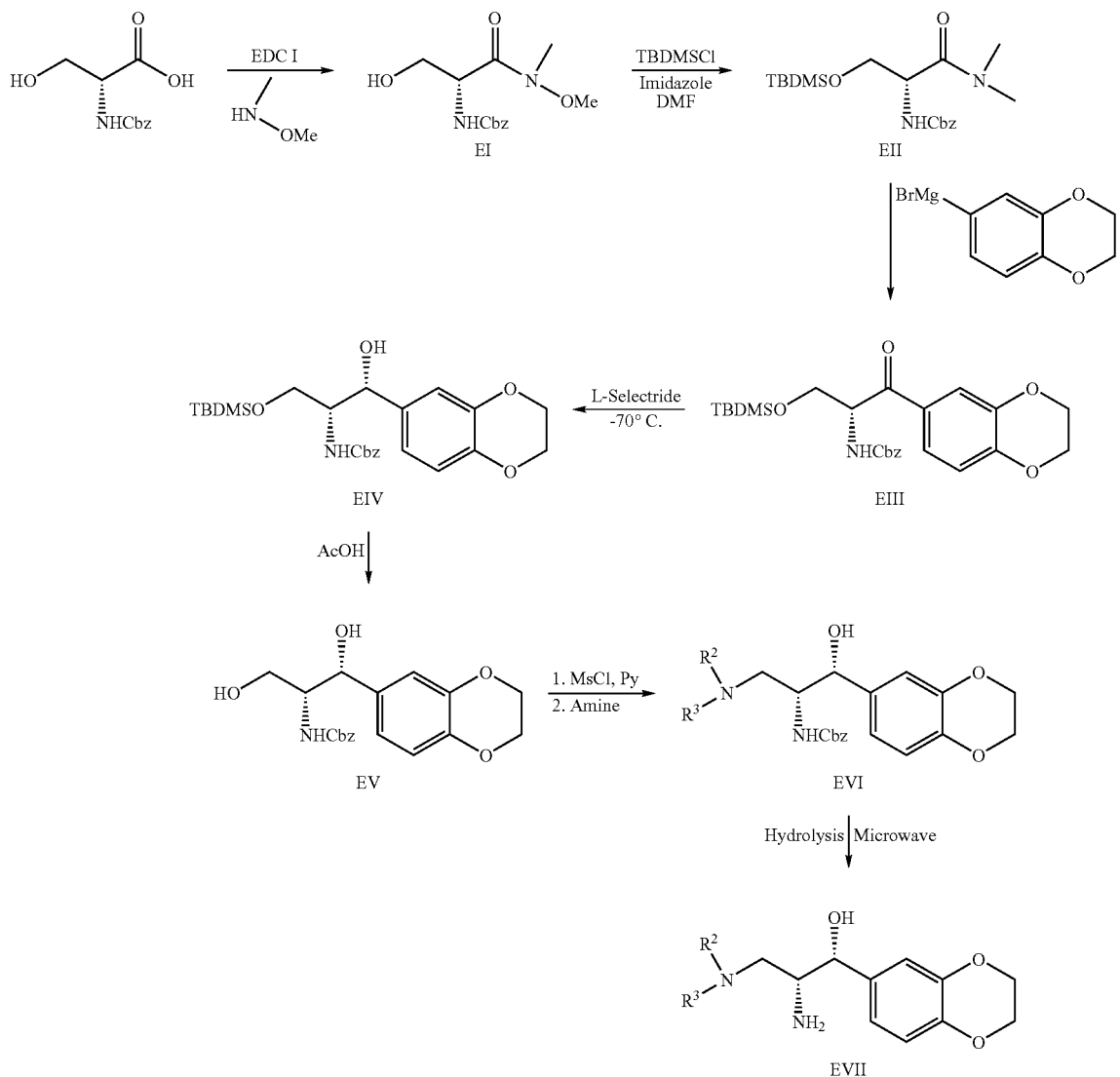

Preparation of EII: (R)-benzyl 3,8,8,9,9-pentamethyl-4-oxo-2,7-dioxa-3-aza-8-siladecan-5-ylcarbamate Imidazole (1.8 g, 26.5 mmol) was added to a solution of (R)-benzyl 3-hydroxy-1-(methoxy(methyl)amino)-1-oxopropan-2-ylcarbamate (3 g, 10.6 mmol) in DMF (dimethyl formamide, 15 mL) followed by TBDMSiCl (tert-butyldimethylsilyl chloride, 2.4 g, 15.95 mmol). The reaction stirred for 12 hrs at room temperature under nitrogen atmosphere and was quenched with aqueous ammonium chloride (100 ml). The aqueous layer was extracted with methylene chloride (200 mL) and ethyl acetate (100 mL) and the organic layers were washed with brine and concentrated. The crude product was purified by column chromatography using 10% EtOAc (ethylacetate)-hexanes to give an oil (3 g, 74% yield). $^1$H NMR (400 MHz, CDCl$_3$) δ=0 (s, 6H), 0.9 (s, 9H), 3.2 (s, 3H), 3.8 (s, 3H), 3.8-3.9 (m, 2H), 4.8 (broad s, 1H), 5.1 (q, 2H), 5.7 (d, 1H), 7.2-7.4 (m, 5H).

Preparation of EIII: (R)-benzyl 3-(tert-butyldimethylsilyloxy)-1-(2,3-dihydrobenzo[β][1,4]dioxin-6-yl)-1-oxopropan-2-ylcarbamate (2,3-dihydrobenzo[β][1,4]dioxin-6-yl)magnesium bromide (26 g, 78 mmol) dissolved in 40 mL of THF (tetrahydrofuran) under a nitrogen atmosphere was cooled down to −70° C. and (R)-benzyl 3,8,8,9,9-pentamethyl-4-oxo-2,7-dioxa-3-aza-8-siladecan-5-ylcarbamate (12.3 g, 31 mmol) dissolved in THF (13 ml) were added dropwise. The reaction mixture was allowed to warm up to −15° C. and left to react for 12 hrs followed by stirring at room temperature for 2 hrs. After cooling the reaction mixture to −40° C. it was quenched using aqueous ammonium chloride and the aqueous layer was extracted with EtOAc dried over magnesium sulfate and concentrated. The crude product was purified by column chromatography using 25% EtOAc-hexanes to give pure product (13 g, 88% yield). $^1$H NMR (400 MHz, CDCl$_3$) δ=0 (d, 6H), 0.9 (s, 9H), 4.0-4.2 (m, 2H), 4.4 (s, 2H), 4.5 (s, 2H), 5.2 (s, 2H), 5.4 (m, 1H), 6.1 (d, 1H), 7 (d, 1H), 7.4-7.7 (m, 7H).

Preparation of EIV: benzyl(1R,2R)-3-(tert-butyldimethylsilyloxy)-1-(2,3-dihydrobenzo[β][1,4]dioxin-6-yl)-1-hydroxypropan-2-ylcarbamate (R)-benzyl 3-(tert-butyldimethylsilyloxy)-1-(2,3-dihydrobenzo[β][1,4]dioxin-6-yl)-1-oxopropan-2-ylcarbamate (3.1 g, 6.6 mmol) were dissolved in THF (25 ml) and cooled down to −70° C. under nitrogen atmosphere. L Selectride (13.2 ml of 1M solution in THF, 13 mmol) was added dropwise while keeping the temperature at −70° C. After 1 hour, the reaction was quenched with a 1M aqueous solution of potassium tartrate (13 ml) and extracted with EtOAc. The organic layer was evaporated down and the product was purified by column chromatography using 2.5% EtOAc-2% acetone-methylene chloride. The desired diastereomer was obtained in 80% yield (2.5 g). $^1$H NMR (400 MHz, CDCl$_3$) δ=0 (d, 6H), 0.9 (s, 9H), 3.5 (broad s, 1H), 3.7-3.9 (m, 2H), 4.2 (s, 4H), 4.9 (broad s, 1H), 5.0 (d, 2H), 5.4 (d, 1H), 6.8 (s, 2H), 6.9 (s, 1H), 7.2-7.4 (m, 5H).

Preparation of EV: benzyl(1R,2R)-1-(2,3-dihydrobenzo[β][1,4]dioxin-6-yl)-1,3-dihydroxypropan-2-ylcarbamate Benzyl(1R,2R)-3-(tert-butyldimethylsilyloxy)-1-(2,3-dihydrobenzo[β][1,4]dioxin-6-yl)-1-hydroxypropan-2-ylcarbamate (0.5 g) was dissolved in a 4 ml mixture of Acetic acid/THF/water (3/1/1) and left to stir over night. The crude was evaporated down and the product azeotropically dried with EtOAc (10 ml). The crude product was purified by column chromatography using 50% EtOAc-hexane. The pure product was obtained in 74% yield (0.28 g). $^1$H NMR (400 MHz, CDCl$_3$) δ=3.4-3.8 (m, 4H), 4.1 (broad s, 4H), 4.8 (s, 1H), 4.9 (broad s, 2H), 5.7 (broad s, 1H), 6.8 (s, 2H), 6.9 (s, 1H), 7.2-7.4 (m, 5H).

General Procedure for Preparation of EVI and EVII

Benzyl(1R,2R)-1-(2,3-dihydrobenzo[β][1,4]dioxin-6-yl)-1,3-dihydroxypropan-2-ylcarbamate was dissolved in excess pyridine, cooled to −15° C. and one equivalent of methanosulfonyl chloride was added to the mixture. Mixture was stirred about half an hour, and ten equivalents of the amine were added. The reaction mixture was allowed to warm up to room temperature and then heated at 50° C. overnight. The crude was evaporated down and the product was purified by column chromatography using a mixture of methanol/methylene chloride/ammonium hydroxide. The pure compound EVI was then de-protected by hydrolysis in the microwave, using aqueous NaOH (40% in weight)/methanol solution as solvent and heating the mixture to 150° C. for about 15 minutes to give the free amines of the type EVI. The final product was purified by silica-gel column chromatography using a mixture of methanol/methylene chloride/ammonium hydroxide.

Examples of EVII Compounds i) (1R,2R)-2-amino-1-(2,3-dihydrobenzo[β][1,4]dioxin-6-yl)-3-morpholinopropan-1-ol

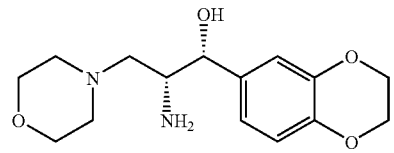 [SMILES: N[C@H](CN1CCOCC1)[C@H](O)c1ccc2c(c1)OCCO2]

$^1$H NMR (400 MHz, CDCl$_3$) δ=2.3 (dd, 2H), 2.4 (dd, 2H), 2.5-2.6 (m, 2H), 3.2 (m, 1H), 3.6-3.7 (m, 4H), 4.2 (s, 4H), 4.4 (d, 1H), 6.5-6.9 (m, 3H); MS for C$_{15}$H$_{22}$N$_2$O$_4$ m/z 294.8 [M+H].

ii) (1R,2R)-2-amino-1-(2,3-dihydrobenzo[β][1,4]dioxin-6-yl)-3-(piperidin-1-yl)propan-1-ol

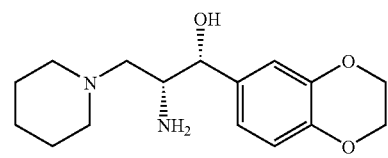 [SMILES: N[C@H](CN1CCCCC1)[C@H](O)c1ccc2c(c1)OCCO2]

$^1$H NMR (400 MHz, CDCl$_3$) δ=1.4 (broad s, 2H), 1.7 (m, 4H), 2.2-2.6 (m, 6H), 3.2 (m, 1H), 4.2 (s, 4H), 4.5 (s, 1H), 6.7-6.9 (m, 3H).

Example 1D

Preparation of Substituted Phenoxy Propionic Acids for Compound B in Scheme 1

Example 1D1

Preparation of 3-(4-methoxyphenoxy)propionic acid i) 3-(4-methoxyphenoxy)propionitrile (1)

A 740 g (5.96 mol, 1 eq.) sample of 4-methoxyphenol was charged to a 3 necked 5 L flask under nitrogen. Triton B (50 mL of a 30% wt. solution in methanol) was charged to the flask, and stirring initiated via an overhead stirrer. Acrylonitrile (2365 mL, 35.76 mol, 6 eq.) was then charged to the reaction flask in a single portion, and the reaction mixture heated at 78° C. for 36 h. HPLC analysis indicated that the reaction was complete at this point. Solvents were removed via rotary evaporation, and the resulting oil was chased with toluene to remove excess acrylonitrile. The crude material was recrystallized from TBME (tert-butyl methyl ether) 10 volumes relative to the crude weight), and dried in a vacuum oven to give 945 g of 1 as white crystals (Yield: 89.48%). $^1$H NMR (450 MHz, CDCl$_3$): δ=2.72 (t, 2H; CH$_2$CN); δ=3.83 (s, 3H; OCH$_3$); δ=4.05 (t, 2H; OCH$_2$); δ=6.70 (m, 4H; Ar—H); $^{13}$C NMR (112.5 MHz, CDCl$_3$): d=18.843 (CH$_2$CN); 55.902 (OCH$_3$); 63.699 (OCH$_2$); 114.947 (CH$_3$OCCH); 116.183 (CH$_2$OCCH); 117.716 (CN); 151.983 (CH$_3$OC); 154.775 (CH$_2$OC).

ii) 3-(4-methoxyphenoxy)propionic acid (2)

A 945 g (5.34 mol, 1 eq.) sample of 1 (3-(4-methoxyphenoxy)propionitrile (1)) was charged to a 22 L round bottom flask equipped with an overhead stirrer under N$_2$. To the stirred solids, 4 L of concentrated HCl was slowly added, followed by 2 L of H$_2$O. The reaction mixture was heated to 100° C. for 3.5 h, at which point the reaction was complete by HPLC analysis. The reaction was cooled to 10° C. by the addition of ice to the reaction mixture, and was filtered. The dried solids gave 920 g of crude 2. The crude material was dissolved in 5 L of 6 wt. % sodium carbonate (such that pH=9), and 2 L of DCM (dichloromethane) was added to the reaction vessel. After stirring thoroughly, the organic layer was separated and discarded via a separatory funnel, and the aqueous layer charged back into the 22 L flask. The pH of the aqueous layer was carefully adjusted to 4.0, by slow addition of 6 M HCl. The precipitated solids were filtered, and dried in a vacuum oven to give 900 g of 2 as a white solid (Yield: 86.04%). $^1$H NMR (450 MHz, CDCl$_3$); δ=2.78 (t, 2H; CH$_2$COOH); 3.70 (s, 3H; OCH$_3$); 4.18 (t, 2H; OCH$_2$); 6.78 (m, 4H; Ar—H); $^{13}$C NMR (112.5 MHz, CDCl$_3$): δ=34.703 (CH$_2$COOH); 55.925 (OCH$_3$); 64.088 (OCH$_2$); 114.855 (CH$_3$OCCH); 115.984 (CH$_2$OCCH); 152.723 (CH$_3$OC); 154.302 (CH$_2$OC); 177.386 (COOH).

Example 1D2

Preparation of 3-(4-(3-oxobutyl)phenoxy)propanoic acid

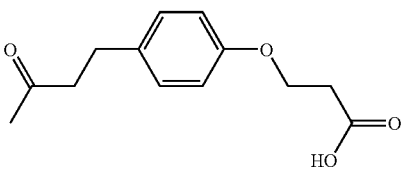 [SMILES: CC(=O)CCc1ccc(OCCC(=O)O)cc1]

Step 1: a mixture of 4-(p-hydroxyphenol)-2-butanone (1.032 g), triton 13 (400 µL), acrylonitrile (4 mL) and MeOH (0.8 mL) was heated at 70° C. for 20 hours. The mixture was cooled to room temperature and the solvent was removed to dryness. 3-(4-(3-oxobutyl)phenoxy)propanenitrile was obtained as a white solid (0.572 g) after purification by column chromatography using ethyl acetate/hexane.

Step 2: 3-(4-(3-oxobutyl)phenoxy)propanenitrile (0.478 g) was suspended in HCl (37%, 5 mL) and placed in the microwave reactor (T=110° C., 5 min). The mixture was poured onto iced water (20 g), filtered, and the solid was washed with water (2×5 mL). After column chromatography purification using a mixture of methylene chloride/methanol, 3-(4-(3-oxobutyl)phenoxy)propanoic acid was obtained as a white solid (0.3 g). $^1$H NMR (CDCl$_3$, 400 mHz, ppm); 2.2 (s, 3H), 2.7 (t, 2H), 2.85 (m, 4H), 4.25 (t, 2H), 6.8 (d, 2H), 7.1 (d, 2H).

Example 1D3

Preparation of 3-(4-(2-methoxyethyl)phenoxy)propanoic acid

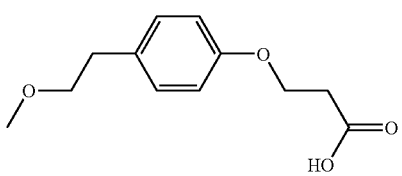 [SMILES: COCCc1ccc(OCCC(=O)O)cc1]

Step 1: a mixture of 4-(2-methoxy ethyl)phenol (1.547 g, 10.3 mmol), propiolic acid tert-butyl ester (1.367 g, 10.8 mmol) and N-methyl morpholine (1.18 mL, 10.8 mmol) in CH$_2$Cl$_2$ (15 mL) was stirred at room temperature for 24 hours. The mixture was absorbed on SiO$_2$ (20 g) and purified by column chromatography using a mixture of methylene chloride/hexane. The product was obtained as a two to one mixture of (E)/(Z)-tert-butyl 3-(4-(2-methoxyethyl)phenoxy) acrylate isomers (2.0 g).

Step2: (E)/(Z)-tert-butyl 3-(4-(2-methoxyethyl)phenoxy) acrylate (0.57 g) was suspended in a mixture of THF (5 mL)/HCl (2 M, 5 mL) and placed in the microwave reactor (T=100° C., 15 sec). THF was removed by rotary evaporation and the mixture was extracted with CH$_2$Cl$_2$ (10 mL). (E)/(Z)-3-(4-(2-methoxyethyl)phenoxy)acrylic acid was obtained as a white solid after purification by column chromatography using a mixture of hexane/ethyl acetate.

Step 3: (E)/(Z)-3-(4-(2-methoxyethyl)phenoxy)acrylic acid (0.3 g) was dissolved in EtOH (10 mL) and Pd/C (5%, degussa type E101, 40 mg) was added. The mixture was hydrogenated at atmospheric pressure for 2 hours and then filtered and the solvent removed to dryness. After purification by column chromatography using a mixture of hexane/ethyl acetate, 3-(4-(2-methoxyethyl)phenoxy)propanoic acid was obtained as a white solid (0.236 g). $^1$H NMR (CDCl$_3$, 400 mHz, ppm); 2.85 (t, 4H), 3.35 (s, 3H), 3.55 (t, 2H), 4.25 (t, 2H), 6.85 (d, 2H), 7.1 (d, 2H).

Example 1D4

Preparation of 3-(4-(3-methylbutanoyl)phenoxy)propanoic acid

Step 1: 3-phenoxypropionic acid (5.0 g, 30 mmol) was dissolved in MeOH (12 mL) and H$_2$SO$_4$ (18 M, 3 drops) was added. The mixture was place in the microwave reactor (T: 140° C., t: 5 min). The solvent was evaporated, the mixture was partitioned in EtOAc (30 mL) and NaOH (2N, 20 mL). The organic phase was dried over MgSO$_4$, filtered, and evaporated to give methyl 3-phenoxypropanoate (5.0 g, 27.7 mmol, 92.5%).

Step 2: aluminum chloride (1.1 g, 8.34 mmol) was added to a cold solution (0° C.) solution of methyl 3-phenoxypropanoate (1.0 g, 5.56 mmol) and tert-butylacetyl chloride (1.25 mL, 8.34 mmol) in CH$_2$Cl$_2$ (9 mL) and the reaction mixture was stirred overnight. The mixture was evaporated and the residue was diluted with EtOAc (30 mL) and then washed with water (2×20 mL). The organic phase was removed and purified with silica chromatography using of a gradient hexanes/EtOAc (100:0→0:100) to give methyl 3-phenoxypropanoate (600 mg, 2.27 mmol, 40%).

Step 3: a solution of methyl 3-phenoxypropanoate (200 mg, 0.76 mmol) in 2 mL of HCl (37%) was placed in a microwave reactor (T: 120° C., t: 5 min). The mixture was poured into iced water (2 g) and washed with EtOH (3×10 mL). The organic phase was combined and evaporated. The crude product was purified with silica gel chromatography using of a gradient hexanes/EtOAc (100:0→0:100) to give 3-(4-(3-methylbutanoyl)phenoxy)propanoic acid (120 mg, 0.48 mmol, 63%).

Example E

Preparation of Amide Analogs

Example 1E1

Preparation of Hemi-Hydrate of Compound 163
N-[2-Hydroxy-2-(2,3-dihydrobenzo[β][1,4]dioxin-6-yl)-1-pyrrolidin-1-ylmethyl-ethyl]-3-(4-methoxy-phenoxy)-propionamide (Scheme 1A)

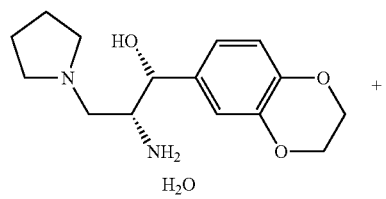

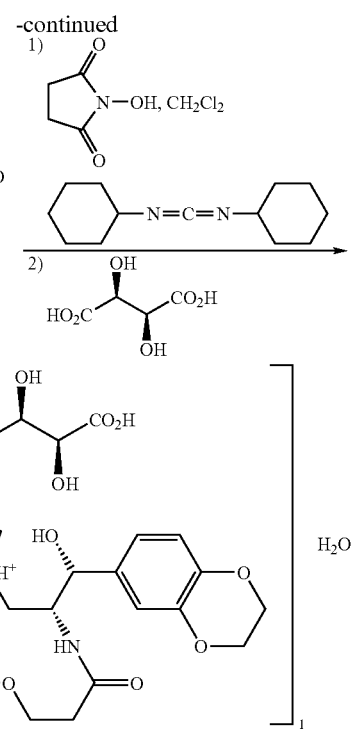

Compound 163 was prepared by following Scheme 1A above. 3-(4-methoxyphenoxy)propanoic acid (see Example 1D1, 34.47 g, 169 mmol, 96% purity by HPLC), DCC (34.78 g, 169 mmol) and N-hydroxysuccinimide (19.33, 169 mmol) were combined as dry powders and methylene chloride (500 mL) was added. The suspension was mechanically stirred overnight, ambient temperature, under a nitrogen atmosphere. HPLC analysis showed complete conversion of the acid to the NHS ester (N-hydroxy succinyl ester). To the mixture was added step 5 amine (50 g, 169 mmol) and stirring continued for 2.5 hours. HPLC showed conversion to the product and loss of both the NHS ester and step 5 amine. The reaction mixture was vacuum filtered on a Büchner funnel to remove DCC urea. The solid urea was washed with 500 mL of methylene chloride. The organic layers were combined, placed in a separatory funnel, and treated with 500 mL of 1.0M NaOH. The layers were separated, and the cloudy organic layer was recharged into a separatory funnel and treated with a 6% HCl solution (adjusted to pH=0.03-0.34, 100 mL of solution). Two clear layers formed. The resultant biphasic solution was poured into an Erlenmeyer flask and cautiously neutralized to a pH of 7.2-7.4 with a saturated solution of sodium bicarbonate (approx 200 mL of solution). The organic layer was separated from the aqueous layer, dried over sodium sulfate and evaporated to yield 83.6 g of yellow oil (theoretical yield: 77.03 g). The oil was dissolved in isopropyl alcohol (500 mL) with heating and transferred to a 1 L round bottom flask equipped with a mechanical stirrer and heating mantel. The solution was heated to 50° C. and the mechanical stirrer was set to a rate of 53-64 rpm. Tartaric acid (25.33 g, 168 mmol) was dissolved in deionized water (50 mL) and added to the stirred solution at 50° C. Once the solution turned from milky white to clear, seed crystals were added to the mixture and crystallization immediately began (temperature jumped to 56° C.). After 20 minutes, the mixture was set to cool to a temperature of 35° C. (cooling took 1.15 hours). Heating was removed and the solution was allowed to stir for 12 hours. The resulting thick slurry was filtered on a Büchner funnel. Any remaining solid in the flask was washed onto the funnel using ice-cold isopropyl alcohol (100 mL). The material was transferred to a drying tray and heated to 48° C. under vacuum for 3 days (after two days the material weighed 76 g and after three days it weighed 69.3 g). The solid was analyzed by LC and shown to be 98.1% pure (AUC), the residual solvent analysis showed the material to possess 3472 ppm of isopropyl alcohol, and the DSC (differential scanning calroimetery) showed a melting point of 134.89° C. A total of 69.3 g of white solid was collected (65.7% overall yield). $^1$H NMR (400 MHz, CDCl$_3$) δ=1.8 (M, 4H), 2.4-2.6 (m, 4H), 2.6 (m, 1H), 2.85 (m, 2H), 3.0 (m, 1H), 3.65 (s, 3H), 3.8 (m, 2H), 3.86 (2, 2H), 4.18 (br s, 5H), 4.6 (s, 1H), 6.6-6.8 (m, 7H), 7.8 (d, 1H); MS for C$_{29}$H$_{40}$N$_2$O$_{13}$ m/z 457.3 [M+H] for main peak (free-base).

Example 1E2

Preparation of Compound 247: N-((1R,2R)-1-hydroxy-1-(4-methoxyphenyl)-3-(pyrrolidin-1-yl)propan-2-yl)-3-(p-tolyloxy)propanamide

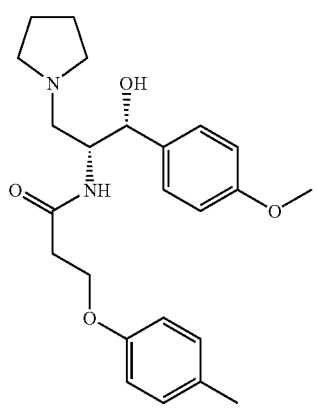 [SMILES: COc1ccc([C@@H](O)[C@@H](CN2CCCC2)NC(=O)CCOc2ccc(C)cc2)cc1]

Compound 247 was prepared in a similar manner as described above, following Scheme 1 using (1R,2R)-2-amino-1-(4-methoxyphenyl)-3-(pyrrolidin-1-yl)propan-1-ol as the amine.

$^1$H NMR (CDCl$_3$, 400 mHz, ppm); 1.75 (br, 4H), 2.3 (s, 3H), 2.65 (br, 6H), 2.85 (m, 2H), 3.75 (s, 3H), 4.1 (m, 2H), 4.25 (m, 1H), 5.05 (sd, 1H), 6.5 (br, 1H), 6.8 (m, 4H), 7.1 (d, 2H), 7.2 (d, 2H). M/Z for C$_{24}$H$_{32}$N$_2$O$_4$ [M–H]$^-$=413.

(1R,2R)-2-amino-1-(4-methoxyphenyl)-3-(pyrrolidin-1-yl)propan-1-ol as the amine was prepared by the procedures described below:

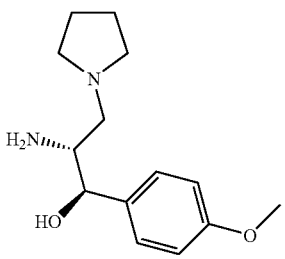 [SMILES: COc1ccc([C@@H](O)[C@H](N)CN2CCCC2)cc1]

A mixture of benzyl(1R,2R)-1-hydroxy-1-(4-methoxyphenyl)-3-(pyrrolidin-1-yl)propan-2-ylcarbamate (0.10 g, 0.26 mmol) and Pd/C (5%, 21 mg) in EtOH (1 mL)/HCl (1 M, 50 μL) was degassed and hydrogen gas was added. The mixture was hydrogenated at atmospheric pressure for two hours. The mixture was filtered over celite and the solvent was removed to dryness. The product was obtained as a colorless oil (63.5 mg, 85% yield).

Example 1E3

Preparation of Compound 251: N-((1R,2R)-1-hydroxy-1-(4-methoxyphenyl)-3-(pyrrolidin-1-yl)propan-2-yl)-2-(4-(trifluoromethyl)phenyl)acetamide

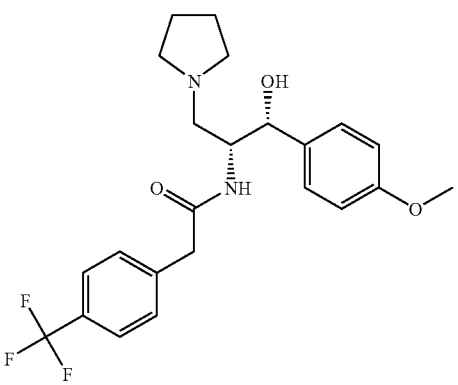 [SMILES: COc1ccc([C@@H](O)[C@@H](CN2CCCC2)NC(=O)Cc2ccc(C(F)(F)F)cc2)cc1]

Compound 251 was prepared in a similar manner as described above, following Scheme 1 using (1R,2R)-2-amino-1-(4-methoxyphenyl)-3-(pyrrolidin-1-yl)propan-1-ol as the amine (see Example 1E1).

$^1$H NMR (CDCl$_3$, 400 mHz, ppm); 1.75 (br, 4H), 2.55 (br, 4H), 2.85 (m, 2H), 3.5 (s, 2H), 3.8 (s, 3H), 4.2 (m, 1H), 5.05 (sd, 1H), 5.8 (d, 1H), 6.8 (d, 2H), 7.1 (d, 2H), 7.2 (d, 2H), 7.55 (d, 2H). M/Z for C$_{23}$H$_{27}$F$_3$N$_2$O$_3$ [M–H]$^-$=437.

Example 1E4

Preparation of Compound 5: N-((1R,2R)-1-(2,3-dihydrobenzo[β][1,4]dioxin-6-yl)-1-hydroxy-3-(pyrrolidin-1-yl)propan-2-yl)benzo[b]thiophene-2-carboxamide Compound 5 was prepared in a similar manner as described above, following Scheme 1.

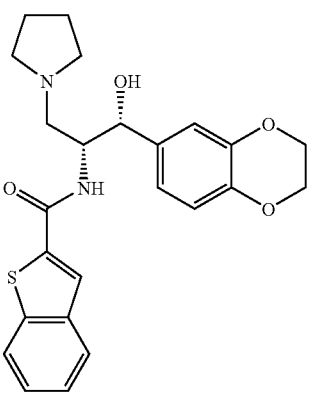 [SMILES: O=C(N[C@H](CN1CCCC1)[C@H](O)c1ccc2c(c1)OCCO2)c1cc2ccccc2s1]

$^1$H NMR (CDCl$_3$, 400 mHz, ppm); 1.8 (br, 4H), 2.7 (br, 4H), 3.0 (m, 2H), 4.25 (s, 4H), 4.45 (m, 1H), 5.05 (sd, 1H), 6.6

(br, 1H), 6.85 (s, 2H), 6.95 (s, 1H), 7.4 (m, 2H), 7.7 (s, 1H), 7.85 (m, 2H). M/Z for $C_{24}H_{26}N_2O_4S$ [M−H]$^-$=439.

Example 1E5

Preparation of Compound 11: N-((1R,2R)-1-(2,3-dihydrobenzo[β][1,4]dioxin-6-yl)-1-hydroxy-3-(pyrrolidin-1-yl)propan-2-yl)-2-(phenylthio)acetamide Compound 11 was prepared in a similar manner as described above, following Scheme 1.

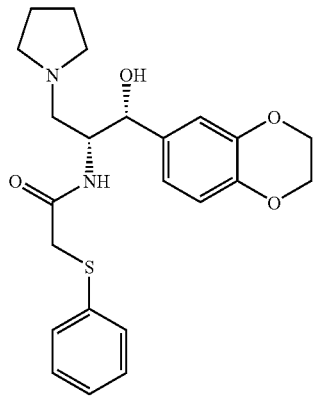 [SMILES: O=C(CSc1ccccc1)N[C@H](CN1CCCC1)[C@H](O)c1ccc2c(c1)OCCO2]

$^1$H NMR (CDCl$_3$, 400 mHz, ppm); 1.7 (br, 4H), 2.5 (br, 4H), 2.8 (br, 2H), 3.6 (q, 2H), 4.1.5 (m, 1H), 4.2 (s, 4H), 5.9 (sd, 1H), 6.7 (m, 2H), 6.8 (s, 1H), 7.2 (m, 7H). M/Z for $C_{23}H_{28}N_2O_4S$ [M−H]$^-$=429.

Example 1E6

Preparation of Compound 12: N-((1R,2R)-1-(2,3-dihydrobenzo[β][1,4]dioxin-6-yl)-1-hydroxy-3-(pyrrolidin-1-yl)propan-2-yl)biphenyl-4-carboxamide Compound 12 was prepared in a similar manner as described above, following Scheme 1.

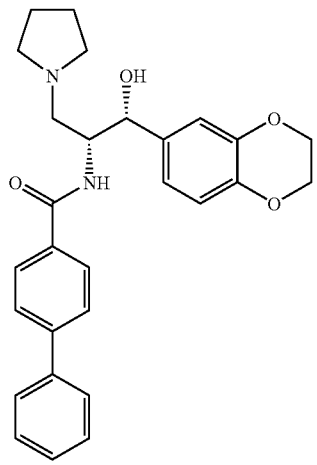 [SMILES: O=C(N[C@H](CN1CCCC1)[C@H](O)c1ccc2c(c1)OCCO2)c1ccc(-c2ccccc2)cc1]

$^1$H NMR (CDCl$_3$, 400 mHz, ppm); 1.8 (br, 4H), 2.7 (br, 4H), 3.0 (m, 2H), 4.25 (s, 4H), 4.4 (br, 1H), 5.05 (sd, 1H), 6.6 (sd, 1H), 6.85 (m, 2H), 6.95 (s, 1H), 7.45 (m, 3H), 7.6 (m, 4H), 7.75 (m, 2H). M/Z for $C_{28}H_{30}N_2O_4$ [M−H]$^-$=459.

Example 1E7

Preparation of Compound 19: N-((1R,2R)-1-(2,3-dihydrobenzo[β][1,4]dioxin-6-yl)-1-hydroxy-3-(pyrrolidin-1-yl)propan-2-yl)benzo[b]thiophene-5-carboxamide Compound 19 was prepared in a similar manner as described above, following Scheme 1.

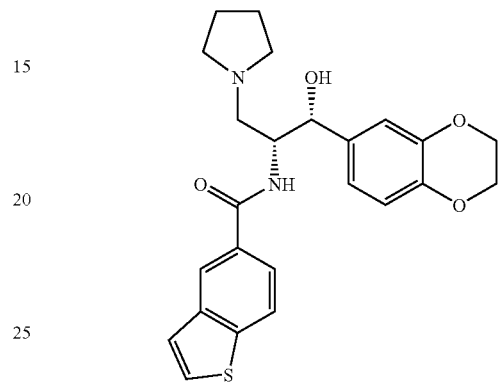

$^1$H NMR (d$_6$-dmso, 400 mHz, ppm); 1.6 (br, 4H), 2.4 (br, 5H), 2.65 (m, 1H), 4.15 (s, 4H), 4.25 (m, 1H), 4.75 (sd, 1H), 5.6 (br, 1H), 6.7 (m, 3H), 7.5 (sd, 1H), 7.7 (sd, 1H), 7.8 (sd, 1H), 7.85 (sd, 1H), 8.0 (sd, 1H), 8.2 (s, 1H). M/Z for $C_{24}H_{26}N_2O_4S$ [M−H]$^-$=439.

Example 1E8

Preparation of Compound 23: 2-(biphenyl-4-yl)-N-((1R,2R)-1-(2,3-dihydrobenzo[β][1,4]dioxin-6-yl)-1-hydroxy-3-(pyrrolidin-1-yl)propan-2-yl)acetamide Compound 23 was prepared in a similar manner as described above, following Scheme 1.

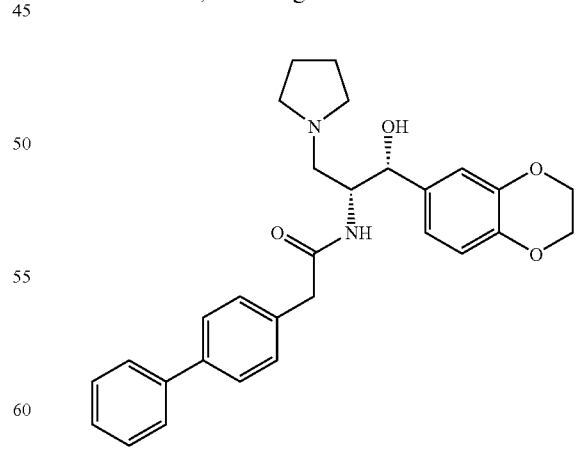

$^1$H NMR (CDCl$_3$, 400 mHz, ppm); 1.7 (br, 4H), 2.5 (br, 4H), 2.8 (d, 2H), 3.55 (s, 2H), 4.2 (m, 5H), 4.85 (sd, 1H), 5.95 (br, 1H), 6.6 (m, 1H), 6.75 (m, 2H), 7.2 (sd, 2H), 7.4 (m, 1H), 7.5 (st, 2H), 7.6 (m, 4H). M/Z for $C_{29}H_{32}N_2O_4$ [M−H]$^-$=473

Example 1E9

Preparation of Compound 24: N-((1R,2R)-1-(2,3-dihydrobenzo[β][1,4]dioxin-6-yl)-1-hydroxy-3-(pyrrolidin-1-yl)propan-2-yl)-2(4-phenoxyphenyl)acetamide Compound 24 was prepared in a similar manner as described above, following Scheme 1.

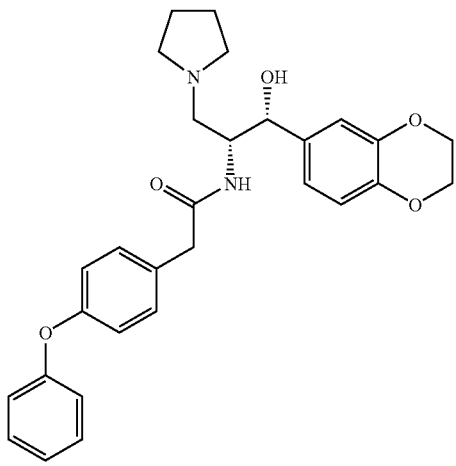 [SMILES: O=C(Cc1ccc(Oc2ccccc2)cc1)N[C@H](CN1CCCC1)[C@H](O)c1ccc2c(c1)OCCO2]

$^1$H NMR (CDCl$_3$, 400 mHz, ppm); 1.8 (br, 4H), 2.6 (br, 41-1), 2.8 (sd, 2H), 3.45 (s, 2H), 4.15 (m, 1H), 4.25 (s, 4H), 4.85 (sd, 1H), 5.9 (br, 1H), 6.6 (m, 1H), 6.7 (s, 1H), 6.8 (m, 1H), 7.15 (m, 7H), 7.4 (m, 2H). M/Z for C$_{29}$H$_{32}$N$_2$O$_5$ [M−H]$^-$=489.

Example 1E10

Preparation of Compound 25: (S)—N-((1R,2R)-1-(2,3-dihydrobenzo[β][1,4]dioxin-6-yl)-1-hydroxy-3-(pyrrolidin-1-yl)propan-2-yl)-2-hydroxy-3-phenyl-propanamide Compound 25 was prepared in a similar manner as described above, following Scheme 1.

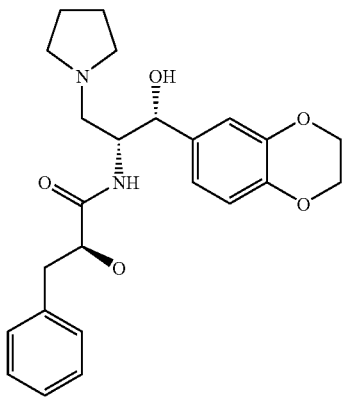 [SMILES: O=C(N[C@H](CN1CCCC1)[C@H](O)c1ccc2c(c1)OCCO2)[C@@H](O)Cc1ccccc1]

$^1$H NMR (CDCl$_3$, 400 mHz, ppm); 1.8 (br, 4H), 2.65 (br, 7H), 3.1 (dd, 2H), 4.2 (m, 6H), 4.8 (sd, 1H), 6.6 (m, 1H), 6.8 (m, 3H), 7.3 (m, 5H). M/Z for C$_{24}$H$_{30}$N$_2$O$_5$ [M−H]$^-$=427.

Example 1E11

Preparation of Compound 27: N-((1R,2R)-1-(2,3-dihydrobenzo[β][1,4]dioxin-6-yl)-1-hydroxy-3-(pyrrolidin-1-yl)propan-2-yl)-3-phenoxypropanamide Compound 27 was prepared in a similar manner as described above, following Scheme 1.

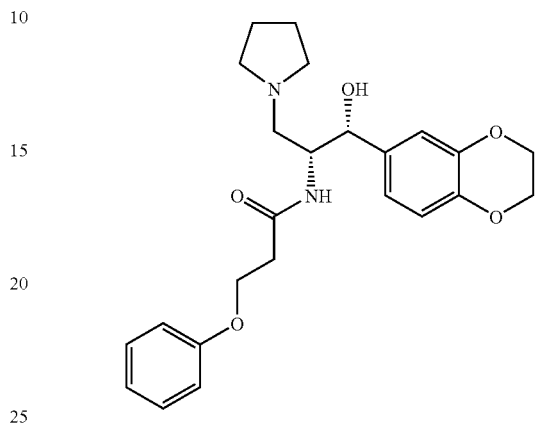

$^1$H NMR (CDCl$_3$, 400 mHz, ppm); 1.8 (br, 4H), 2.7 (br, 6H), 2.9 (m, 2H), 4.2 (m, 7H), 4.95 (sd, 1H), 6.45 (m, 1H), 6.75 (s, 1H), 6.85 (m, 3H), 6.95 (t, 1H), 7.2 (m, 3H). M/Z for C$_{24}$H30N$_2$O$_5$ [M−H]$^-$=427.

Example 1E12

Preparation of Compound 31: N-((1R,2R)-1-(2,3-dihydrobenzo[β][1,4]dioxin-6-yl)-1-hydroxy-3-(pyrrolidin-1-yl)propan-2-yl)-2-oxo-2-phenylacetamide Compound 31 was prepared in a similar manner as described above, following Scheme 1.

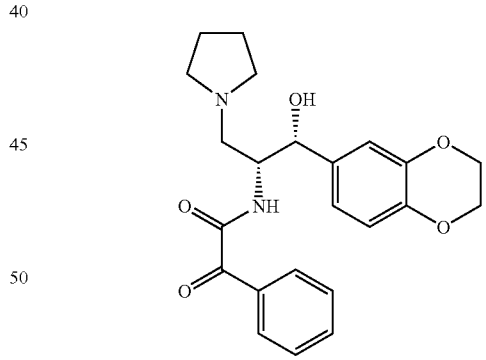

$^1$H NMR (CDCl$_3$, 400 mHz, ppm); 1.8 (br, 4H), 2.8 (br, 4H), 3.0 (m, 2H), 4.2 (s, 4H), 4.3 (m, 1H), 5.05 (sd, 1H), 6.8 (s, 2H), 6.9 (s, 1H), 7.35 (m, 1H), 7.45 (t, 2H), 7.6 (t, 1H) 8.2 (d, 2H). M/Z for C$_{23}$H$_{26}$N$_2$O$_5$ [M−H]$^-$=411.

Example 1E13

Preparation of Compound 32: N-((1R,2R)-1-(2,3-dihydrobenzo[β][1,4]dioxin-6-yl)-1-hydroxy-3-(pyrrolidin-1-yl)propan-2-yl)-3-(phenylthio)propanamide Compound 32 was prepared in a similar manner as described above, following Scheme 1.

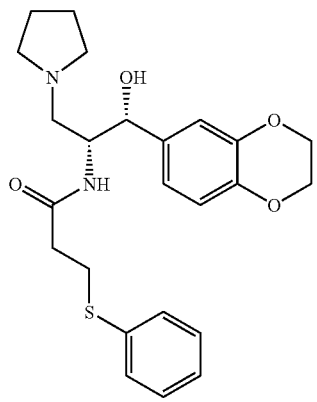 [SMILES: O=C(CCSc1ccccc1)N[C@H](CN1CCCC1)[C@H](O)c1ccc2c(c1)OCCO2]

$^{1}$H NMR (CDCl$_3$, 400 mHz, ppm); 1.8 (br, 4H), 2.4 (t, 2H), 2.7 (br, 4H), 2.8 (m, 2H), 3.1 (m, 2H), 4.2 (m, 5H), 4.9 (sd, 1H), 5.95 (br, 1H), 6.8 (m, 3H), 7.2 (m, 1H), 7.3 (m, 3H). M/Z for C$_{24}$H$_{30}$N$_2$O$_4$S [M−H]$^-$=443.

Example 1E14

Preparation of Compound 35: N-((1R,2R)-1-(2,3-dihydrobenzo[β][1,4]dioxin-6-yl)-1-hydroxy-3-(pyrrolidin-1-yl)propan-2-yl)-2-o-tolylacetamide Compound 35 was prepared in a similar manner as described above, following Scheme 1.

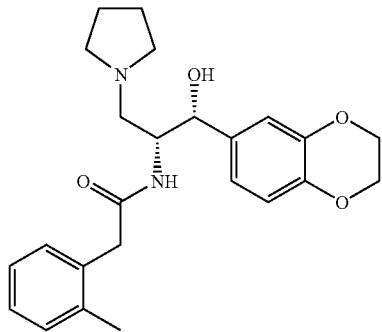 [SMILES: Cc1ccccc1CC(=O)N[C@H](CN1CCCC1)[C@H](O)c1ccc2c(c1)OCCO2]

$^{1}$H NMR (CDCl$_3$, 400 mHz, ppm); 1.7 (br, 4H), 2.1 (s, 3H), 2.5 (br, 4H), 2.75 (m, 2H), 3.5 (s, 2H), 4.1 (m, 1H), 4.25 (s, 4H), 4.8 (sd, 1H), 5.75 (br, 1H), 6.5 (d, 1H), 6.65 (s, 1H), 6.75 (d, 1H), 7.1 (d, 1H), 7.2 (m, 3H). M/Z for C$_{24}$H$_{30}$N$_2$O$_4$ [M−H]$^-$=411.

Example 1E15

Preparation of Compound 36: N-((1R,2R)-1-(2,3-dihydrobenzo[b][1,4]dioxin-6-yl)-1-hydroxy-3-(pyrrolidin-1-yl)propan-2-yl)-2-m-tolylacetamide Compound 36 was prepared in a similar manner as described above, following Scheme 1.

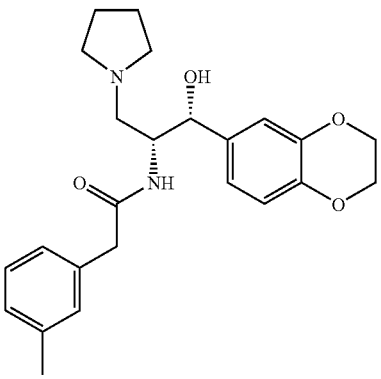 [SMILES: Cc1cccc(CC(=O)N[C@H](CN2CCCC2)[C@H](O)c2ccc3c(c2)OCCO3)c1]

$^{1}$H NMR (CDCl$_3$, 400 mHz, ppm); 1.7 (br, 4H), 2.35 (s, 3H), 2.5 (br, 4H), 2.75 (m, 2H), 3.45 (s, 2H), 4.1 (m, 1H), 4.25 (s, 4H), 4.85 (sd, 1H), 5.8 (br, 1H), 6.55 (d, 1H), 6.75 (m, 2H), 6.9 (d, 2H), 7.1 (sd, 1H), 7.2 (m, 1H). M/Z for C$_{24}$H$_{30}$N$_2$O$_4$ [M−H]$^-$=411.

Example 1E16

Preparation of Compound 39: 2-(benzylthio)-N-((1R,2R)-1-(2,3-dihydrobenzo[β][1,4]dioxin-6-yl)-1-hydroxy-3-(pyrrolidin-1-yl)propan-2-yl)acetamide Compound 39 was prepared in a similar manner as described above, following Scheme 1.

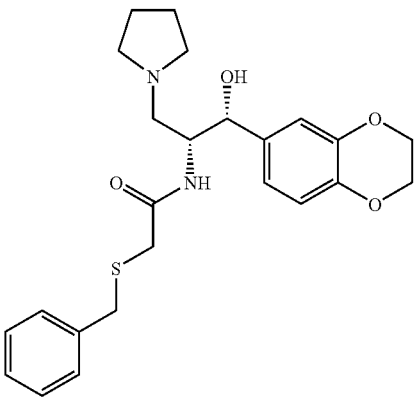 [SMILES: O=C(CSCc1ccccc1)N[C@H](CN1CCCC1)[C@H](O)c1ccc2c(c1)OCCO2]

$^{1}$H NMR (CDCl$_3$, 400 mHz, ppm); 1.8 (br, 4H), 2.7 (br, 4H), 2.9 (m, 2H), 3.0 (m, 2H), 3.3 (d, 1H), 3.55 (d, 1H), 4.2 (m, 5H), 5.05 (sd, 1H), 6.85 (s, 2H), 6.9 (s, 1H), 7.1 (sd, 2H), 7.3 (m, 3H). M/Z for C$_{24}$H$_{30}$N$_2$O$_4$S [M−H]$^-$=443.

Example 1E17

Preparation of Compound 47: N-((1R,2R)-1-(2,3-dihydrobenzo[β][1,4]dioxin-6-yl)-1-hydroxy-3-(pyrrolidin-1-yl)propan-2-yl)-2-(4-(pyridin-3-yl)phenyl)acetamide Compound 47 was prepared in a similar manner as described above, following Scheme 1.

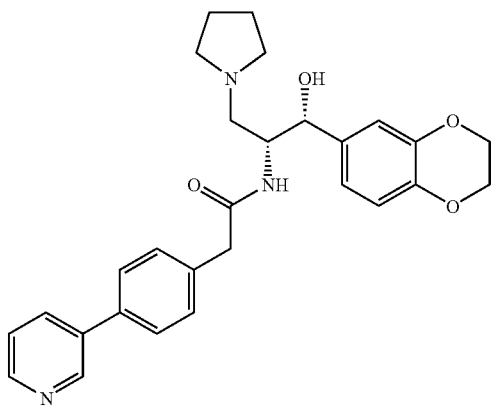 [SMILES: O=C(Cc1ccc(-c2cccnc2)cc1)N[C@H](CN1CCCC1)[C@H](O)c1ccc2c(c1)OCCO2]

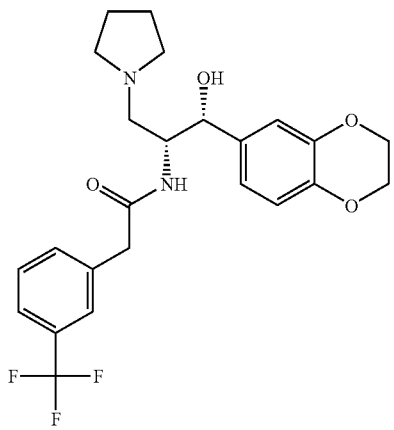

¹H NMR (CDCl₃, 400 mHz, ppm); 1.7 (br, 4H), 2.6 (br, 4H), 2.8 (sd, 2H), 3.55 (s, 2H), 4.15 (m, 1H), 4.2 (s, 4H), 4.85 (sd, 1H), 5.85 (br, 1H), 6.6 (d, 1H), 6.75 (m, 2H), 7.25 (d, 3H), 7.4 (m, 1H), 7.6 (sd, 2H), 7.9 (sd, 1H), 8.6 (sd, 1H), 8.85 (s, 1H). M/Z for $C_{28}H_{31}N_3O_4$ [M–H]⁻=474.

Example 1E18

Preparation of Compound 48: 2-(4'-chlorobiphenyl-4-yl)-N-((1R,2R)-1-(2,3-dihydrobenzo[β][1,4]dioxin-6-yl)-1-hydroxy-3-(pyrrolidin-1-yl)propan-2-yl)acetamide Compound 48 was prepared in a similar manner as described above, following Scheme 1.

¹H NMR (CDCl₃, 400 mHz, ppm); 1.7 (br, 4H), 2.55 (br, 4H), 2.8 (sd, 2H), 3.55 (s, 2H), 4.15 (m, 1H), 4.25 (s, 4H), 4.85 (sd, 1H), 5.8 (br, 1H), 6.6 (d, 1H), 6.75 (m, 2H), 7.35 (d, 1H), 7.45 (m, 2H), 7.55 (sd, 1H). M/Z for $C_{24}H_{27}F_3N_2O_4$ [M–H]⁻=465.

Example 1E20

Preparation of Compound 53: N-((1R,2R)-1-(2,3-dihydrobenzo[β][1,4]dioxin-6-yl)-1-hydroxy-3-(pyrrolidin-1-yl)propan-2-yl)-2-(3-fluorophenyl)acetamide Compound 53 was prepared in a similar manner as described above, following Scheme 1.

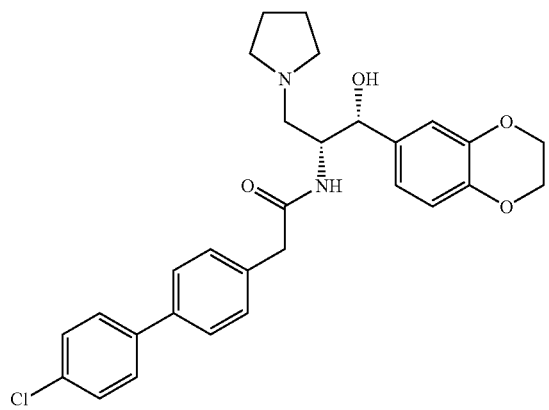 [SMILES: O=C(Cc1ccc(-c2ccc(Cl)cc2)cc1)N[C@H](CN1CCCC1)[C@H](O)c1ccc2c(c1)OCCO2]

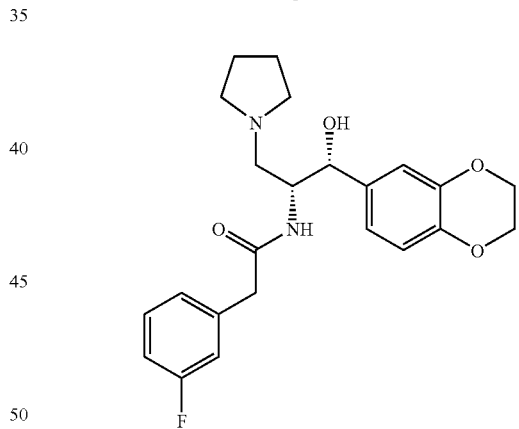

¹H NMR (CDCl₃, 400 mHz, ppm); 1.75 (br, 4H), 2.55 (br, 4H), 2.8 (sd, 2H), 3.55 (s, 2H), 4.15 (m, 1H), 4.2 (s, 4H), 4.85 (sd, 1H), 5.8 (br, 1H), 6.6 (d, 1H), 6.75 (m, 2H), 7.2 (d, 2H), 7.4 (m, 2H), 7.55 (sd, 4H). M/Z for $C_{29}H_{31}ClN_2O_4$ [M–H]⁻=508.

Example 1E19

Preparation of Compound 51: N-((1R,2R)-1-(2,3-dihydrobenzo[β][1,4]dioxin-6-yl)-1-hydroxy-3-(pyrrolidin-1-yl)propan-2-yl)-2-(3-(trifluoromethyl)phenyl)acetamide Compound 51 was prepared in a similar manner as described above, following Scheme 1.

¹H NMR (CDCl₃, 400 mHz, ppm); 1.7 (br, 4H), 2.55 (br, 4H), 2.8 (sd, 2H), 3.50 (s, 2H), 4.15 (m, 1H), 4.25 (s, 4H), 4.85 (sd, 1H), 5.8 (br, 1H), 6.6 (d, 1H), 6.75 (m, 1H), 6.8 (d, 1H), 6.85 (d, 1H), 6.9 (d, 1H), 7.0 (t, 1H), 7.3 (sq, 1H). M/Z for $C_{23}H_{27}FN_2O_4$ [M–H]⁻=415.

Example 1E21

Preparation of Compound 54: N-((1R,2R)-1-(2,3-dihydrobenzo[β][1,4]dioxin-6-yl)-1-hydroxy-3-(pyrrolidin-1-yl)propan-2-yl)-3-(3-methoxyphenoxy)propanamide Compound 54 was prepared in a similar manner as described above, following Scheme 1.

49

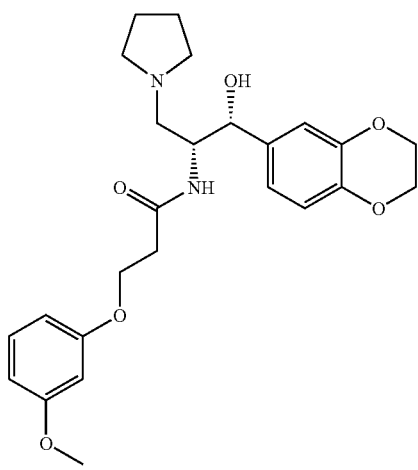 [SMILES: COc1cccc(OCCC(=O)N[C@H](CN2CCCC2)[C@H](O)c2ccc3c(c2)OCCO3)c1]

¹H NMR (CDCl₃, 400 mHz, ppm); 1.7 (br, 4H), 2.65 (br, 6H), 2.85 (m, 2H), 3.80 (s, 3H), 4.2 (m, 7H), 4.95 (sd, 1H), 6.45 (m, 4H), 6.75 (s, 2H), 6.85 (s, 1H), 7.2 (t, 1H). M/Z for $C_{25}H_{32}N_2O_6$ [M–H]⁻=457.

Example 1E22

Preparation of Compound 55: 3-(2,5-dichlorophenoxy)-N-((1R,2R)-1-(2,3-dihydrobenzo[β][1,4]dioxin-6-yl)-1-hydroxy-3-(pyrrolidin-1-yl)propan-2-yl)propanamide Compound 55 was prepared in a similar manner as described above, following Scheme 1.

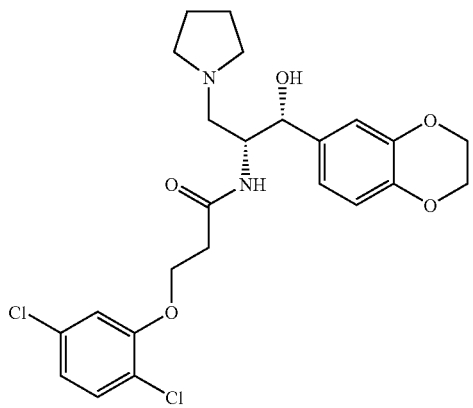 [SMILES: O=C(CCOc1cc(Cl)ccc1Cl)N[C@H](CN1CCCC1)[C@H](O)c1ccc2c(c1)OCCO2]

¹H NMR (CDCl₃, 400 mHz, ppm); 1.8 (br, 4H), 2.65 (br, 6H), 2.8 (m, 2H), 4.1 (m, 1H), 4.25 (m, 6H), 4.95 (sd, 1H), 6.3 (br, 1H), 6.75 (s, 2H), 6.8 (s, 1H), 6.9 (m, 2H), 7.25 (m, 1H). M/Z for $C_{24}H_{28}Cl_2N_2O_5$ [M–H]⁻=496.

Example 1E23

Preparation of Compound 57: 3-(4-chlorophenoxy)-N-((1R,2R)-1-(2,3-dihydrobenzo[β][1,4]dioxin-6-yl)-1-hydroxy-3-(pyrrolidin-1-yl)propan-2-yl)propanamide Compound 57 was prepared in a similar manner as described above, following Scheme 1.

50

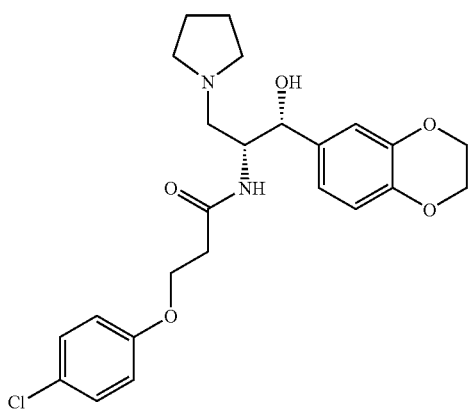 [SMILES: O=C(CCOc1ccc(Cl)cc1)N[C@H](CN1CCCC1)[C@H](O)c1ccc2c(c1)OCCO2]

¹H NMR (CDCl₃, 400 mHz, ppm); 1.75 (br, 4H), 2.65 (br, 6H), 2.8 (m, 2H), 4.2 (m, 7H), 4.95 (sd, 1H), 6.3 (br, 1H), 6.8 (m, 5H), 7.2 (m, 2H). M/Z for $C_{24}H_{29}ClN_2O_5$ [M–H]⁻=461.

Example 1E24

Preparation of Compound 58: N-((1R,2R)-1-(2,3-dihydrobenzo[β][1,4]dioxin-6-yl)-1-hydroxy-3-(pyrrolidin-1-yl)propan-2-yl)-3-(4-fluorophenoxy)propanamide Compound 58 was prepared in a similar manner as described above, following Scheme 1.

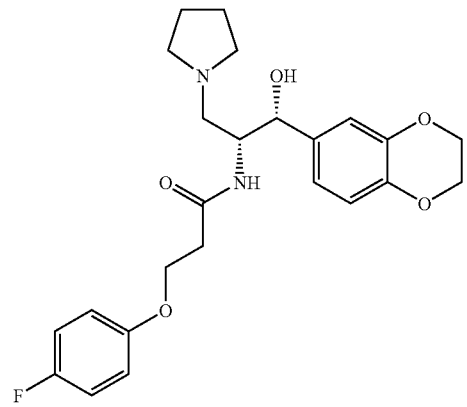 [SMILES: O=C(CCOc1ccc(F)cc1)N[C@H](CN1CCCC1)[C@H](O)c1ccc2c(c1)OCCO2]

¹H NMR (CDCl₃, 400 mHz, ppm); 1.75 (br, 4H), 2.65 (br, 6H), 2.8 (m, 2H), 4.2 (m, 7H), 4.95 (sd, 1H), 6.4 (br, 1H), 6.8 (m, 5H), 7.0 (m, 2H). M/Z for $C_{24}H_{29}FN_2O_5$ [M–H]⁻=445.

Example 1E25

Preparation of Compound 59: N-((1R,2R)-1-(2,3-dihydrobenzo[β][1,4]dioxin-6-yl)-1-hydroxy-3-(pyrrolidin-1-yl)propan-2-yl)-3-(p-tolyloxy)propanamide Compound 59 was prepared in a similar manner as described above, following Scheme 1.

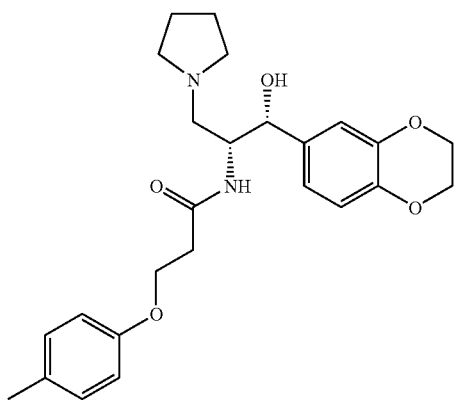 [SMILES: Cc1ccc(OCCC(=O)N[C@H](CN2CCCC2)[C@H](O)c2ccc3c(c2)OCCO3)cc1]

¹H NMR (CDCl₃, 400 mHz, ppm); 1.75 (br, 4H), 2.3 (s, 3H), 2.65 (br, 6H), 2.8 (m, 2H), 4.2 (m, 7H), 4.95 (sd, 1H), 6.45 (br, 1H), 6.75 (m, 4H), 6.85 (s, 1H), 7.1 (m, 2H). M/Z for $C_{25}H_{32}N_2O_5$ [M–H]⁻=441.

Example 1E26

Preparation of Compound 60: N-((1R,2R)-1-(2,3-dihydrobenzo[β][1,4]dioxin-6-yl)-1-hydroxy-3-(pyrrolidin-1-yl)propan-2-yl)-3-(2-fluorophenoxy)propanamide Compound 60 was prepared in a similar manner as described above, following Scheme 1.

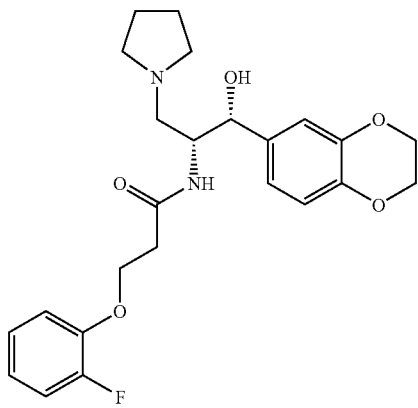 [SMILES: O=C(CCOc1ccccc1F)N[C@H](CN1CCCC1)[C@H](O)c1ccc2c(c1)OCCO2]

¹H NMR (CDCl₃, 400 mHz, ppm); 1.75 (br, 4H), 2.65 (br, 6H), 2.75 (m, 2H), 4.2 (m, 7H), 4.95 (sd, 1H), 6.35 (br, 1H), 6.7 (s, 2H), 6.85 (s, 1H), 6.95 (m, 2H), 7.05 (m, 2H). M/Z for $C_{24}H_{29}FN_2O_5$ [M–H]⁻=445.

Example 1E27

Preparation of Compound 61: N-((1R,2R)-1-(2,3-dihydrobenzo[β][1,4]dioxin-6-yl)-1-hydroxy-3-(pyrrolidin-1-yl)propan-2-yl)-3-(4-methoxyphenoxy)propanamide Compound 61 was prepared in a similar manner as described above, following Scheme 1.

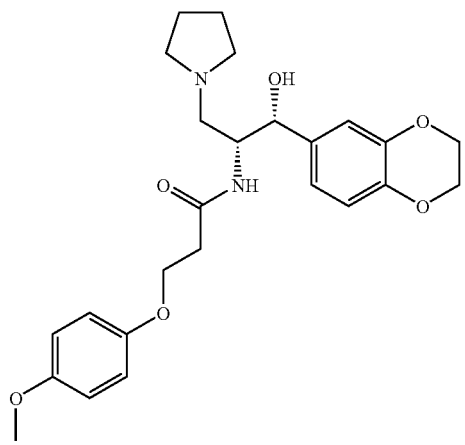 [SMILES: COc1ccc(OCCC(=O)N[C@H](CN2CCCC2)[C@H](O)c2ccc3c(c2)OCCO3)cc1]

¹H NMR (CDCl₃, 400 mHz, ppm); 1.75 (br, 4H), 2.65 (br, 6H), 2.75 (m, 2H), 3.8 (s, 3H), 4.1 (m, 2H), 4.2 (br, 5H), 4.95 (sd, 1H), 6.45 (br, 1H), 6.8 (m, 7H). M/Z for $C_{25}H_{32}N_2O_6$ [M–H]⁻=457.

Example 1E28

Preparation of Compound 188: N-((1R,2R)-1-(2,3-dihydrobenzo[β][1,4]dioxin-6-yl)-1-hydroxy-3-(pyrrolidin-1-yl)propan-2-yl)-3-(4-ethylphenoxy)propanamide(2R,3R)-2,3-dihydroxysuccinate Compound 188 was prepared in a similar manner as described above, following Scheme 1.

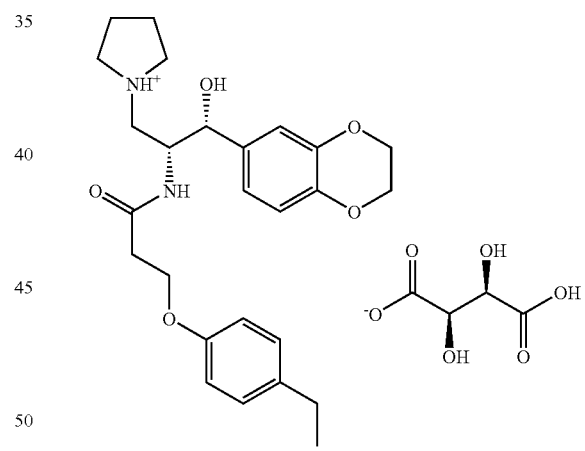

¹H NMR (D₂O, 400 mHz, ppm); 0.93 (t, 3H), 1.75 (br, 2H), 1.86 (br, 2H), 2.35 (q, 2H), 2.4 (br, 2H), 2.9 (br, 2H), 3.25 (m, 2H), 3.4 (br, 2H), 3.9 (br, 6H), 4.3 (br, 3H), 4.6 (br, 1H), 6.6 (m, 5H), 7.0 (d, 2H). M/Z for $C_{26}H_{34}N_2O_5 \cdot C_4H_6O_6$ [M–H]⁻=454.

Example 1E29

Preparation of Compound 189: N-((1R,2R)-1-(2,3-dihydrobenzo[b][1,4]dioxin-6-yl)-1-hydroxy-3-(pyrrolidin-1-yl)propan-2-yl)-3-(4-propionylphenoxy)propanamide(2R,3R)-2,3-dihydroxysuccinate Compound 189 was prepared in a similar manner as described above, following Scheme 1.

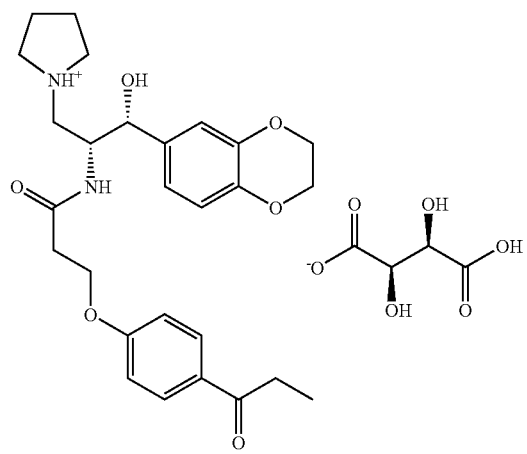

¹H NMR (D₂O, 400 mHz, ppm); 0.93 (t, 3H), 1.75 (br, 2H), 1.86 (br, 2H), 2.45 (br, 2H), 2.8 (q, 2H), 2.9 (br, 2H), 3.25 (m, 2H), 3.4 (br, 2H), 3.9 (br, 6H), 4.3 (br, 3H), 4.6 (br, 1H), 6.5 (d, 1H), 6.5 (d, 2H), 6.7 (d, 2H), 7.7 (d, 2H). M/Z for $C_{27}H_{34}N_2O_6 \cdot C_4H_6O_6$ [M−H]⁻=483.

Example 1E30

Preparation of Compound 193: N-((1R,2R)-1-(2,3-dihydrobenzo[b][1,4]dioxin-6-yl)-1-hydroxy-3-(pyrrolidin-1-yl)propan-2-yl)-3-(4-(3-oxobutyl)phenoxy)propanamide(2R,3R)-2,3-dihydroxysuccinate Compound 193 was prepared in a similar manner as described above, following Scheme 1.

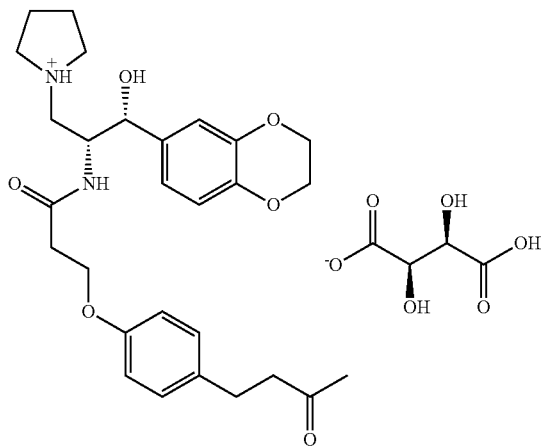

¹H NMR (D₂O, 400 mHz, ppm); 1.75 (br, 2H), 1.86 (br, 2H), 1.94 (s, 3H), 2.45 (br, 2H), 2.6 (m, 4H), 2.9 (br, 2H), 3.25 (m, 2H), 3.4 (br, 2H), 3.9 (br, 6H), 4.3 (br, 3H), 4.6 (br, 1H), 6.6 (m, 5H), 7.0 (d, 2H). M/Z for $C_{28}H_{36}N_2O_6 \cdot C_4H_6O_6$ [M−H]⁻=497.

Example 1E31

Preparation of Compound 202: N-((1R,R)-1-(2,3-dihydrobenzo[β][1,4]dioxin-6-yl)-1-hydroxy-3-(pyrrolidin-1-yl)propan-2-yl)-3-(4-(2-methoxyethyl)phenoxy)propanamide(2R,R)-2,3-dihydroxysuccinate Compound 202 was prepared in a similar manner as described above, following Scheme 1.

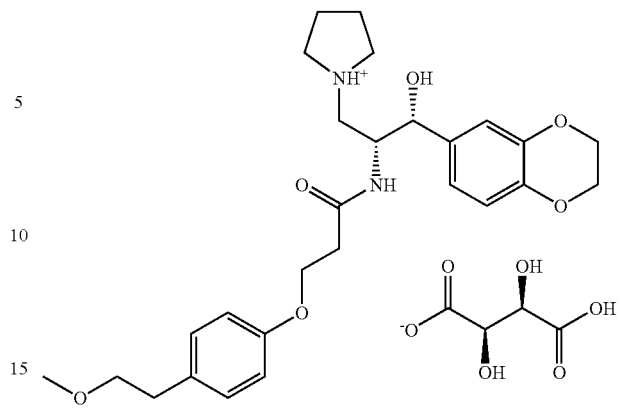

¹H NMR (D₂O, 400 mHz, ppm); 1.75 (br, 2H), 1.86 (br, 2H), 2.45 (br, 2H), 2.62 (t, 2H), 2.9 (br, 2H), 3.1 (s, 3H), 3.25 (m, 2H), 3.4 (br, 4H), 3.9 (br, 6H), 4.3 (br, 3H), 4.6 (br, 1H), 6.6 (m, 5H), 7.0 (d, 2H). M/Z for $C_{27}H_{36}N_2O_6 \cdot C_4H_6O_6$ [M−H]⁻=485.

Example 1E32

Preparation of Compound 63: N-((1R,2R)-1-(2,3-dihydrobenzo[β][1,4]dioxin-6-yl)-1-hydroxy-3-(pyrrolidin-1-yl)propan-2-yl)-2-(3'-methoxybiphenyl-4-yl)acetamide Compound 63 was prepared in a similar manner as described above, following Scheme 1.

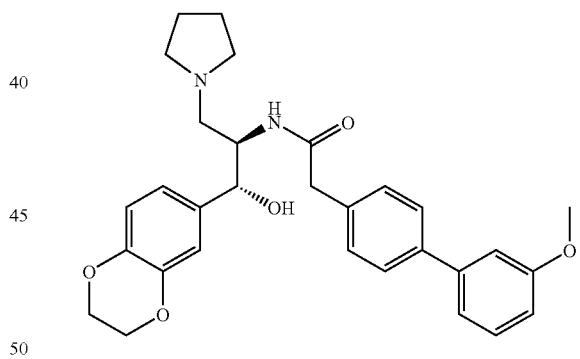

¹H NMR (CDCl₃, 400 mHz, ppm); 1.7 (br, 4H), 2.5 (br, 4H), 2.75 (m, 2H), 3.5 (br, 2H), 3.9 (sd, 3H), 4.2 (m, 5H), 4.95 (sd, 1H), 5.9 (br, 1H), 6.5-7.6 (m, 11H). M/Z for $C_{30}H_{34}N_2O_5$ [M−H]⁻=503.

Example 1E33

Preparation of Compound 127: N-((1R,2R)-1-(2,3-dihydrobenzo[b][1,4]dioxin-6-yl)-1-hydroxy-3-(pyrrolidin-1-yl)propan-2-yl)-4-(4-ethoxyphenyl)-4-oxobutanamide Compound 127 was prepared in a similar manner as described above, following Scheme 1.

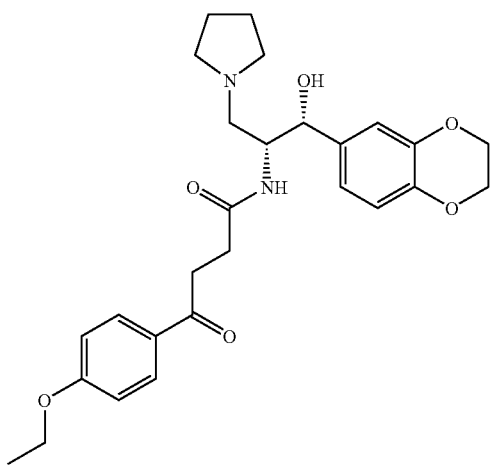 [SMILES: CCOc1ccc(C(=O)CCC(=O)N[C@H](CN2CCCC2)[C@H](O)c2ccc3c(c2)OCCO3)cc1]

¹H NMR (CDCl₃, 400 mHz, ppm); 1.4 (t, 3H), 1.8 (br, 4H), 2.7 (br, 6H), 3.2 (m, 2H), 4.05 (q, 2H), 4.2 (m, 2H), 4.25 (m, 5H), 4.95 (sd, 1H), 6.05 (br, 1H), 6.9 (m, 5H), 7.95 (d, 2H). M/Z for $C_{27}H_{34}N_2O_6$ [M–H]⁻=483.

Example 1E34

Preparation of Compound 154: N-((1R,2R)-1-(2,3-dihydrobenzo[b][1,4]dioxin-6-yl)-1-hydroxy-3-(pyrrolidin-1-yl)propan-2-yl)-4-(4-methoxyphenyl)-4-oxobutanamide Compound 154 was prepared in a similar manner as described above, following Scheme 1.

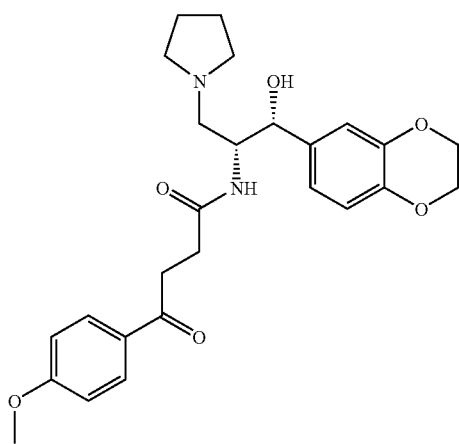 [SMILES: COc1ccc(C(=O)CCC(=O)N[C@H](CN2CCCC2)[C@H](O)c2ccc3c(c2)OCCO3)cc1]

¹H NMR (CDCl₃, 400 mHz, ppm); 1.8 (br, 4H), 2.7 (br, 6H), 3.2 (m, 1H), 3.45 (s, 3H), 3.9 (s, 3H), 4.2 (m, 5H), 4.95 (sd, 1H), 6.05 (br, 1H), 6.9 (m, 5H), 7.95 (d, 2H). M/Z for $C_{26}H_{32}N_2O_6$ [M–H]⁻=469.

Example 1E35

Preparation of Compound 181: N-((1R,2R)-1-(2,3-dihydrobenzo[b][1,4]dioxin-6-yl)-1-hydroxy-3-(pyrrolidin-1-yl)propan-2-yl)-6-(4-isopropoxyphenyl)-6-oxohexanamide Compound 181 was prepared in a similar manner as described above, following Scheme 1.

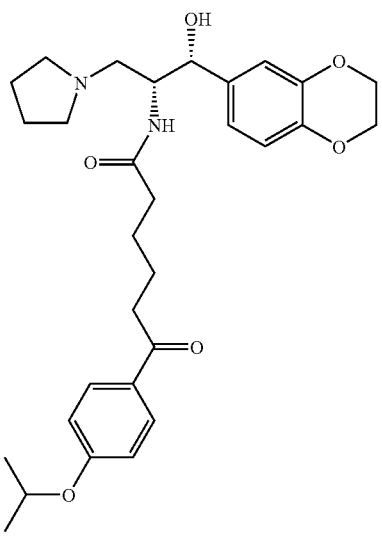 [SMILES: CC(C)Oc1ccc(C(=O)CCCCC(=O)N[C@H](CN2CCCC2)[C@H](O)c2ccc3c(c2)OCCO3)cc1]

¹H NMR (CDCl₃, 400 mHz, ppm); 1.4 (d, 6H), 1.8 (br, 8H), 2.15 (br, 2H), 2.8 (br, 10H), 4.25 (m, 5H), 4.65 (m, 1H), 4.95 (sd, 1H), 6.05 (br, 1H), 6.9 (m, 5H), 7.95 (d, 2H). M/Z for $C_{30}H_{40}N_2O_6$ [M–H]⁻=525.

Example 1E36

Preparation of Compound 191: N-((1R,2R)-1-(2,3-dihydrobenzo[β][1,4]dioxin-6-yl)-1-hydroxy-3-(pyrrolidin-1-yl)propan-2-yl)-5-(4-methoxyphenyl)-5-oxopentanamide(2R,3R)-2,3-dihydroxysuccinate Compound 191 was prepared in a similar manner as described above, following Scheme 1.

¹H NMR (D₂O, 400 mHz, ppm); 1.40 (br, 1H), 1.53 (br, 1H), 1.75 (br, 2H), 1.91 (br, 2H), 1.98 (m, 1H), 2.15 (m, 1H) 2.45 (m, 2H), 2.95 (m, 2H), 3.35 (dd, 2H), 3.4 (m, 2H), 3.68 (br, 5H), 3.77 (br, 2H), 4.3 (br, 3H), 4.68 (br, 1H), 6.47 (d, 1H), 6.65 (d, 2H), 6.85 (d, 2H), 7.63 (d, 2H). M/Z for $C_{27}H_{34}N_2O_6 \cdot C_4H_6O_6$ [M–H]=483

Example 1E37

Preparation of Compound 265: N-((1R,2R)-1-(benzo[δ][1,3]dioxol-5-yl)-1-hydroxy-3-(pyrrolidin-1-yl)propan-2-yl)-5-(4-isopropoxyphenyl)-5-oxopentanamide(2S,3S)-2,3-dihydroxysuccinate Compound 265 was prepared in a similar manner as described above, following Scheme 1.

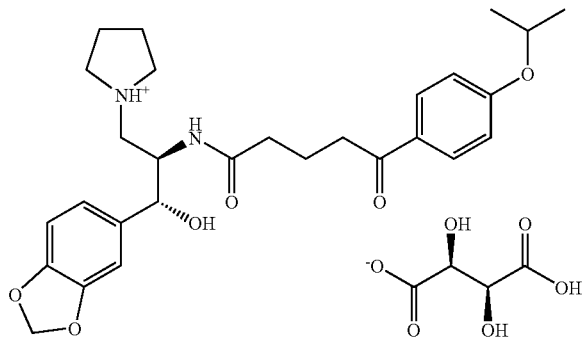

$^1$H NMR (400 MHz, CD$_3$OD) δ 1.30 (sd, 6H), 1.70-1.85 (m, 2H), 2.04 (br, 4H), 2.09-2.26 (m, 2H), 2.64-2.82 (m, 2H), 3.31-3.48 (m, 5H), 4.37 (s, 2H), 4.43 (br, 1H), 4.68 (m, 1H), 4.71 (sd, 1H), 5.76 (s, 2H), 6.66 (d, 1H), 6.82-6.95 (m, 4H), 7.84 (d, 2H); MS for C$_{28}$H$_{36}$N$_2$O$_6$·C$_4$H$_6$O$_6$: [M−H]$^-$ 645.

Example 1E38

Preparation of Compound 267: N-((1R,2R)-1-(benzo[δ][1,3]dioxol-5-yl)-1-hydroxy-3-(pyrrolidin-1-yl)propan-2-yl)-6-(4-methoxyphenyl)-6-oxohexanamide(2S,3S)-2,3-dihydroxysuccinate Compound 267 was prepared in a similar manner as described above, following Scheme 1.

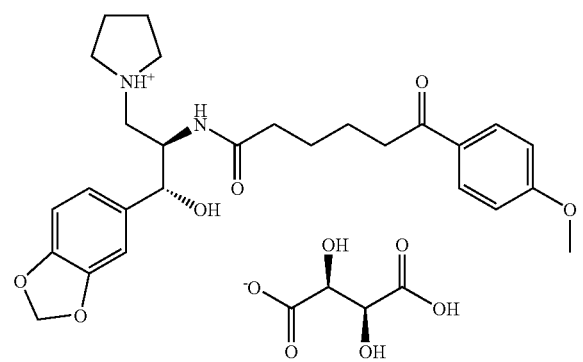

$^1$H NMR (400 MHz, CD$_3$OD) δ 1.49 (br, 4H), 2.03 (br, 4H), 2.89 (t, 2H), 3.33-3.46 (m, 6H), 3.84 (s, 3H), 4.37 (s, 2H), 4.43 (d, 1H), 4.76 (br, 1H), 5.81 (s, 2H), 6.68 (d, 1H), 6.81 (d, 1H), 6.88 (s, 1H), 6.96 (d, 2H), 7.92 (d, 2H); MS for C$_{27}$H$_{34}$N$_2$O$_6$·C$_4$H$_6$O$_6$: [M−H]$^-$ 633.

Example 1E39

Preparation of Compound 268: N-((1R,2R)-1-(benzo[δ][1,3]dioxol-5-yl)-1-hydroxy-3-(pyrrolidin-1-yl)propan-2-yl)-7-(4-isopropoxyphenyl)-7-oxoheptanamide(2S,3S)-2,3-dihydroxysuccinate Compound 268 was prepared in a similar manner as described above, following Scheme 1.

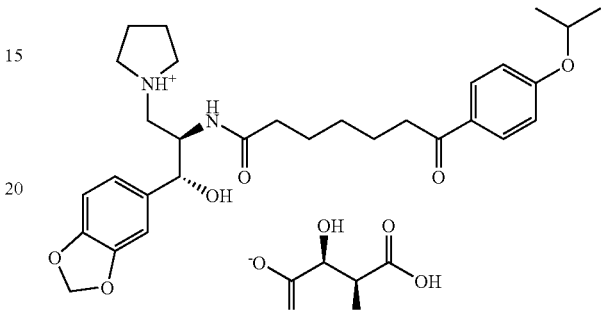

$^1$H NMR (400 MHz, CD$_3$OD) δ 1.15-1.18 (m, 2H), 1.30 (d, 6H), 1.40-1.45 (m, 2H), 1.57-1.65 (m, 2H), 2.03 (br, 4H), 2.12-2.17 (m, 2H), 2.88 (t, 2H), 3.33-3.48 (m, 5H), 4.38 (s, 2H), 4.42 (d, 1H), 4.67 (m, 1H), 4.78 (d, 1H), 5.83 (d, 2H), 6.71 (d, 1H), 6.82 (d, 1H), 6.89 (s, 1H), 6.92 (d, 2H), 7.90 (d, 2H); MS for C$_{30}$H$_{40}$N$_2$O$_6$·C$_4$H$_6$O$_6$: [M−H]$^-$ 675.

Example 1E40

Preparation of Compound 197: N-((1R,2R)-1-(2,3-dihydrobenzo[β][1,4]dioxin-6-yl)-1-hydroxy-3-(pyrrolidin-1-yl)propan-2-yl)-4-(4-methoxyphenoxy)butanamide(2S,3S)-2,3-dihydroxysuccinate Compound 197 was prepared in a similar manner as described above, following Scheme 1.

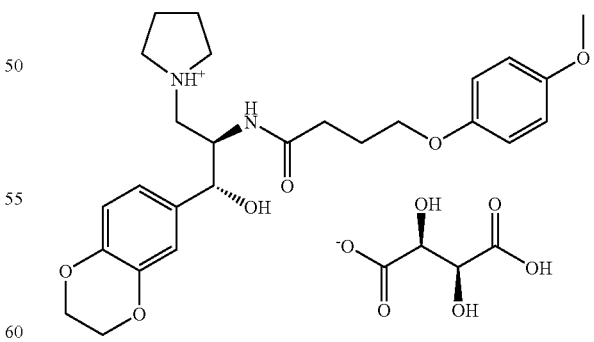

$^1$H NMR (400 MHz, CD$_3$OD) δ 1.78-1.91 (m, 2H), 2.00 (br, 4H), 2.32 (t, 2H), 3.33-3.47 (m, 6H), 3.69 (s, 3H), 3.72 (t, 2H), 4.11 (br, 4H), 4.37 (s, 2H), 4.41 (d, 1H), 4.72 (d, 1H), 6.69-6.86 (m, 7H); MS for C$_{26}$H$_{34}$N$_2$O$_6$·C$_4$H$_6$O$_6$: [M−H]$^-$ 621.

Example 1E41

Preparation of Compound 187: N-((1R,2R)-1-(2,3-dihydrobenzo[β][1,4]dioxin-6-yl)-1-hydroxy-3-(pyrrolidin-1-yl)propan-2-yl)-3-(4-(3-methylbutanoyl)phenoxy)propanamide(2S,3S)-2,3-dihydroxysuccinate Compound 187 was prepared in a similar manner as described above, following Scheme 1.

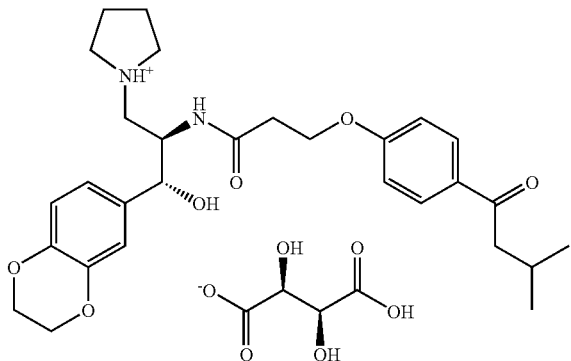

$^1$H NMR (400 MHz, CD$_3$OD) δ 0.95 (d, 6H), 2.00 (br, 4H), 2.17 (m, 2H), 2.66 (t, 2H), 2.78 (d, 2H), 3.34-3.44 (m, 5H), 4.12-4.17 (m, 6H), 4.40 (s, 2H), 4.45 (d, 1H), 4.73 (sd, 1H), 6.67 (d, 1H), 6.79 (d, 1H), 6.86 (s, 1H), 6.93 (d, 2H), 7.91 (d, 2H); MS for C$_{29}$H$_{38}$N$_2$O$_6$·C$_4$H$_6$O$_6$: [M−H]$^-$ 661.

Example 1E42

Preparation of Compound 83: 2-(4-chlorophenoxy)-N-((1R,2R)-1-(2,3-dihydrobenzo[β][1,4]dioxin-6-yl)-1-hydroxy-3-(pyrrolidin-1-yl)propan-2-yl)acetamide Compound 83 was prepared in a similar manner as described above, following Scheme 1.

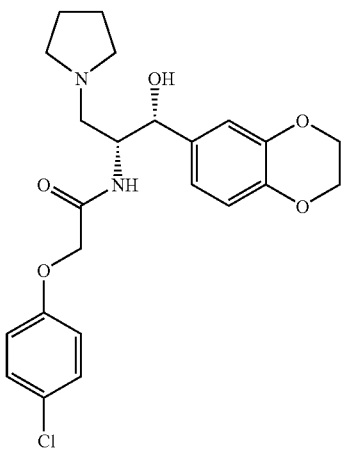 [SMILES: O=C(COc1ccc(Cl)cc1)N[C@H](CN1CCCC1)[C@H](O)c1ccc2c(c1)OCCO2]

$^1$H NMR (400 MHz, CDCl$_3$) δ 1.76 (br, 4H), 2.63 (br, 4H), 2.78 (dd, 1H), 2.89 (dd, 1H), 4.24 (s, 4H), 4.27 (br, 1H), 4.36 (q, 2H), 4.94 (d, 1H), 6.71 (d, 1H), 6.77-6.82 (m, 4H), 6.86 (d, 1H), 7.24 (s, 1H); MS for C$_{23}$H$_{27}$ClN$_2$O$_5$: [M−H]$^-$ 447.

Example 1E43

Preparation of Compound 87: 2-(3,4-dichlorophenoxy)-N-((1R,2R)-1-(2,3-dihydrobenzo[β][1,4]dioxin-6-yl)-1-hydroxy-3-(pyrrolidin-1-yl)propan-2-yl)acetamide Compound 87 was prepared in a similar manner as described above, following Scheme 1.

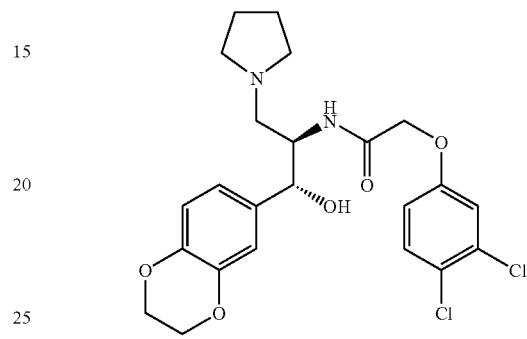

$^1$H NMR (400 MHz, CDCl$_3$) δ 1.78 (br, 4H), 2.67 (br, 4H), 2.79 (dd, 1H), 2.92 (dd, 1H), 4.25 (br, s, 5H), 4.35 (q, 2H), 4.95 (d, 1H), 6.71-6.84 (m, 5H), 7.01 (d, 1H), 7.34 (d, 1H); MS for C$_{23}$H$_{26}$Cl$_2$N$_2$O$_5$: [M−H]$^-$ 482.

Example 1E44

Preparation of Compound 86: N-((1R,2R)-1-(2,3-dihydrobenzo[b][1,4]dioxin-6-yl)-1-hydroxy-3-(pyrrolidin-1-yl)propan-2-yl)-2-(3-phenoxyphenyl)acetamide Compound 86 was prepared in a similar manner as described above, following Scheme 1.

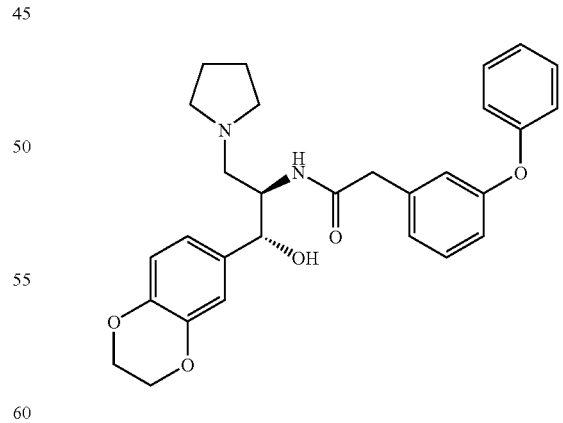

$^1$H NMR (400 MHz, CDCl$_3$) δ 1.72 (br, 4H), 2.57 (br, 4H), 2.75-2.80 (m, 2H), 3.45 (s, 2H), 4.11-4.13 (m, 1H), 4.23 (s, 4H), 4.84 (d, 1H), 5.86 (d, 1H), 6.55 (dd, 1H), 6.71 (d, 1H), 6.74 (d, 1H), 6.80 (br, 1H), 6.85 (dd, 1H), 6.92 (dd, 1H), 6.98 (d, 1H), 7.14 (t, 1H), 7.28-7.36 (m, 2H); MS for C$_{29}$H$_{32}$N$_2$O$_5$: [M−H]$^-$ 489.

Example 1E45

Preparation of Compound 280: 2-(3,4-difluorophenyl)-N-((1R,2R)-1-(2,3-dihydrobenzo[β][1,4]dioxin-6-yl)-1-hydroxy-3-(pyrrolidin-1-yl)propan-2-yl)acetamide Compound 280 was prepared in a similar manner as described above, following Scheme 1.

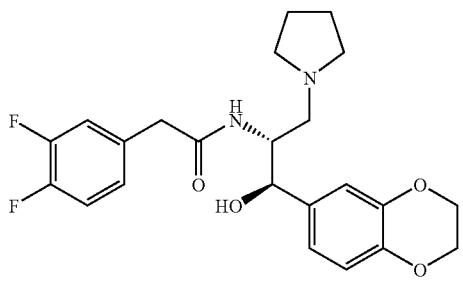 [SMILES: O=C(Cc1ccc(F)c(F)c1)N[C@H](CN1CCCC1)[C@H](O)c1ccc2c(c1)OCCO2]

$^1$H NMR (400 MHz, CDCl$_3$) δ 1.80 (br, 4H, 2.68 (br, 4H), 2.84 (d, 2H), 3.45 (s, 2H), 4.17 (m, 1H), 4.25 (s, 4H), 4.88 (d, 1H), 5.88 (d, 1H), 6.65 (d, 1H), 6.79 (d, 1H), 6.95 (m, 1H), 6.95 (t, 1H), 7.13 (q, 1H); MS for C$_{23}$H$_{26}$F$_2$N$_2$O$_4$: [M–H]$^-$ 434.

Example 1E46

Preparation of Compound 103: N-((1R,2R)-1-(2,3-dihydrobenzo[β][1,4]dioxin-6-yl)-1-hydroxy-3-(pyrrolidin-1-yl)propan-2-yl)-2-(4-(trifluoromethoxy)phenyl)acetamide Compound 103 was prepared in a similar manner as described above, following Scheme 1.

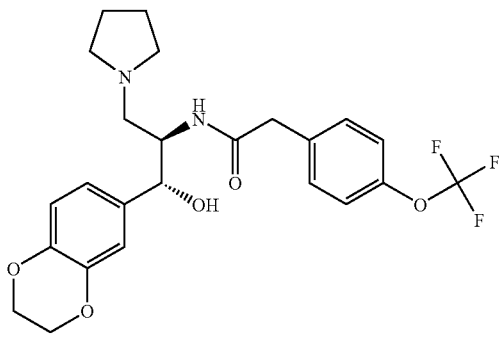 [SMILES: O=C(Cc1ccc(OC(F)(F)F)cc1)N[C@H](CN1CCCC1)[C@H](O)c1ccc2c(c1)OCCO2]

$^1$H NMR (400 MHz, CDCl$_3$) δ 1.65 (br, 4H), 2.48 (br, 4H), 2.69 (d, 2H), 3.40 (s, 2H), 4.08 (m, 1H), 4.17 (s, 4H), 4.80 (s, 1H), 5.84 (t, 1H), 6.55 (d, 1H), 6.66 (s, 1H), 6.70 (d, 1H), 7.10 (t, 3H); MS for C$_{24}$H$_{27}$F$_3$N$_2$O$_5$: [M–H]$^-$ 481.

Example 1E47

Preparation of Compound 90: N-((1R,2R)-1-(2,3-dihydrobenzo[β][1,4]dioxin-6-yl)-1-hydroxy-3-(pyrrolidin-1-yl)propan-2-yl)-5-(thiophen-2-yl)isoxazole-3-carboxamide Compound 90 was prepared in a similar manner as described above, following Scheme 1.

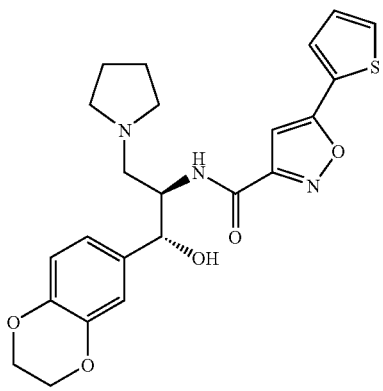 [SMILES: O=C(N[C@H](CN1CCCC1)[C@H](O)c1ccc2c(c1)OCCO2)c1cc(-c2cccs2)on1]

$^1$H NMR (400 MHz, CDCl$_3$) δ 1.82 (br, 4H), 2.73-2.81 (m, 4H), 2.89-2.93 (m, 1H), 3.02-3.07 (m, 1H), 4.23 (s, 4H), 4.41 (br, 1H), 5.07 (s, 1H), 5.30 (d, 1H), 6.74 (s, 1H), 6.83 (t, 2H), 6.90 (s, 1H), 7.12-7.14 (m, 2H), 7.47 (d, 1H), 7.52 (d, 1H); MS for C$_{23}$H$_{25}$N$_3$O$_5$S: [M–H]$^-$ 456.

Example 1E48

Preparation of Compound 92: 3-(3-chloro-4-methoxyphenyl)-N-((1R,2R)-1-(2,3-dihydrobenzo[β][1,4]dioxin-6-yl)-1-hydroxy-3-(pyrrolidin-1-yl)propan-2-yl)propanamide Compound 92 was prepared in a similar manner as described above, following Scheme 1.

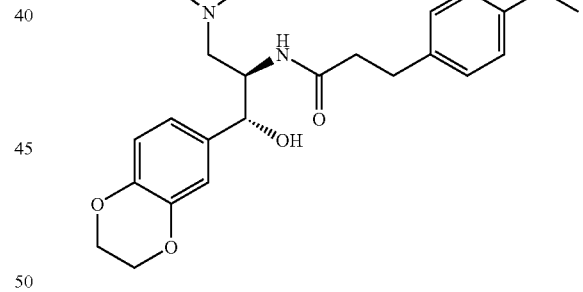

$^1$H NMR (400 MHz, CDCl$_3$) δ 1.77 (br, 4H), 2.38 (t, 2H), 2.60 (br, 4H), 2.8 (m, 4H), 3.86 (s, 3H), 4.20 (br, 1H), 4.24 (s, 4H), 4.87 (s, 1H), 5.80 (d, 1H), 6.66 (d, 1H), 6.8 (m, 3H), 7.00 (d, 1H), 7.18 (s, 1H); MS for C$_{25}$H$_{31}$ClN$_2$O$_5$: [M–H]$^-$ 475.

Example 1E49

Preparation of Compound 96: N-((1R,2R)-1-(2,3-dihydrobenzo[β][1,4]dioxin-6-yl)-1-hydroxy-3-(pyrrolidin-1-yl)propan-2-yl)-3-(4-(trifluoromethyl)phenyl)propanamide Compound 96 was prepared in a similar manner as described above, following Scheme 1.

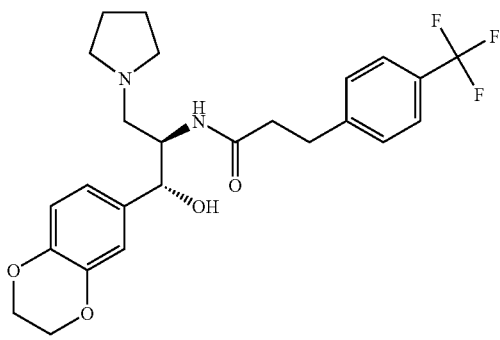 [SMILES: O=C(CCc1ccc(C(F)(F)F)cc1)N[C@H](CN1CCCC1)[C@H](O)c1ccc2c(c1)OCCO2]

¹H NMR (400 MHz, CDCl₃) δ 1.73 (br, 4H), 2.4 (m, 2H), 2.53 (m, 4H), 2.7 (m, 2H), 2.90-2.97 (m, 2H), 4.17 (br, 1H), 4.23 (s, 4H), 4.89 (s, 1H), 5.83 (br, 1H), 6.68 (d, 1H), 6.79 (d, 2H), 7.24 (d, 2H), 7.50 (d, 2H); MS for $C_{25}H_{29}F_3N_2O_5$: [M–H]⁻ 479.

Example 1E50

Preparation of Compound 101: 4-(benzo[d]thiazol-2-yl)-N-((1R,2R)-1-(2,3-dihydrobenzo[β][1,4]dioxin-6-yl)-1-hydroxy-3-(pyrrolidin-1-yl)propan-2-yl)butanamide Compound 101 was prepared in a similar manner as described above, following Scheme 1.

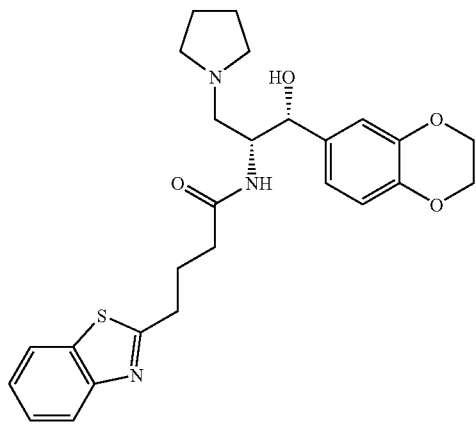 [SMILES: O=C(CCCc1nc2ccccc2s1)N[C@H](CN1CCCC1)[C@H](O)c1ccc2c(c1)OCCO2]

¹H NMR (400 MHz, CDCl₃) δ 1.77 (br, 4H), 2.10-2.15 (m, 2H), 2.24-2.27 (m, 2H), 2.64-2.67 (m, 4H), 2.79-2.83 (m, 2H), 3.02 (t, 2H), 4.18 (s, 4H), 4.26 (br, 1H), 4.92 (d, 1H), 6.12 (br, 1H), 6.75-6.81 (m, 2H), 6.86 (s, 1H), 7.37 (t, 1H), 7.45 (t, 1H), 7.85 (d, 1H), 7.92 (d, 1H); MS for $C_{26}H_{31}N_3O_4S$: [M–H]⁻ 482.

Example 1E51

Preparation of Compound 102: N-((1R,2R)-1-(2,3-dihydrobenzo[β][1,4]dioxin-6-yl)-1-hydroxy-3-(pyrrolidin-1-yl)propan-2-yl)-6-(2,3-dihydrobenzo[β][1,4]dioxine-6-sulfonamido)hexanamide Compound 102 was prepared in a similar manner as described above, following Scheme 1.

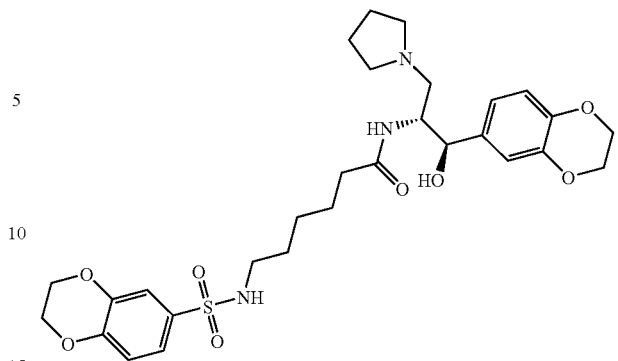

¹H NMR (400 MHz, CDCl₃) δ 1.15-1.20 (m, 2H), 1.38-1.50 (m, 4H), 1.77 (br, 4H), 2.08 (q, 2H), 2.63-2.66 (m, 4H), 2.79 (d, 2H), 2.87 (t, 2H), 4.2 (m, 9H), 4.91 (br, 1H), 5.93 (br, 1H), 6.77 (q, 2H), 6.84 (s, 1H), 6.93 (d, 1H), 7.31 (d, 1H), 7.37 (s, 1H); MS for $C_{29}H_{39}N_3O_8S$: [M–H]⁻ 590.

Example 1E52

Preparation of Compound 104: N-(5-((1R,2R)-1-(2,3-dihydrobenzo[β][1,4]dioxin-6-yl)-1-hydroxy-3-(pyrrolidin-1-yl)propan-2-ylamino)-5-oxopentyl)benzamide Compound 104 was prepared in a similar manner as described above, following Scheme 1.

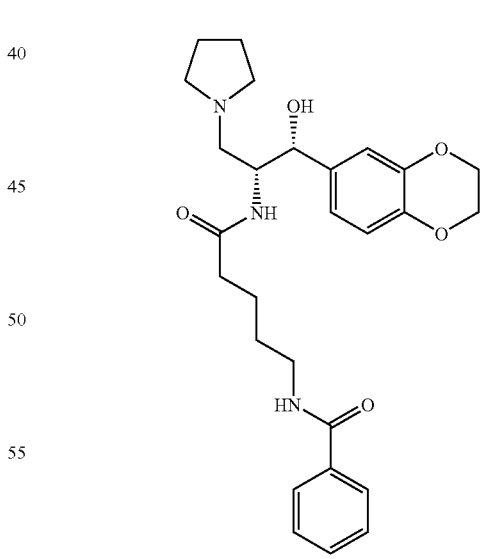

¹H NMR (400 MHz, CDCl₃) δ 1.47-1.52 (m, 2H), 1.59-1.69 (m, 2H), 1.77 (br, 4H), 2.15-2.21 (m, 2H), 2.62-2.65 (m, 4H), 2.81 (br, 2H), 3.30-3.42 (m, 2H), 4.19-4.23 (m, 5H), 4.94 (br, 1H), 5.98 (br, 1H), 6.76 (br, 1H), 6.78-6.86 (m, 3H), 7.40-7.50 (m, 3H), 7.80 (d, 2H); MS for $C_{27}H_{35}N_3O_5$: [M–H]⁻ 482.

Example 1E53

Preparation of Compound 281: N1-((1R,2R)-1-(2,3-dihydrobenzo[β][1,4]dioxin-6-yl)-1-hydroxy-3-(pyrrolidin-1-yl)propan-2-yl)-N5-(thiazol-2-yl)glutaramide Compound 281 was prepared in a similar manner as described above, following Scheme 1.

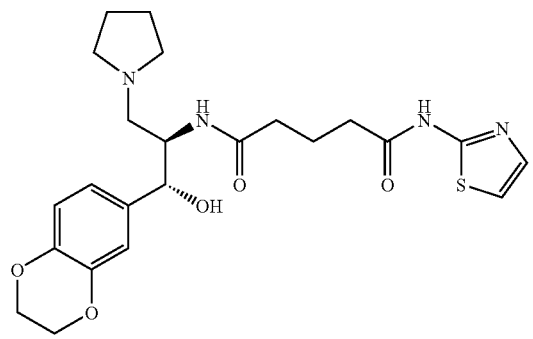 [SMILES: O=C(CCCC(=O)N[C@H](CN1CCCC1)[C@H](O)c1ccc2c(c1)OCCO2)Nc1nccs1]

$^1$H NMR (400 MHz, CDCl$_3$) δ 1.74 (br, 4H), 1.97-2.03 (m, 2H), 2.20-2.26 (m, 2H), 2.40-2.45 (m, 2H), 2.64-2.68 (m, 5H), 2.88 (m 1H), 4.20 (s, 4H), 4.26-4.29 (m, 1H), 4.83 (d, 1H), 6.12 (br, 1H), 6.74-6.79 (m, 2H), 6.85 (s, 1H), 6.95 (d, 1H), 7.41 (d, 1H); MS for C$_{23}$H$_{30}$N$_4$O$_5$S: [M−H]$^−$ 475.

Example 1E54

Preparation of Compound 282: N-((1R,2R)-1-(2,3-dihydrobenzo[β][1,4]dioxin-6-yl)-1-hydroxy-3-(pyrrolidin-1-yl)propan-2-yl)-5-(3,4-dimethoxyphenyl)-5-oxopentanamide Compound 282 was prepared in a similar manner as described above, following Scheme 1.

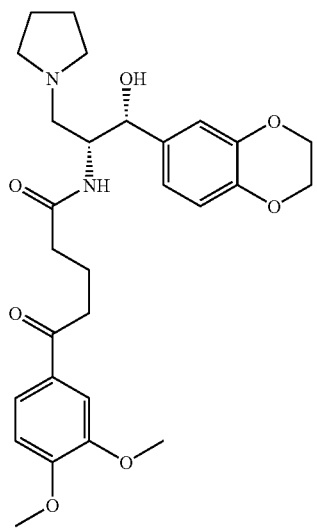 [SMILES: COc1ccc(C(=O)CCCC(=O)N[C@H](CN2CCCC2)[C@H](O)c2ccc3c(c2)OCCO3)cc1OC]

$^1$H NMR (400 MHz, CDCl$_3$) δ 1.76 (br, 4H), 1.92-2.00 (m, 2H), 2.21-2.26 (m, 2H), 2.60-2.65 (m, 4H), 2.70-2.95 (m, 4H), 3.93 (d, 6H), 4.17-4.23 (m, 5H), 4.90 (d, 1H), 5.96 (br, 1H), 6.75-6.79 (m, 2H), 6.85 (s, 1H), 6.87 (d, 1H), 7.50 (s, 1H), 7.55 (d, 1H); MS for C$_{28}$H$_{36}$N$_2$O$_7$: [M−H]$^−$ 513.

Example 1E55

Preparation of Compound 283: N-((1R,2R)-1-(2,3-dihydrobenzo[b][1,4]dioxin-6-yl)-1-hydroxy-3-(pyrrolidin-1-yl)propan-2-yl)-5-oxo-5-p-tolylpentanamide Compound 283 was prepared in a similar manner as described above, following Scheme 1.

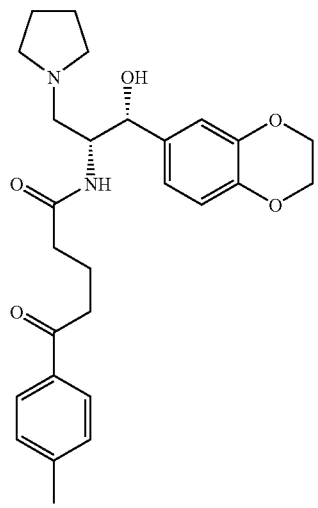 [SMILES: Cc1ccc(C(=O)CCCC(=O)N[C@H](CN2CCCC2)[C@H](O)c2ccc3c(c2)OCCO3)cc1]

$^1$H NMR (400 MHz, CDCl$_3$) δ 1.77 (br, 4H), 1.96-2.02 (m, 2H), 2.21-2.26 (m, 2H), 2.40 (s, 3H), 2.63-2.80 (m, 4H), 2.82-2.95 (m, 4H), 4.18-4.23 (m, 5H), 4.91 (d, 1H), 5.94 (br, 1H), 6.74-6.77 (m, 2H), 6.85 (s, 1H), 7.26 (d, 2H), 7.81 (d, 2H); MS for C$_{27}$H$_{34}$N$_2$O$_5$: [M−H]$^−$ 467.

Example 1E56

Preparation of Compound 113: N-((1R,2R)-1-(2,3-dihydrobenzo[β][1,4]dioxin-6-yl)-1-hydroxy-3-(pyrrolidin-1-yl)propan-2-yl)-5-oxo-5-phenylpentanamide Compound 113 was prepared in a similar manner as described above, following Scheme 1.

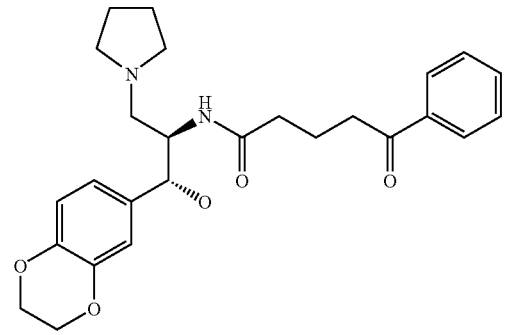 [SMILES: O=C(CCCC(=O)c1ccccc1)N[C@H](CN1CCCC1)[C@H](O)c1ccc2c(c1)OCCO2]

$^1$H NMR (400 MHz, CDCl$_3$) δ 1.76 (br, 4H), 1.95-2.01 (m, 2H), 2.22-2.25 (m, 2H), 2.62-2.63 (m, 4H), 2.78-2.95 (m,

4H), 4.17-4.22 (m, 5H), 4.91 (sd, 1H), 5.99 (br, 1H), 6.77 (st, 2H), 6.85 (s, 1H), 7.44-7.58 (m, 3H), 7.92 (d, 2H); MS for $C_{26}H_{32}N_2O_5$: [M–H]⁻ 453.

Example 1E57

Preparation of Compound 284: N-((1R,2R)-1-(2,3-dihydrobenzo[β][1,4]dioxin-6-yl)-1-hydroxy-3-(pyrrolidin-1-yl)propan-2-yl)-5-(4-isopropoxyphenyl)-5-oxopentanamide Compound 284 was prepared in a similar manner as described above, following Scheme 1.

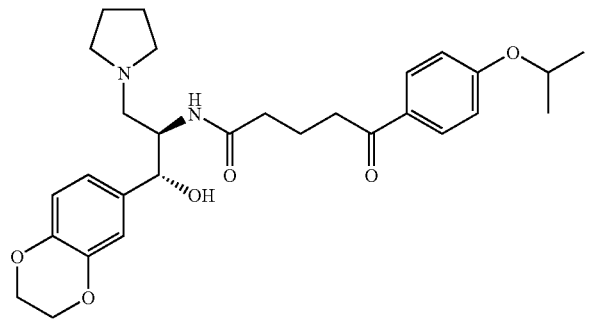 [SMILES: CC(C)Oc1ccc(C(=O)CCCC(=O)N[C@H](CN2CCCC2)[C@H](O)c2ccc3c(c2)OCCO3)cc1]

¹H NMR (400 MHz, CDCl₃) δ 1.36 (d, 6H), 1.75 (br, 4H), 1.90-2.02 (m, 2H), 2.20-2.25 (m, 2H), 2.60-2.66 (m, 4H), 2.70-2.86 (m, 4H), 4.17 (s, 4H), 4.22 (br, 1H), 4.62-4.65 (m, 1H), 4.89 (sd, 1H), 6.07 (d, 1H), 6.77 (s, 2H), 6.85 (s, 1H), 6.87 (d, 2H), 7.86 (d, 2H); MS for $C_{29}H_{38}N_2O_6$: [M–H]⁻ 511.

Example 1E58

Preparation of Compound 140: N-((1R,2R)-1-(2,3-dihydrobenzo[β][1,4]dioxin-6-yl)-1-hydroxy-3-(pyrrolidin-1-yl)propan-2-yl)-6-(4-methoxy-3,5-dimethylphenyl)-6-oxohexanamide Compound 140 was prepared in a similar manner as described above, following Scheme 1.

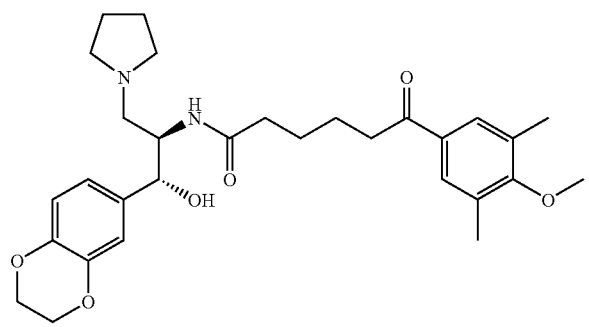 [SMILES: COc1c(C)cc(C(=O)CCCCC(=O)N[C@H](CN2CCCC2)[C@H](O)c2ccc3c(c2)OCCO3)cc1C]

¹H NMR (400 MHz, CDCl₃) δ 1.61-1.63 (m, 4H), 1.77 (br, 4H), 2.16 (t, 2H), 2.32 (s, 6H), 2.61-2.67 (m, 4H), 2.74-2.89 (m, 2H), 2.91 (t, 2H), 3.75 (s, 3H), 4.21 (br, 5H), 4.90 (sd, 1H), 5.93 (br, 1H), 6.75-6.82 (m, 2H), 6.85 (sd, 1H), 7.61 (s, 2H); MS for $C_{30}H_{40}N_2O_6$: [M–H]⁻ 525.

Example 1E59

Preparation of Compound 141: N-((1R,2R)-1-(2,3-dihydrobenzo[β][1,4]dioxin-6-yl)-1-hydroxy-3-(pyrrolidin-1-yl)propan-2-yl)-6-(4-methoxyphenyl)-6-oxohexanamide Compound 141 was prepared in a similar manner as described above, following Scheme 1.

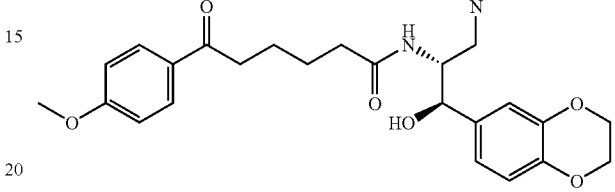

¹H NMR (400 MHz, CDCl₃) δ 1.62-1.64 (m, 4H), 1.76 (br, 4H), 2.17 (t, 2H), 2.61-2.65 (m, 4H), 2.72-2.79 (m, 2H), 2.89 (t, 2H), 3.86 (s, 3H), 4.20 (br, 5H), 4.89 (d, 1H), 6.01 (br, 1H), 6.77 (q, 2H), 6.85 (s, 1H), 6.91 (d, 2H), 7.90 (d, 2H); MS for $C_{28}H_{36}N_2O_6$: [M–H]⁻ 497.

Example 1E60

Preparation of Compound 155: 6-(4-tert-butylphenyl)-N-((1R,2R)-1-(2,3-dihydrobenzo[β][1,4]dioxin-6-yl)-1-hydroxy-3-(pyrrolidin-1-yl)propan-2-yl)-6-oxohexanamide Compound 155 was prepared in a similar manner as described above, following Scheme 1.

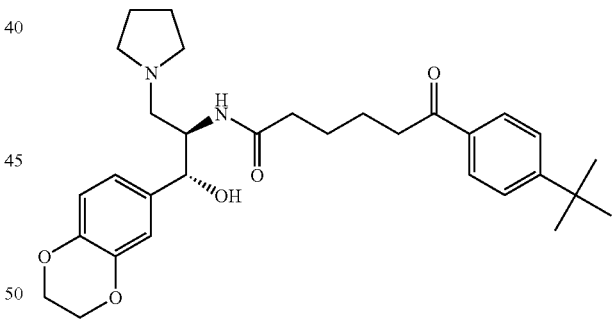

¹H NMR (400 MHz, CDCl₃) δ 1.34 (s, 9H), 1.63-1.65 (m, 4H), 1.77 (br, 4H), 2.17 (t, 2H), 2.64-2.66 (br, 4H), 2.75 (dd, 1H), 2.2.81 (dd, 1H), 2.91 (t, 2H), 4.20 (br, 5H), 4.90 (d, 1H), 6.02 (br, 1H), 6.77-6.82 (q, 2H), 6.85 (d, 1H), 7.46 (d, 2H), 7.86 (d, 2H); MS for $C_{31}H_{42}N_2O_5$: [M–H]⁻ 523.

Example 1E61

Preparation of Compound 156: N-((1R,2R)-1-(2,3-dihydrobenzo[β][1,4]dioxin-6-yl)-1-hydroxy-3-(pyrrolidin-1-yl)propan-2-yl)-7-(4-methoxyphenyl)-7-oxoheptanamide Compound 156 was prepared in a similar manner as described above, following Scheme 1.

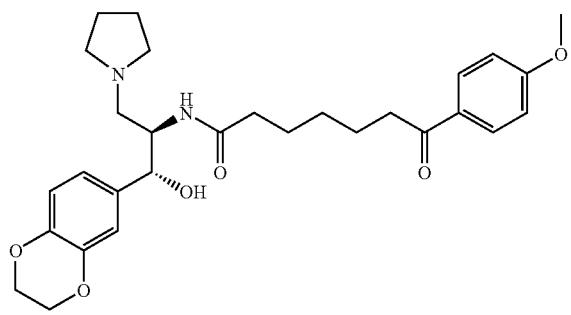 [SMILES: COc1ccc(C(=O)CCCCCC(=O)N[C@H](CN2CCCC2)[C@H](O)c2ccc3c(c2)OCCO3)cc1]

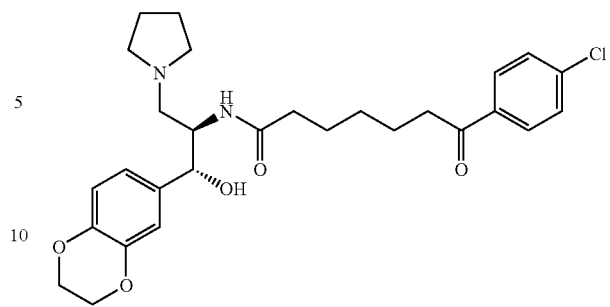

¹H NMR (400 MHz, CDCl₃) δ 1.25-1.30 (m, 2H), 1.55-1.70 (m, 4H), 1.77 (br, 4H), 2.13 (t, 2H), 2.61-2.66 (m, 4H), 2.74-2.82 (m, 2H), 2.88 (t, 2H), 3.86 (s, 3H), 4.20 (br, 5H), 4.90 (d, 1H), 5.93 (br, 1H), 6.78 (q, 2H), 6.85 (s, 1H), 6.91 (d, 2H), 7.92 (d, 2H); MS for $C_{29}H_{38}N_2O_6$: [M–H]⁻ 511.

¹H NMR (400 MHz, CDCl₃) δ 1.26-1.37 (m, 2H), 1.57 (m, 2H), 1.68 (m, 2H), 1.77 (br, 4H), 2.13 (t, 2H), 2.62-2.65 (m, 4H), 2.76-2.82 (m, 2H), 2.90 (t, 2H), 4.20 (br, 5H), 4.90 (d, 1H), 5.93 (d, 1H), 6.78 (q, 2H), 6.85 (s, 1H), 7.42 (d, 2H), 7.87 (d, 2H); MS for $C_{28}H_{35}ClN_2O_5$: [M–H]⁻ 515.

Example 1E62

Preparation of Compound 144: N-((1R,2R)-1-(2,3-dihydrobenzo[β][1,4]dioxin-6-yl)-1-hydroxy-3-(pyrrolidin-1-yl)propan-2-yl)-8-(4-methoxyphenyl)-8-oxooctanamide Compound 144 was prepared in a similar manner as described above, following Scheme 1.

Example 1E64

Preparation of Compound 160: 7-(4-tert-butylphenyl)-N-((1R,2R)-1-(2,3-dihydrobenzo[β][1,4]dioxin-6-yl)-1-hydroxy-3-(pyrrolidin-1-yl)propan-2-yl)-7-oxoheptanamide Compound 160 was prepared in a similar manner as described above, following Scheme 1.

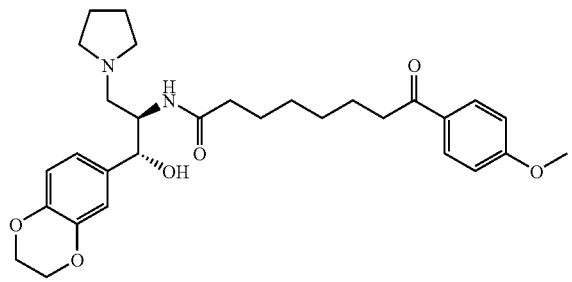 [SMILES: COc1ccc(C(=O)CCCCCCC(=O)N[C@H](CN2CCCC2)[C@H](O)c2ccc3c(c2)OCCO3)cc1]

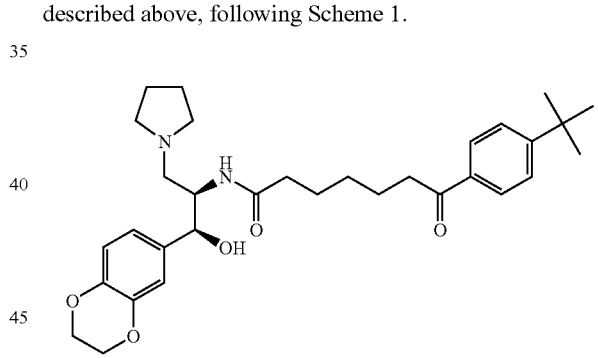

¹H NMR (400 MHz, CDCl₃) δ 1.25-1.33 (m, 4H), 1.54 (m, 2H), 1.68 (t, 2H), 1.78 (br, 4H), 2.11 (br, 2H), 2.65 (br, 4H), 2.76-2.11 (m, 4H), 3.86 (s, 3H), 4.21 (br, 5H), 4.90 (br, 1H), 6.02 (d, 1H), 6.78-6.84 (m, 3H), 6.91 (d, 2H), 7.92 (d, 2H); MS for $C_{30}H_{40}N_2O_6$: [M–H]⁻ 525.

¹H NMR (400 MHz, CDCl₃) δ 1.27-1.34 (m, 11H), 1.56-1.71 (m, 4H), 1.77 (br, 4H), 2.13 (t, 2H), 2.63-2.66 (m, 4H), 2.76-2.819 (m, 2H), 2.91 (t, 2H), 4.20 (br, 5H), 4.90 (sd, 1H), 5.90 (d, 1H), 6.81 (q, 2H), 6.85 (s, 1H), 7.46 (d, 2H), 7.88 (d, 2H); MS for $C_{32}H_{44}N_2O_5$: [M–H]⁻ 537.

Example 1E63

Preparation of Compound 159: 7-(4-chlorophenyl)-N-((1R,2R)-1-(2,3-dihydrobenzo[β][1,4]dioxin-6-yl)-1-hydroxy-3-(pyrrolidin-1-yl)propan-2-yl)-7-oxoheptanamide Compound 159 was prepared in a similar manner as described above, following Scheme 1.

Example 1E65

Preparation of Compound 168: N-((1R,2R)-1-(2,3-dihydrobenzo[b][1,4]dioxin-6-yl)-1-hydroxy-3-(pyrrolidin-1-yl)propan-2-yl)-7-(4-methoxyphenyl)-7-oxoheptanamide(2S,3S)-2,3-dihydroxysuccinate Compound 168 was prepared in a similar manner as described above, following Scheme 1.

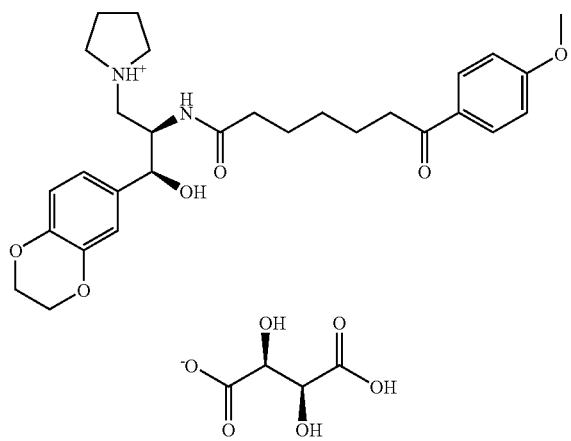

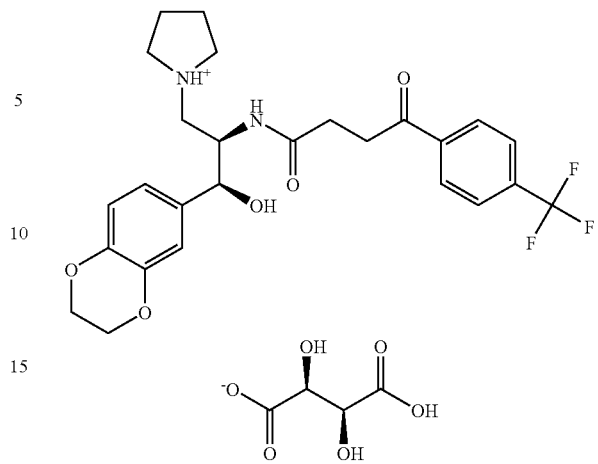

¹H NMR (400 MHz, CD₃OD) δ 1.15-1.19 (m, 2H), 1.40-1.47 (m, 2H), 1.60 (m, 2H), 2.02 (br, 4H), 2.09-2.21 (m, 2H), 2.90 (t, 2H), 3.35-3.49 (m, 5H), 3.83 (s, 3H), 4.12 (br, 4H), 4.38 (s, 2H), 4.43 (m, 1H), 4.74 (sd, 1H), 6.71 (d, 1H), 6.79 (dq, 1H), 6.86 (sd, 1H), 6.96 (d, 2H), 7.92 (d, 2H); MS for $C_{29}H_{38}N_2O_6 \cdot C_4H_6O_6$: [M–H]⁻ 661.

Example 1E66

Preparation of Compound 162: N-((1R,2R)-1-(2,3-dihydrobenzo[β][1,4]dioxin-6-yl)-1-hydroxy-3-(pyrrolidin-1-yl)propan-2-yl)-4-(4-isopropoxyphenyl)-4-oxobutanamide Compound 162 was prepared in a similar manner as described above, following Scheme 1.

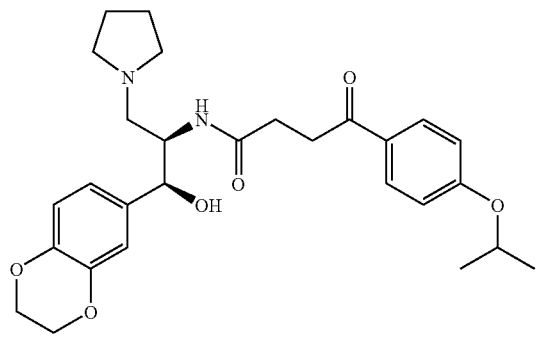 [SMILES: CC(C)Oc1ccc(C(=O)CCC(=O)N[C@H](CN2CCCC2)[C@@H](O)c2ccc3c(c2)OCCO3)cc1]

¹H NMR (400 MHz, CDCl₃) δ 1.35 (d, 6H), 1.77 (br, 4H), 2.52-2.56 (m, 2H), 2.64-2.83 (m, 6H), 3.09-3.36 (m, 2H), 4.22 (br, 5H), 4.63-4.66 (m, 1H), 4.89 (sd, 1H), 6.13 (d, 1H), 6.78 (s, 2H), 6.88 (t, 3H), 7.90 (d, 2H); MS for $C_{28}H_{36}N_2O_6$: [M–H]⁻ 497.

Example 1E67

Preparation of Compound 176: N-((1R,2R)-1-(2,3-dihydrobenzo[β][1,4]dioxin-6-yl)-1-hydroxy-3-(pyrrolidin-1-yl)propan-2-yl)-4-oxo-4-(4-(trifluoromethyl)phenyl)butanamide(2S,3S)-2,3-dihydroxysuccinate Compound 176 was prepared in a similar manner as described above, following Scheme 1.

¹H NMR (400 MHz, CD₃OD) δ 2.08 (br, 4H), 2.54-2.72 (m, 2H), 3.24-3.48 (m, 6H), 4.19 (s, 4H), 4.29 (m, 4H), 4.74 (sd, 1H), 6.76 (d, 1H), 6.86 (d, 1H), 6.92 (s, 1H), 7.81 (d, 2H), 8.13 (d, 2H); MS for $C_{26}H_{29}F_3N_2O_5 \cdot C_4H_6O_6$: [M–H]⁻ 657.

Example 1E68

Preparation of Compound 65 (Genz-528152-1): 2-(3'-chlorobiphenyl-4-yl)-N-((1R,2R)-1-(2,3-dihydrobenzo[β][1,4]dioxin-6-yl)-1-hydroxy-3-(pyrrolidin-1-yl)propan-2-yl)acetamide Compound 65 was prepared in a similar manner as described above, following Scheme 1.

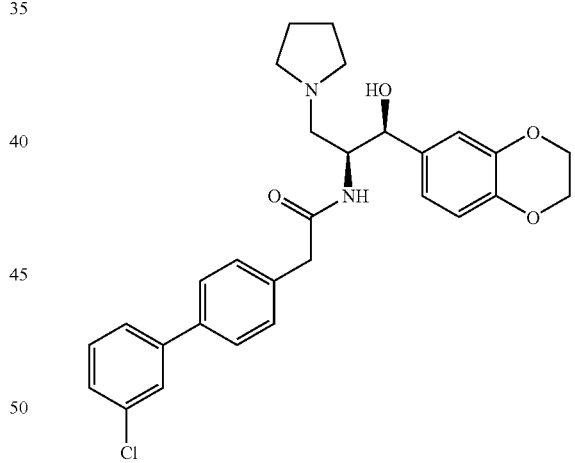

¹H NMR (400 MHz, CDCl₃) δ 1.70 (br, 4H), 2.54 (br, 4H), 2.72-2.81 (m, 2H), 3.53 (s, 2H), 4.12-4.23 (m, 5H), 4.85 (d, 1H), 5.82 (d, 1H), 6.58 (dd, 1H), 6.70 (sd, 1H), 6.73 (d, 1H), 7.19 (d, 1H), 7.32-7.34 (m, 1H), 7.38 (t, 1H), 7.46-7.49 (m, 1H), 7.52 (d, 2H), 7.59 (d, 1H); $C_{29}H_{31}ClN_2O_4$: [M–H]⁻ 507.

Example 1E69

Preparation of Compound 262: N-[2-Hydroxy-2-(4-methoxy-phenyl)-1-pyrrolidin-1-ylmethyl-ethyl]-3-(4-methoxy-phenoxy)-propionamide Compound 262 was prepared in a similar manner as described above, following Scheme 2.

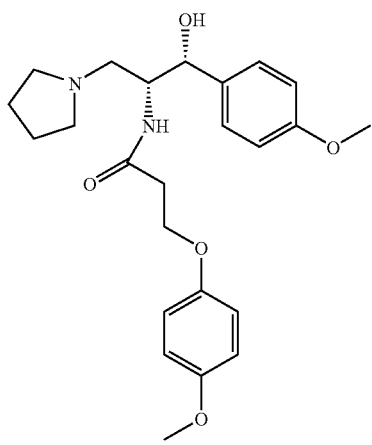 [SMILES: COc1ccc(OCCC(=O)N[C@H](CN2CCCC2)[C@H](O)c2ccc(OC)cc2)cc1]

¹H NMR (CDCl₃ 400 mHz, ppm); 1.75 (m, 4H), 2.55 (m, 2H), 2.65 (m, 4H), 2.85 (m, 2H), 3.8 (s, 6H), 4.1 (m, 2H), 4.25 (m, 1H), 5.0 (d, 1H), 6.5 (br. d, 1H), 6.8 (m, 4H), 7.25 (m, 4H). M/Z for $C_{24}H_{32}N_2O_5$ [M–H]⁺ 429

Example 1E70

Preparation of Compound 270: 5-(4-Isopropoxy-phenyl)-5-oxo-pentanoic acid [2-hydroxy-2-(4-methoxy-phenyl)-1-pyrrolidin-1-ylmethyl-ethyl]amide Compound 270 was prepared in a similar manner as described above, following Scheme 2.

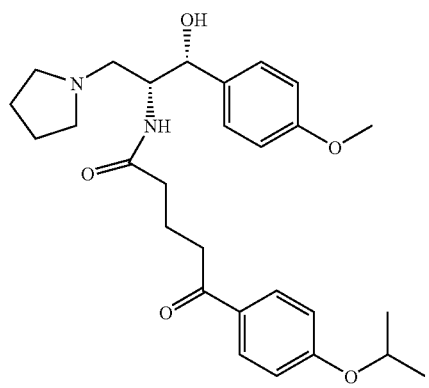 [SMILES: COc1ccc([C@@H](O)[C@@H](CN2CCCC2)NC(=O)CCCC(=O)c2ccc(OC(C)C)cc2)cc1]

¹H NMR (CDCl₃ 400 mHz, ppm); 1.4 (d, 6H), 1.8 (m, 4H), 2.0 (m, 2H), 2.2 (m, 2H), 2.6 (m, 4H), 2.8 (m, 4H), 3.75 (s, 3H), 4.25 (m, 1H), 4.65 (m, 1H), 5.0 (d, 1H), 5.95 (br. d, 1H), 6.85 (m, 4H), 7.25 (m, 2H), 7.9 (m, 2H). M/Z for $C_{24}H_{32}N_2O_5$ [M–H]⁺ 483.3

Example 1E71

Preparation of Compound 285: 7-(4-Methoxy-phenyl)-7-oxo-heptanoic acid [2-hydroxy-2-(4-methoxy-phenyl)-1-pyrrolidin-1-ylmethyl-ethyl]-amide Compound 285 was prepared in a similar manner as described above, following Scheme 2.

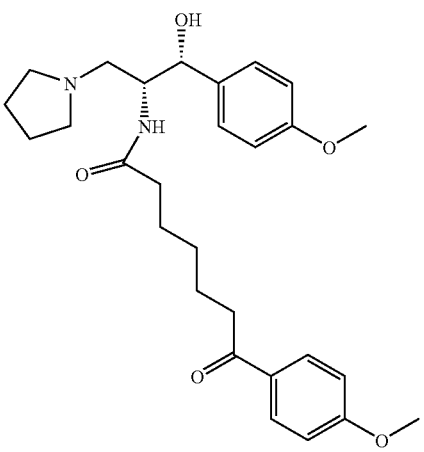 [SMILES: COc1ccc(C(=O)CCCCCC(=O)N[C@H](CN2CCCC2)[C@H](O)c2ccc(OC)cc2)cc1]

¹H NMR (CDCl₃ 400 mHz, ppm); 1.25 (m, 2H), 1.6 (m, 4H), 1.8 (m, 4H), 2.15 (m, 2H), 2.65 (m, 4H), 2.85 (m, 4H), 3.75 (s, 3H), 3.9 (s, 3H), 4.2 (m, 1H), 5.0 (d, 1H), 5.9 (br. d, 1H), 6.85 (d, 2H), 6.95 (d, 2H), 7.2 (d, 2H), 7.95 (d, 2H). M/Z for $C_{24}H_{32}N_2O_5$ [M–H]⁺ 483.3

Example 1E72

Preparation of Compound 262: N-[2-Hydroxy-2-(4-methoxy-phenyl)-1-pyrrolidin-1-ylmethyl-ethyl]-3-(4-methoxy-phenoxy)-propionamide Compound 262 was prepared in a similar manner as described above, following Scheme 2.

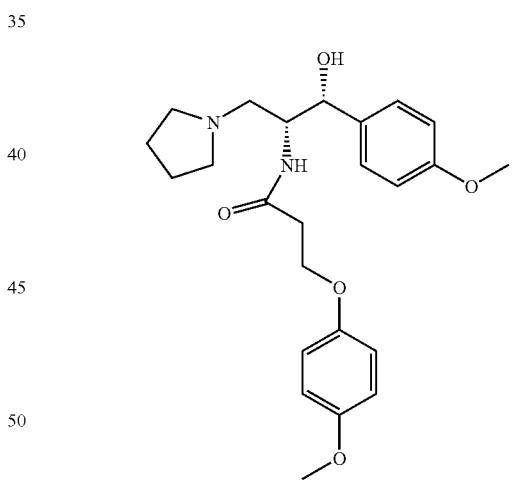

¹H NMR (CDCl₃ 400 mHz, ppm); 1.75 (m, 4H), 2.55 (m, 2H), 2.65 (m, 4H), 2.85 (m, 2H), 3.8 (s, 6H), 4.1 (m, 2H), 4.25 (m, 1H), 5.0 (d, 1H), 6.5 (br. d, 1H), 6.8 (m, 4H), 7.25 (m, 4H). M/Z for $C_{24}H_{32}N_2O_5$ [M–H]⁺ 429

Example 1E73

Preparation of Compound 270: 5-(4-Isopropoxy-phenyl)-5-oxo-pentanoic acid [2-hydroxy-2-(4-methoxy-phenyl)-1-pyrrolidin-1-ylmethyl-ethyl]amide Compound 270 was prepared in a similar manner as described above, following Scheme 2.

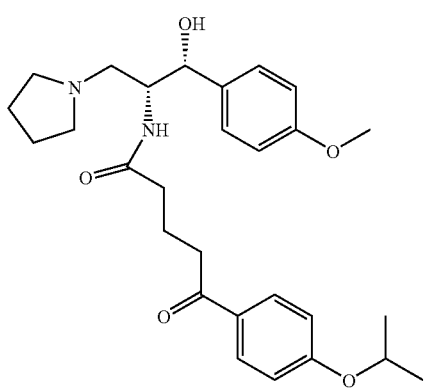 [SMILES: COc1ccc([C@@H](O)[C@@H](CN2CCCC2)NC(=O)CCCC(=O)c2ccc(OC(C)C)cc2)cc1]

<sup>1</sup>H NMR (CDCl₃ 400 mHz, ppm); 1.4 (d, 6H), 1.8 (m, 4H), 2.0 (m, 2H), 2.2 (m, 2H), 2.6 (m, 4H), 2.8 (m, 4H), 3.75 (s, 3H), 4.25 (m, 1H), 4.65 (m, 1H), 5.0 (d, 1H), 5.95 (br. d, 1H), 6.85 (m, 4H), 7.25 (m, 2H), 7.9 (m, 2H). M/Z for $C_{24}H_{32}N_2O_5$ [M–H]⁺ 483.3

Example 1E74

Preparation of Compound 305

Compound 305 characterized by the following structural formula was prepared in a similar manner as described above, following Scheme 2.

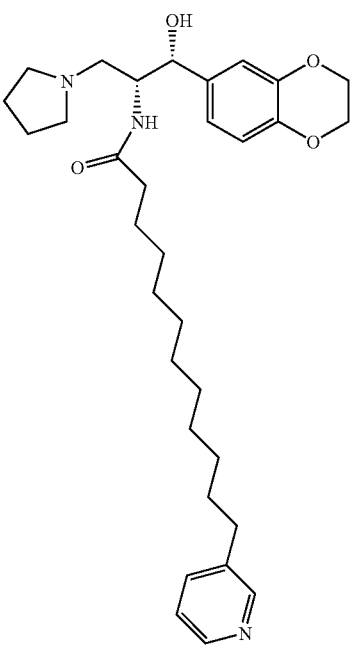 [SMILES: O=C(CCCCCCCCCCCc1cccnc1)N[C@H](CN1CCCC1)[C@H](O)c1ccc2c(c1)OCCO2]

<sup>1</sup>H NMR (CDCl₃ 400 mHz, ppm); 1.25 (m, 14H), 1.6 (m, 4H), 1.8 (m, 4H), 2.1 (t, 2H), 2.6 (t, 2H), 2.8 (m, 6H), 4.2 (m, 5H), 4.9 (d, 1H), 6.0 (br d, 1H), 6.8 (m, 3H), 7.2 (m, 1H), 7.5 (m, 1H), 8.4 (m, 2H). M/Z for $C_{24}H_{32}N_2O_5$ [M–H]⁺ 538

Example 1E75

Preparation of Compound 320: Octanoic acid [2-hydroxy-2(4-methoxy-phenyl)-1-Pyrrolidin1-ylmethyl-ethyl]-amide Compound 320 characterized by the following structural formula was prepared in a similar manner as described above, following Scheme 2.

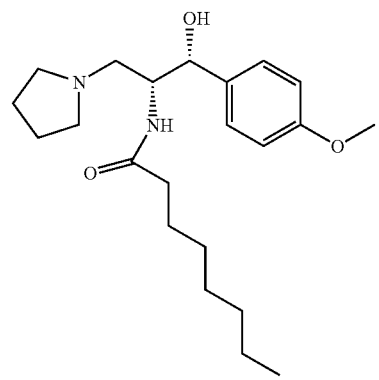 [SMILES: CCCCCCCC(=O)N[C@H](CN1CCCC1)[C@H](O)c1ccc(OC)cc1]

<sup>1</sup>H NMR (CDCl₃ 400 mHz, ppm); 0.9 (t, 3H), 1.2 (m, 8H), 1.5 (m, 2H), 1.8 (m, 4H), 2.1 (t, 2H), 2.65 (m, 4H), 2.8 (d, 2H), 3.8 (s, 3H), 4.2 (m, 1H), 4.95 (d, 1H), 5.9 (br d, 1H), 6.9 (2s, 2H), 7.25 (m, 2H). M/Z for $C_{22}H_{36}N_2O_3$ [M–H]⁺ 377.4

Example 1E76

Preparation of Cyclic Amide Analogs

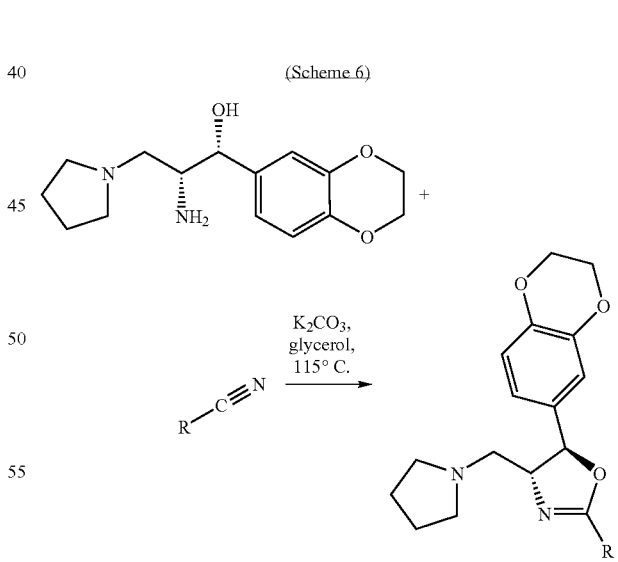

(Scheme 6)

Cyclic amide analogs were prepared according to Scheme 6. 2-Amino-1-(2,3-dihydro-benzo[1,4]dioxin-6-yl)-3-pyrrolidin-1-yl-propan-1-ol was prepared according to the preparation of intermediate 4 of U.S. Pat. No. 6,855,830 B2. This amine was coupled with various nitriles in potassium carbonate and glycerol, under an atmosphere of nitrogen, for example, at 115° C. for 18 hours. Compound 323 characterized by the following structural formula was prepared by following Scheme 6. Compound 323 was purified by column chromatography using a mixture of methanol and methylene chloride.

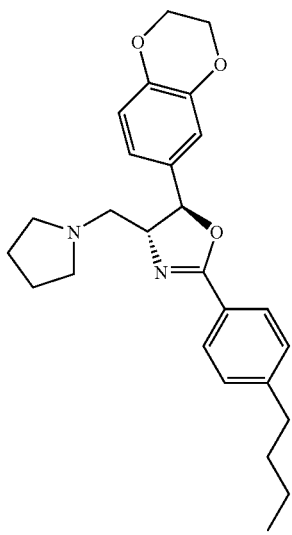 [SMILES: CCCCc1ccc(C2=N[C@H](CN3CCCC3)[C@@H](c3ccc4c(c3)OCCO4)O2)cc1]

$^1$H NMR (CDCl$_3$ 400 mHz, ppm); 0.95 (t, 3H), 1.35 (m, 2H), 1.6 (m, 2H), 1.8 (m, 4H), 2.7 (m, 6H), 2.8 (m, 2H), 4.2 (m, 5H), 5.4 (d, 1H), 6.85 (m, 3H), 7.2 (m, 2H), 7.9 (d, 2H). M/Z for C$_{24}$H$_{32}$N$_2$O$_5$ [M−H]$^+$ 421.54

Example 2

Synthesis of Ceramide Derivatives: Preparation of Carbamate Analogs

Example 2A1

Preparation of (R)-benzyl 4-formyl-2,2-dimethyloxazolidine-3-carboxylate

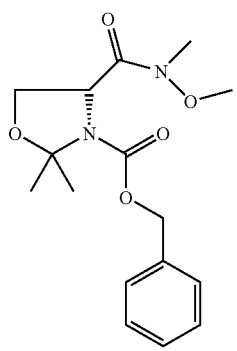

Steps 1-2: preparation of (R)-benzyl 4-(methoxy(methyl) carbamoyl)-2,2-dimethyloxazolidine-3-carboxylate: N,O-dimethylhydroxylamine hydrochloride (45 g, 0.46 mmol, 1.5 eq) and N-methyl morpholine (84 mL, 0.765 mol, 2.5 eq.) were added slowly to a cold (−15° C.) suspension of d-CBz serine (73.0 g, 0.305 mol) in CH$_2$Cl$_2$ (560 mL) keeping the temperature below −5° C. The mixture was cooled back to ~−15° C. and EDCI (62 g, 0.323 mol, 1.05 eq) was added. The mixture was stirred for 5 hours keeping the temperature below 5° C. The solvent was removed by rotary evaporation and the mixture was partitioned between HCl (1 M, 300 mL) and EtOAc (500 mL). The organic layer was separated and washed with HCl (1 M, 2×100 mL) and then sat. NaHCO$_3$ (2×150 mL). The mixture was dried over MgSO$_4$, filtered and then the solvent was removed by rotary evaporation. (R)-benzyl 3-hydroxy-1-(methoxy(methyl)amino)-1-oxopropan-2-ylcarbamate was re-dissolved in a mixture of acetone (375 mL) and 2,2-dimethoxy propane (375 mL) and boron trifluoride ethereate (3 mL) was added. The mixture was stirred at room temperature for 5 hours and then triethyl amine (3 mL) was added. The solvent was removed to dryness and (R)-benzyl 4-(methoxy(methyl)carbamoyl)-2,2-dimethyloxazolidine-3-carboxylate was obtained as a white solid (73.0 g, 74% yield from both steps) after purification by column chromatography using a mixture of hexane/EtOAc/acetone.

$^1$H NMR (CDCl$_3$, 400 mHz, ppm); 1.5 (s, 2H), 1.6 (s, 3H), 1.7 (s, 2H), 1.75 (s, 3H), 3.14 (s, 3H), 3.24 (2H), 3.4 (3H), 3.76 (s, 2H), 4.0 (m, 1.7H), 4.16 (m, 1H), 4.2 (m, 1.7), 4.78 (m, 1H), 4.88 (m, 0.6H), 5.06 (q, 2H), 5.18 (q, 1H), 7.4 (m, 8H).

Step 3: Preparation of (R)-benzyl 4-formyl-2,2-dimethyloxazolidine-3-carboxylate

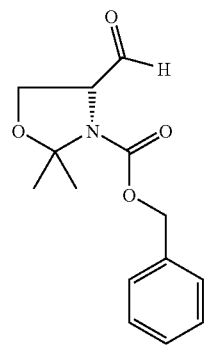

A solution of LiALH$_4$ (1 M, 20 mL, 20 mmol) was added dropwise to a cold (−15° C.) solution of (R)-benzyl 4-(methoxy(methyl)carbamoyl)-2,2-dimethyloxazolidine-3-carboxylate (12.2 g, 37.9 mmol) in THF (75 mL). The mixture was stirred for 30 min keeping the temperature below 0° C. A saturated solution of KHSO$_4$ (100 mL) was added slowly to the mixture and it was warmed to room temperature. The mixture was filtered and the solvent was removed to dryness. (R)-benzyl 4-formyl-2,2-dimethyloxazolidine-3-carboxylate was obtained as a clear oil (9.161 g, 92% yield) after purification by column chromatography (SiO$_2$, using a mixture of hexane/EtOAc). $^1$H NMR (CDCl$_3$, 400 mHz, ppm); 1.7 (m, 6H), 4.15 (m, 2H), 4.4 (m, 1H), 5.15, (s, 1H), 5.2 (m, 1H), 7.3 (m, 5H), 9.6 (m, 1H).

Example 2A2

Preparation of (R)-benzyl 4-((R)-hydroxy(4-methoxyphenyl)methyl)-2,2-dimethyloxazolidine-3-carboxylate

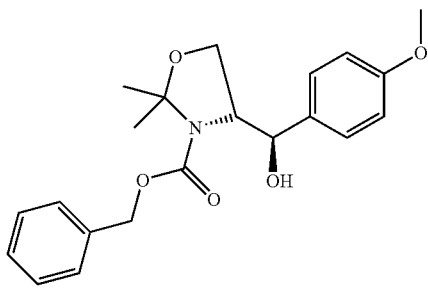

1,2-dibromoethane (0.2 mL) was added slowly to a hot (65° C.) solution of magnesium turnings (0.91 g, 37 mmol) in THF (14 mL), followed by the dropwise addition of a solution of 4-bromo anisole (4 mL, 32 mmol) in THF (14 mL). The mixture was refluxed for 2 hours and then cooled to room temperature. The grignard solution was added dropwise to a suspension of CuI (6.8 g, 36 mmol) in a mixture of $Me_2S$ (20 mL)/THF (100 mL) at −78° C. The mixture was warmed slowly to −45° C. and stirred for 30 min keeping the temperature between −45 to −35° C. The mixture was cooled back to −78° C., and a solution of the Garner's aldehyde[(R)-benzyl 4-formyl-2,2-dimethyloxazolidine-3-carboxylate] (3.20 g, 12.6 mmol) in THF (15 mL) was added dropwise. The mixture was stirred at low temperature overnight (15 h, T max=10° C.). The reaction mixture was quenched with $NH_4Cl$ (sat. 100 mL) and extracted with EtOAc (50 mL). The solvent was removed to dryness and the mixture was purified by column chromatography ($SiO_2$, using a mixture of hexane/EtOAc/acetone) and the product was obtained as a colorless oil (1.697 g, 36% yield).

Example 2A3

Preparation of benzyl(1R,2R)-1,3-dihydroxy-1-(4-methoxyphenyl)propan-2-ylcarbamate

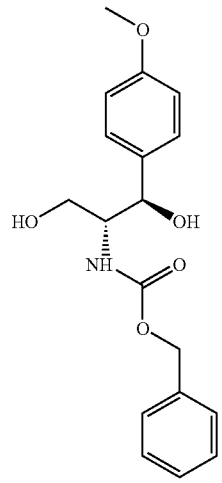 [SMILES: COc1ccc([C@@H](O)[C@@H](CO)NC(=O)OCc2ccccc2)cc1]

A mixture of benzyl 4-(hydroxy-(4-methoxyphenyl)methyl)-2,2-dimethyloxazolidine-3-carboxylate (1.679 g, 4.5 mmol) and amberlyst 15 (1.85 g) in MeOH (20 mL) was stirred at room temperature for 2 days. The mixture was centrifuged and the solid was washed with MeOH (2×40 mL). The solvent was removed to dryness and after purification by column chromatography ($SiO_2$ using a mixture of $CH_2Cl_2$/EtOAc) the product was obtained as a white solid (1.26 g, 84% yield).

Example 2A4

Synthesis of Compound 289: benzyl(1R,2R)-1-hydroxy-1-(4-methoxyphenyl)-3-(pyrrolidin-1-yl)propan-2-ylcarbamate

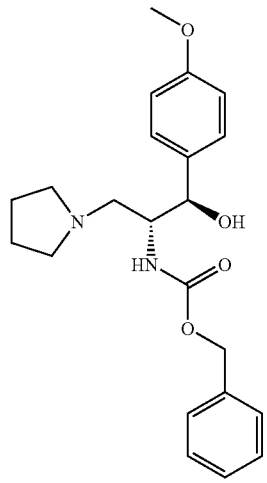 [SMILES: COc1ccc([C@@H](O)[C@@H](CN2CCCC2)NC(=O)OCc2ccccc2)cc1]

Mesityl chloride (0.28 mL, 3.6 mmol) was added slowly to a cold (−10° C.) solution of benzyl(1R,2R)-1,3-dihydroxy-1-(4-methoxyphenyl)propan-2-ylcarbamate (1.07 g, 3.23 mmol) in pyridine (1.5 mL). The mixture was stirred for 30 min and then pyrrolidine (2.7 mL, 33 mmol) was added slowly to the mixture. The mixture was heated to 45° C. for 6 hours and then the solvent was removed to dryness. After purification by column chromatography ($SiO_2$, using a mixture of $CH_2Cl_2$, MeOH, $NH_4OH$), the product was obtained as a clear oil (0.816 g, 66% yield).

Example 3

Synthesis of Ceramide Derivatives: General Procedures for the Synthesis of Urea Analogs (Scheme 5)

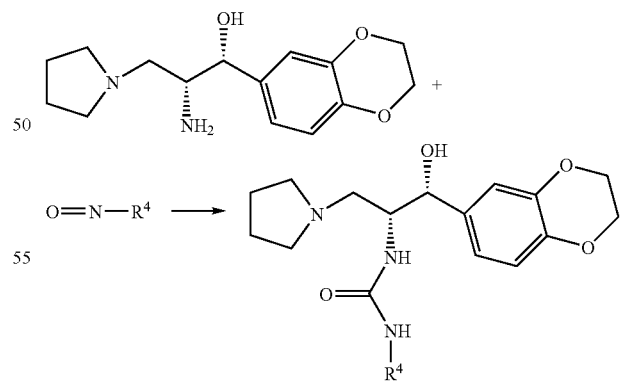

(1R,2R)-2-amino-(2,3-dihydrobenzo[β][1,4[dioxin-6-yl)-3-(pyrrolidin-1-yl)propan-1-ol, prepared according to the preparation of intermediate 4 of U.S. Pat. No. 6,855,830 (the entire teachings of which are incorporated herein by reference), was dissolved in methylene chloride and activated 5 Å molecular sieves were added to the solution, followed by addition of the particular isocyanate ($R^4NO$). Reaction times varied depending on the isocyanate substitution from one to twelve hours. Compounds 6, 7, 10, 17, 40, 41, 42, 43, 68, 69, 70, 71, 80, 81, 82, 133, 257, 261, 286 and 287, shown in Examples 3A1-3A21 below, were prepared following reaction Scheme 5. The compounds were purified by column chromatography.

Example 3A1

Preparation of Compound 6: 1-benzyl-3-((1R,2R)-1-(2,3-dihydrobenzo[β][1,4]dioxin-6-yl)-1-hydroxy-3-(pyrrolidin-1-yl)propan-2-yl)urea

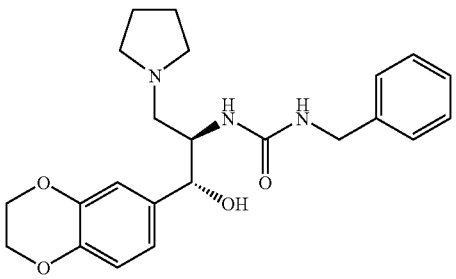 [SMILES: O=C(NCc1ccccc1)N[C@H](CN1CCCC1)[C@H](O)c1ccc2c(c1)OCCO2]

¹H NMR (400 MHz, CDCl₃) δ=1.7 (s, 4H), 2.4-2.6 (m, 5H), 2.6-2.7 (dd, 1H), 4.0 (m, 1H), 4.2 (s, 4H), 4.3 (m, 2H), 4.8 (d, 1H), 4.86 (d, 1H), 5.0 (br, 1H), 6.6-6.9 (m, 3H), 7.2-7.4 (m, 5H); MS for $C_{23}H_{29}N_3O_4$ m/z 412.2 [M+H]

Example 3A2

Preparation of Compound 17: 1-((1R,2R)-1-(2,3-dihydrobenzo[β][1,4]dioxin-6-yl)-1-hydroxy-3-(pyrrolidin-1-yl)propan-2-yl)-3-(4-fluorobenzyl)urea

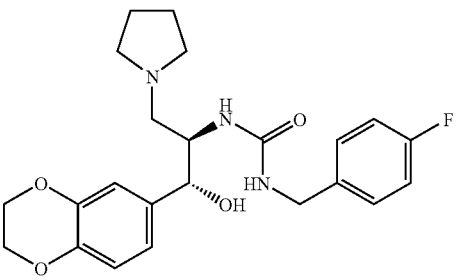 [SMILES: O=C(NCc1ccc(F)cc1)N[C@H](CN1CCCC1)[C@H](O)c1ccc2c(c1)OCCO2]

¹H NMR (400 MHz, CDCl₃) δ=1.6 (s, 4H), 2.4-2.6 (m, 6H), 3.9 (m, 1H), 4.0-4.1 (m, 2H), 4.13 (s, 4H), 4.7 (d, 1H), 5.4 (d, 1H), 6.6-7.1 (m, 7H); MS for $C_{23}H_{28}FN_3O_4$ m/z 430.2 [M+H].

Example 3A3

Preparation of Compound 40: 1-(4-bromobenzyl)-3-((1R,2R)-1-(2,3-dihydrobenzo[β][1,4]dioxin-6-yl)-1-hydroxy-3-(pyrrolidin-1-yl)propan-2-yl)urea

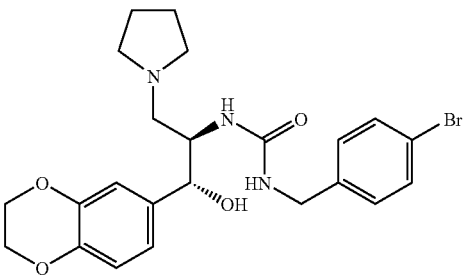 [SMILES: O=C(NCc1ccc(Br)cc1)N[C@H](CN1CCCC1)[C@H](O)c1ccc2c(c1)OCCO2]

¹H NMR (400 MHz, CDCl₃) δ=1.7 (s, 4H), 2.4-2.8 (m, 6H), 4.0 (m, 1H), 4.1-4.2 (m, 2H) 4.2 (s, 4H), 4.8 (d, 1H), 5.3 (d, 1H), 5.6-5.8 (br, 1H), 6.8-7.0 (m, 3H), 7.0 (d, 2H), 7.4 (d, 2H); MS for $C_{23}H_{28}BrN_3O_4$ m/z 490 [M], 491 [M+H], 492 [M+2].

Example 3A4

Preparation of Compound 41: 1-((1R,2R)-1-(2,3-dihydrobezo[β][1,4]dioxin-6-yl)-1-hydroxy-3-(pyrrolidin-1-yl)propan-2-yl)-3-(4-methoxybenzyl)urea

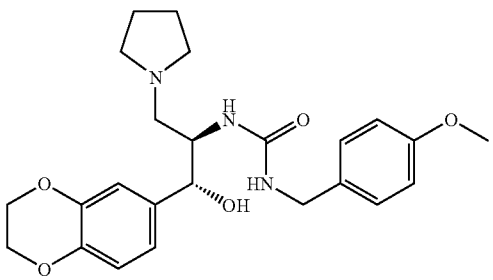 [SMILES: COc1ccc(CNC(=O)N[C@H](CN2CCCC2)[C@H](O)c2ccc3c(c2)OCCO3)cc1]

¹H NMR (400 MHz, CDCl₃) δ=1.6 (s, 4H), 2.4-2.6 (m, 6H), 3.7 (s, 3H), 3.9 (m, 1H), 4.1 (d, 2H), 4.2 (s, 4H), 4.7 (d, 1H), 5.2 (d, 1H), 5.5-5.7 (br, 1H), 6.6-6.8 (m, 5H), 7.1 (d, 2H); MS for $C_{24}H_{31}N_3O_5$ m/z 442.2 [M+H]

Example 3A5

Preparation of Compound 80: 1-((1R,2R)-1-(2,3-dihydrobenzo[β][1,4]dioxin-6-yl)-1-hydroxy-3-(pyrrolidin-1-yl)propan-2-yl)-3-(3-methoxybenzyl)urea

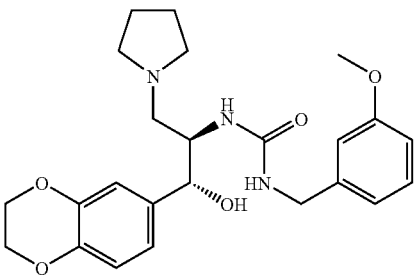 [SMILES: COc1cccc(CNC(=O)N[C@H](CN2CCCC2)[C@H](O)c2ccc3c(c2)OCCO3)c1]

¹H NMR (400 MHz, CDCl₃) δ=1.7 (s, 4H), 2.4-2.6 (m, 6H), 3.8 (s, 3H), 4.0 (m, 1H), 4.1-4.2 (s, 6H), 4.8 (d, 1H), 5.1 (d, 1H), 5.2-5.4 (br, 1H), 6.6-6.8 (m, 6H), 7.2 (dd, 1H); MS for $C_{24}H_{31}N_3O_5$ m/z 442.2 [M+H]

Example 3A6

Preparation of Compound 42: 1-((1R,2R)-1-(2,3-dihydrobenzo[β][1,4]dioxin-6-yl)-1-hydroxy-3-(pyrrolidin-1-yl)propan-2-yl)-3-(4-methylbenzyl)urea

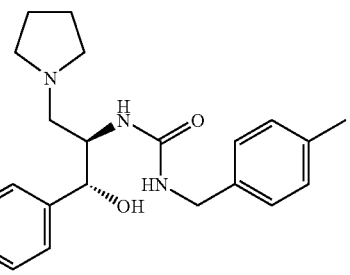

¹H NMR (400 MHz, CDCl₃) δ=1.6 (s, 4H), 2.3 (s, 3H), 2.4-2.6 (m, 6H), 4.0 (m, 1H), 4.2 (d, 2H), 4.21 (s, 4H), 4.7 (d,

1H), 5.2 (d, 1H), 5.4-5.6 (br, 1H), 6.7-7.1 (m, 7H); MS (for C$_{24}$H$_{31}$N$_3$O$_4$ m/z 426.2 [M+H]

Example 3A7

Preparation of Compound 43: 1-(4-chlorobenzyl)-3-((1R,2R)-1-(2,3-dihydrobenzo[β][1,4]dioxin-6-yl)-1-hydroxy-3-(pyrrolidin-1-yl)propan-2-yl)urea

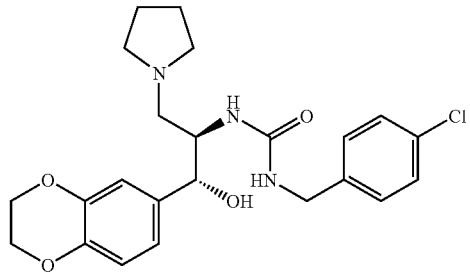 [SMILES: O=C(NCc1ccc(Cl)cc1)N[C@H](CN1CCCC1)[C@H](O)c1ccc2c(c1)OCCO2]

$^1$H NMR (400 MHz, CDCl$_3$) δ=1.7 (s, 4H), 2.5-2.7 (m, 6H), 4.0 (m, 1H), 4.2 (s, 6H), 4.8 (d, 1H), 5.2 (d, 1H), 5.4-5.5 (br, 1H), 6.7-6.9 (m, 3H), 7.1 (d, 2H), 7.3 (d, 2H); MS for C$_{23}$H$_{28}$N$_3$ClO$_4$ m/z 446 [M+H], 447.5 [M+2].

Example 3A8

Preparation of Compound 10: 1-((1R,2R)-1-(2,3-dihydrobenzo[β][1,4]dioxin-6-yl)-1-hydroxy-3-(pyrrolidin-1-yl)propan-2-yl)-3-((S)-1-phenylethyl)urea

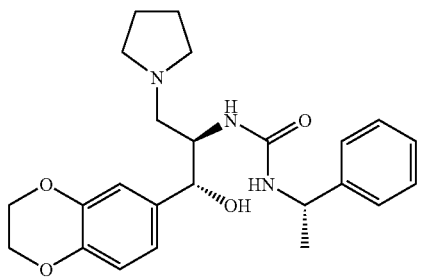 [SMILES: C[C@H](NC(=O)N[C@H](CN1CCCC1)[C@H](O)c1ccc2c(c1)OCCO2)c1ccccc1]

$^1$H NMR (400 MHz, CDCl$_3$) δ=1.4 (d, 3H), 1.6 (s, 4H), 2.2-2.5 (m, 4H), 2.5 (dd, 1H), 2.6 (dd, 1H), 3.9 (m, 1H), 4.2 (s, 4H), 4.5 (m, 1H), 4.8 (d, 1H), 5.0 (d, 1H), 5.1-5.3 (br, 1H), 6.6-6.9 (m, 3H), 7.2-7.4 (m, 5H); MS for C$_{24}$H$_{31}$N$_3$O$_4$ m/z 426.2 [M+H].

Example 3A9

Preparation of Compound 286: 1-((1R,2R)-1-(2,3-dihydrobenzo[β][1,4]dioxin-6-yl)-1-hydroxy-3-(pyrrolidin-1-yl)propan-2-yl)-3-((R)-1-phenylethyl)urea

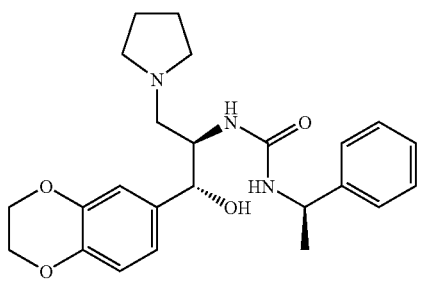 [SMILES: C[C@@H](NC(=O)N[C@H](CN1CCCC1)[C@H](O)c1ccc2c(c1)OCCO2)c1ccccc1]

$^1$H NMR (400 MHz, CDCl$_3$) δ=1.3 (d, 3H), 1.7 (s, 4H), 2.2-2.6 (m, 6H), 3.9 (m, 1H), 4.2 (s, 4H), 4.6-4.7 (m, 2H), 5.3 (d, 1H), 5.6-5.7 (br, 1H), 6.6 (d, 1H), 6.7 (d, 1H), 6.8 (s, 1H), 7.2-7.4 (m, 5H); MS for C$_{24}$H$_{31}$N$_3$O$_4$ m/z 426.0 [M+H].

Example 3A10

Preparation of Compound 69: 1-((1R,2R)-1-(2,3-dihydrobenzo[β][1,4]dioxin-6-yl)-1-hydroxy-3-(pyrrolidin-1-yl)propan-2-yl)-3-(naphthalen-2-yl)urea

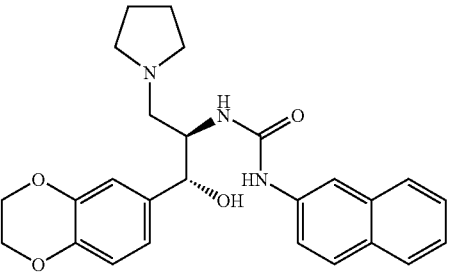 [SMILES: O=C(Nc1ccc2ccccc2c1)N[C@H](CN1CCCC1)[C@H](O)c1ccc2c(c1)OCCO2]

$^1$H NMR (400 MHz, CDCl$_3$) δ=1.6 (s, 4H), 2.4-2.8 (m, 6H), 4.1 (s, 5H), 4.8 (s, 1H), 6.0 (d, 1H), 6.7 (s, 2H), 6.9 (s, 1H), 7.1-7.8 (m, 7H); MS for C$_{26}$H$_{29}$N$_3$O$_4$ m/z 448.1 [M+H].

Example 3A11

Preparation of Compound 288: 1-((1R,2R)-1-(2,3-dihydrobenzo[β][1,4]dioxin-6-yl)-1-hydroxy-3-(pyrrolidin-1-yl)propan-2-yl)-3-(naphthalen-1-yl)urea

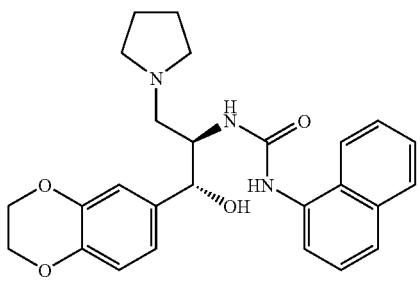 [SMILES: O=C(Nc1cccc2ccccc12)N[C@H](CN1CCCC1)[C@H](O)c1ccc2c(c1)OCCO2]

$^1$H NMR (400 MHz, CDCl$_3$) δ=1.6 (s, 4H), 2.4 (s, 4H), 2.6 (d, 2H), 4.1 (m, 1H), 4.2 (s, 4H), 4.8 (d, 1H), 5.4 (d, 1H), 6.5 (d, 1H), 6.6 (d, 1H), 6.7 (s, 1H), 7.2-7.6 (m, 3H), 7.7 (d, 1H), 7.8 (d, 1H), 8.0 (d, 1H); MS for C$_{26}$H$_{29}$N$_3$O$_4$ m/z 448.1 [M+H].

Example 3A12

Preparation of Compound 71: 1-((1R,2R)-1-(2,3-dihydrobenzo[β][1,4]dioxin-6-yl)-1-hydroxy-3-(pyrrolidin-1-yl)propan-2-yl)-3-((S)-1-(naphthalen-1-yl)ethyl)urea

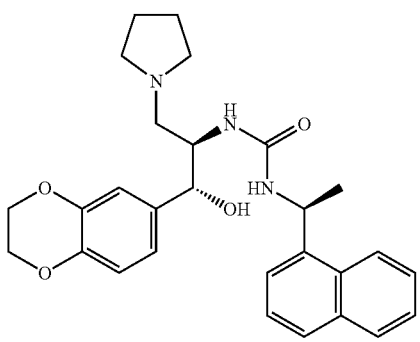 [SMILES: C[C@H](NC(=O)N[C@H](CN1CCCC1)[C@H](O)c1ccc2c(c1)OCCO2)c1cccc2ccccc12]

¹H NMR (400 MHz, CDCl₃) δ=1.4 (s, 4H), 1.5 (d, 3H), 2.3 (s, 4H), 2.4 (dd, 1H), 2.6 (dd, 1H), 3.9 (br, 1H), 4.2 (s, 4H), 4.7 (s, 1H), 5.0 (d, 1H), 5.3 (br, 1H), 5.5 (br, 1H), 6.6 (m, 3H), 7.4-7.6 (m, 4H), 7.7 (d, 1H), 7.8 (d, 1H), 8.1 (d, 1H); MS for C₂₈H₃₃N₃O₄ m/z 476.2 [M+H].

Example 3A13

Preparation of Compound 70: 1-(biphenyl-4-yl)-3-((1R,2R)-1-(2,3-dihydrobenzo[β][1,4]dioxin-6-yl)-1-hydroxy-3-(pyrrolidin-1-yl)propan-2-yl)urea

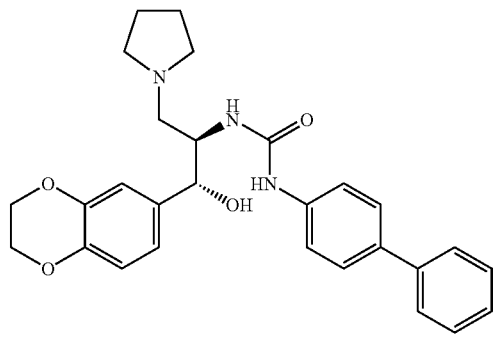 [SMILES: O=C(Nc1ccc(-c2ccccc2)cc1)N[C@H](CN1CCCC1)[C@H](O)c1ccc2c(c1)OCCO2]

¹H NMR (400 MHz, CDCl₃) δ=1.7 (s, 4H), 2.6-2.8 (m, 6H), 4.1 (br, 1H), 4.2 (s, 4H), 4.9 (br, 1H), 5.9 (d, 1H), 6.8 (s, 2H), 6.9 (s, 1H), 7.2-7.6 (m, 9H); for C₂₈H₃₁N₃O₄ m/z 474.1 [M+H].

Example 3A14

Preparation of Compound 81: 1-((1R,2R)-1-(2,3-dihydrobenzo[β][1,4]dioxin-6-yl)-1-hydroxy-3-(pyrrolidin-1-yl)propan-2-yl)-3-(4-(trifluoromethyl)phenyl)urea

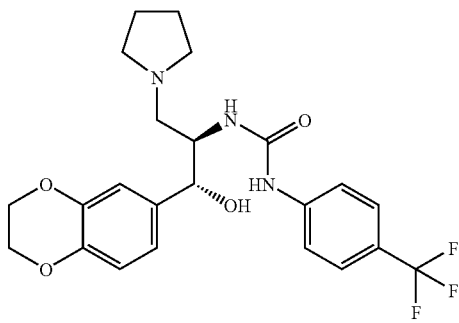 [SMILES: O=C(Nc1ccc(C(F)(F)F)cc1)N[C@H](CN1CCCC1)[C@H](O)c1ccc2c(c1)OCCO2]

¹H NMR (400 MHz, CDCl₃) δ=1.7 (s, 4H), 2.4-2.7 (m, 6H), 4.0 (br, 1H), 4.2 (s, 4H), 4.8 (br, 1H), 5.9 (br, 1H), 6.8 (s, 2H), 6.9 (s, 1H), 7.3 (d, 2H), 7.5 (d, 2H); MS for C₂₃H₂₆F₃N₃O₄ m/z 465.97 [M+H].

Example 3A15

Preparation of Compound 68: 1-((1R,2R)-1-(2,3-dihydrobenzo[β][1,4]dioxin-6-yl)-1-hydroxy-3-(pyrrolidin-1-yl)propan-2-yl)-3-(3-(trifluoromethyl)phenyl)urea

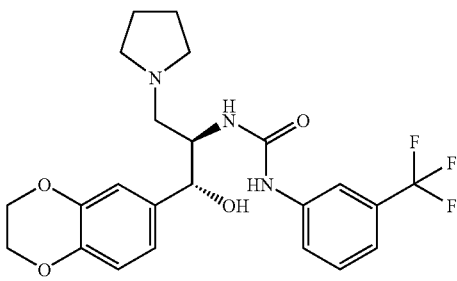 [SMILES: O=C(Nc1cccc(C(F)(F)F)c1)N[C@H](CN1CCCC1)[C@H](O)c1ccc2c(c1)OCCO2]

¹H NMR (400 MHz, CDCl₃) δ=1.7 (s, 4H), 2.5-2.9 (m, 6H), 4.0 (br, 1H), 4.2 (s, 4H), 4.8 (br, 1H), 5.9 (br, 1H), 6.8 (s, 2H), 6.9 (s, 1H), 7.2-7.6 (m, 4H); MS for C₂₃H₂₆F₃N₃O₄ m/z 466.0 [M+H].

Example 3A16

Preparation of Compound 82: 1-((1R,2R)-1-(2,3-dihydrobenzo[β][1,4]dioxin-6-yl)-1-hydroxy-3-(pyrrolidin-1-yl)propan-2-yl)-3-(4-(trifluoromethoxy)phenyl)urea

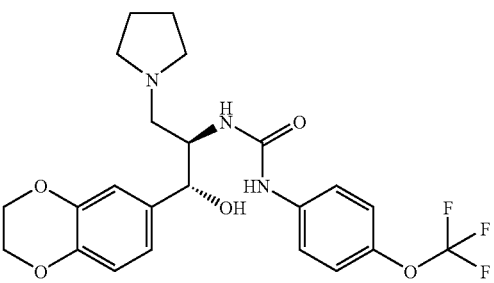 [SMILES: O=C(Nc1ccc(OC(F)(F)F)cc1)N[C@H](CN1CCCC1)[C@H](O)c1ccc2c(c1)OCCO2]

¹H NMR (400 MHz, CDCl₃) δ=1.7 (s, 4H), 2.4-2.7 (m, 6H), 4.0 (br, 1H), 4.2 (s, 4H), 4.8 (br, 1H), 5.9 (br, 1H), 6.8 (s, 2H), 6.9 (s, 1H), 7.0 (d, 2H), 7.2 (d, 2H); MS for C₂₃H₂₆F₃N₃O₅ m/z 481.5 [M], 482.5 [M+H].

Example 3A17

Preparation of Compound 133: 1-((1R,2R)-1-(2,3-dihydrobenzo[β][1,4]dioxin-6-yl)-1-hydroxy-3-(pyrrolidin-1-yl)propan-2-yl)-3-(4-(2-methylthiazol-4-yl)phenyl)urea

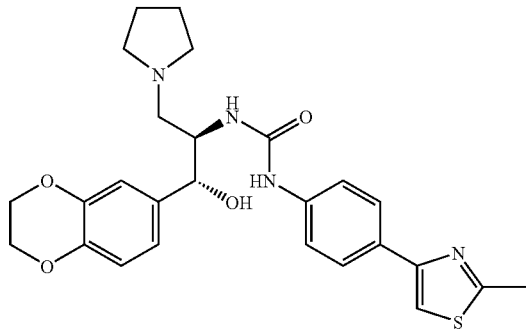 [SMILES: Cc1nc(-c2ccc(NC(=O)N[C@H](CN3CCCC3)[C@H](O)c3ccc4c(c3)OCCO4)cc2)cs1]

¹H NMR (400 MHz, CDCl₃) δ=1.7 (s, 4H), 2.4-2.7 (m, 6H), 2.7 (s, 3H), 4.1 (br, 1H), 4.2 (s, 4H), 4.8 (br, 1H), 5.9 (d, 1H), 6.8 (s, 2H), 6.9 (s, 1H), 7.2 (s, 1H), 7.3 (d, 2H), 7.7 (d, 2H); MS for C₂₆H₃₀N₄O₄S m/z 494.9 [M+H].

Example 3A18

Preparation of Compound 7: 1-((1R,2R)-1-(2,3-dihydrobenzo[β][1,4]dioxin-6-yl)-1-hydroxy-3-(pyrrolidin-1-yl)propan-2-yl)-3-dodecylurea

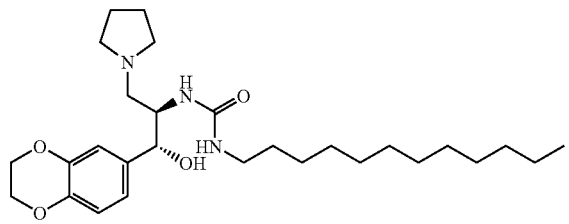 [SMILES: CCCCCCCCCCCCNC(=O)N[C@H](CN1CCCC1)[C@H](O)c1ccc2c(c1)OCCO2]

¹H NMR (400 MHz, CDCl₃) δ=0.9 (t, 3H), 1.3 (br, 18H), 1.4 (m, 2H), 1.8 (s, 4H), 2.5-2.7 (m, 6H), 3.1 (q, 2H), 4.0 (m, 1H), 4.3 (s, 4H), 4.4 (br, 1H), 4.76 (d, 1H), 4.8 (d, 1H), 6.7-6.8 (dd, 2H), 6.9 (s, 1H); MS for C₂₈H₄₇N₃O4 m/z 489.7 [M+H], 490.9 [M+2].

Example 3A19

Preparation of Compound 287: 1-((1R,2R)-1-(2,3-dihydrobenzo[β][1,4]dioxin-6-yl)-1-hydroxy-3-(pyrrolidin-1-yl)propan-2-yl)-3-(2-(thiophen-2-yl)ethyl)urea

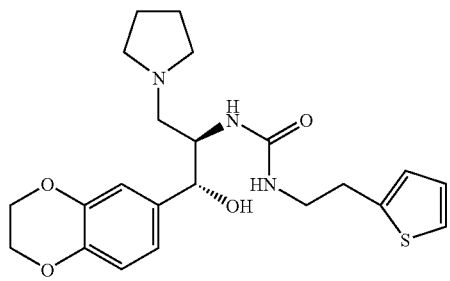 [SMILES: O=C(NCCc1cccs1)N[C@H](CN1CCCC1)[C@H](O)c1ccc2c(c1)OCCO2]

¹H NMR (400 MHz, CDCl₃) δ=1.7 (s, 4H), 2.5-2.7 (m, 6H), 3.0 (t, 2H), 3.8 (q, 2H), 4.0 (m, 1H), 4.2 (s, 4H), 4.8 (d, 2H), 4.9 (d, 1H), 6.7-6.8 (m, 3H), 6.9 (d, 1H), 6.9 (dd-1H), 7.1 (d, 1H); MS for C₂₂H₂₉N₃O4S m/z 432.1 [M+H].

Example 3A20

Preparation of Compound 257: N-((1R,2R)-1-(2,3-dihydrobenzo[β][1,4]dioxin-6-yl)-1-hydroxy-3-morpholinopropan-2-yl)-3-(4-methoxyphenoxy)propanamide

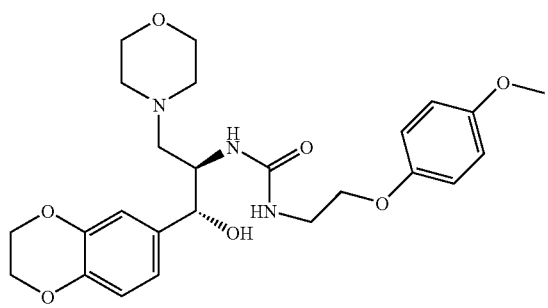 [SMILES: COc1ccc(OCCNC(=O)N[C@H](CN2CCOCC2)[C@H](O)c2ccc3c(c2)OCCO3)cc1]

¹H NMR (400 MHz, CDCl₃) δ=2.4-2.6 (m, 7H), 2.7 (dd, 1H), 3.5-3.7 (m, 4H), 3.8 (s, 3H), 4-4.2 (m, 2H), 4.2 (s, 4H), 4.2-4.3 (m, 1H), 4.9 (d, 1H), 6.5 (d, 1H), 6.7-6.9 (m, 7H); MS for C₂₅H₃₂N₂O₇ m/z 473.1 [M+H].

Example 3A21

Preparation of Compound 261: N-((1R,2R)-1-(2,3-dihydrobenzo[β][1,4]dioxin-6-yl)-1-hydroxy-3-(piperidin-1-yl)propan-2-yl)-3-(4-methoxyphenoxy)propanamide

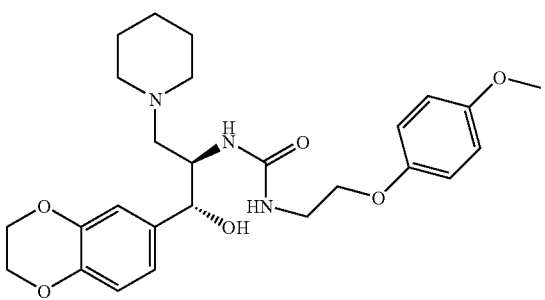 [SMILES: COc1ccc(OCCNC(=O)N[C@H](CN2CCCCC2)[C@H](O)c2ccc3c(c2)OCCO3)cc1]

¹H NMR (400 MHz, CDCl₃) δ=1.4 (br, 2H), 1.6 (br, 4H), 2.2-2.8 (m, 6H), 3.8 (s, 3H), 4.0-4.2 (m, 2H), 4.2 (s, 4H), 4.2-4.3 (m, 1H), 4.9 (s, 1H), 6.4 (d, 1H), 6.7-6.9 (m, 7H); MS for C₂₅H₃₄N₂O₆ m/z 471.1 [M+H].

Example 4

Compound A (N-((1R,2R)-1-(2,3-dihydrobenzo[b][1,4]dioxin-6-yl)-1-hydroxy-3-(pyrrolidin-1-yl)propan-2-yl)nonanamide) Effectively Inhibited PKD in a Mouse Model

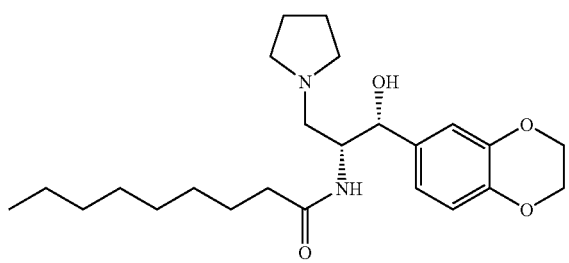 [SMILES: CCCCCCCCC(=O)N[C@H](CN1CCCC1)[C@H](O)c1ccc2c(c1)OCCO2]

Design:

jck mice was administered Compound A ad libitum in feed (0.225% Compound A mixed with a standard diet chow in powdered format) from 26-64 days of age. Control jck mice were fed a control powdered diet from 26-64 days of age. At 63 days of age, animals were transferred to metabolic cages for 24 hour urine collection. At 64 days of age, animals were sacrificed by CO₂ administration. Blood was collected by heart puncture for serum isolation. Kidneys were isolated and bisected; half of each kidney was fixed in 4% paraformaldehyde in PBS overnight for paraffin embedding and H&E staining.

Results:

Results are summarized in table 1 and discussed below.

TABLE 1

Summary of results, 0.225% Compound A in feed, 26-64 days of age

| No of animals | Gender | Dose (mg/kg) | Body weight (g) | K/BW ratio (%) | Cystic volume (% BW) | BUN (mg/dL) |
|---|---|---|---|---|---|---|
| 9 | M | Vehicle | 22.03 ± 1.58 | 7.55 ± 1.65 | 2.86 ± 1.04 | 90.11 ± 10.02 |
| 9 | M | Treated | 18.43 ± 1.82* | 4.46 ± 0.46* | 0.88 ± 0.23* | 39.25 ± 10.70* |
| 10 | F | Vehicle | 19.20 ± 1.80 | 4.94 ± 0.73 | 1.22 ± 0.41 | 50.50 ± 14.32 |
| 10 | F | Treated | 15.93 ± 1.65* | 3.57 ± 0.58* | 0.58 ± 0.29* | 34.67 ± 9.41* |

*p < 0.05% compared to control (2-tailed t-test)

Kidney and Body Weights

Total body weight and kidney weight were determined at sacrifice. A statistically significant decrease in total body weight was noted (p-value <0.05, two-tailed t-test). A significant difference in kidney weight/body weight ratio was also observed (p-value <0.05, two-tailed t-test) for the treated animals, suggesting efficacy of the drug.

Cyst Volume:

Cyst volume was measured by quantitating the percentage of cystic area in histological sections of kidneys from the treated and control animals, multiplied by the kidney/body weight ratio. A significant decrease in cyst volume was observed (p-value <0.05, two-tailed t-test) for the treated animals.

Kidney Function:

Blood urea nitrogen (BUN) levels were determined in serum samples derived from animals at sacrifice. BUN levels were elevated in the untreated controls, while the treated animals demonstrated a significant reduction of BUN levels (p-value <0.05, two-tailed t-test).

CONCLUSION

Administration of Compound A in feed at 0.225% resulted in a statistically significant reduction of cystic disease, as measured by kidney/body weight ratio and cyst volume. This was accompanied by improved renal function in treated animals relative to controls. These improvements were observed in both males and females. Therefore, these results demonstrate that glucosylceramide synthase inhibition is an effective strategy to treat polycystic kidney disease.

While this invention has been particularly shown and described with references to example embodiments thereof, it will be understood by those skilled in the art that various changes in form and details may be made therein without departing from the scope of the invention encompassed by the appended claims.

What is claimed is:

1. A method of treating polycystic kidney disease in a subject having polycystic kidney disease, comprising administering to the subject an effective amount of a compound represented by the following structural formula:

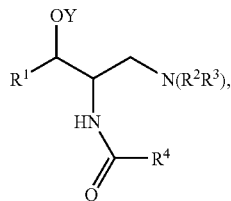

or a pharmaceutically acceptable salt thereof, wherein
$R^1$ is a phenyl group optionally and independently substituted with one or more substituents selected from the group consisting of —$OR^{30}$, alkyl, and —O—$[CH_2]_p$—O—;

each $R^{30}$ is independently i) hydrogen;

ii) a phenyl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or iii) a C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl;

each p is independently 1, 2, 3 or 4;

—$N(R^2R^3)$ is a pyrrolidinyl group optionally substituted with one or more substituents selected from the group consisting of halogen, C1-C5 alkyl, C1-C5 haloalkyl, hydroxyl, C1-C5 alkoxy, nitro, cyano, C1-C5 alkoxycarbonyl, C1-C5 alkylcarbonyl, C1-C5 haloalkoxy, amino, C1-C5 alkylamino and C1-C5 dialkylamino;

$R^4$ is C6-C8 alkyl; and

Y is —H.

2. The method of claim 1, wherein each $R^{30}$ is independently i) hydrogen; or ii) a C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl.

3. The method of claim 1, wherein —$N(R^2R^3)$ is an unsubstituted pyrrolidinyl group.

4. The method of claim 1, wherein $R^1$ is 4-hydroxyphenyl or 3,4-ethylenedioxy-1-phenyl.

5. The method of claim 1, wherein the polycystic kidney disease is an autosomal dominant polycystic kidney disease.

6. A method of treating polycystic kidney disease in a subject having polycystic kidney disease, comprising administering to the subject an effective amount of a compound represented by the following structural formula:

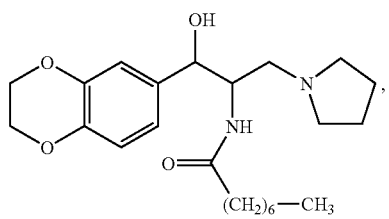

or a pharmaceutically acceptable salt thereof.

7. A method of treating polycystic kidney disease in a subject having polycystic kidney disease, comprising administering to the subject an effective amount of a compound represented by the following structural formula:

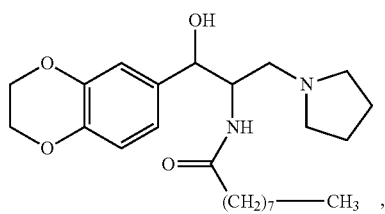

or a pharmaceutically acceptable salt thereof.

8. The method of claim 1, wherein the compound is represented by the following structural formula:

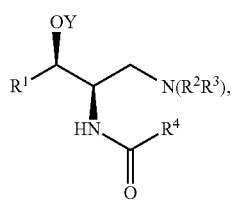

or a pharmaceutically acceptable salt thereof.

9. The method of claim 6, wherein the compound is represented by the following structural formula:

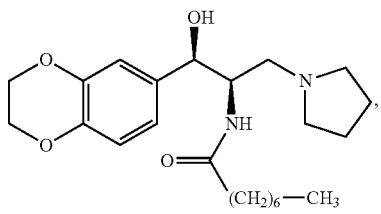

or a pharmaceutically acceptable salt thereof.

10. The method of claim 7, wherein the compound is represented by the following structural formula:

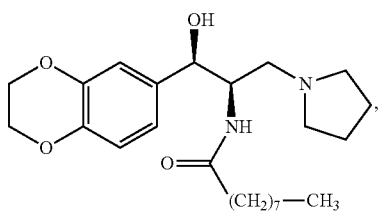

or a pharmaceutically acceptable salt thereof.

11. The method of claim 1, wherein $R^1$ is a phenyl group optionally and independently substituted with one or more substituents selected from the group consisting of —OH, —OCH$_3$, —OC$_2$H$_5$, C1-C6 alkyl and —O—[CH$_2$]$_p$—O—.

12. The method of claim 1, wherein $R^1$ is

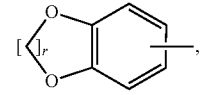

wherein r is 1 or 2.

13. The method of claim 1, wherein p is 1 or 2.

\* \* \* \* \*